United States Patent
Letourneau et al.

(10) Patent No.: US 11,306,098 B2
(45) Date of Patent: Apr. 19, 2022

(54) SUBSTITUTED PYRROLO[1,2-A]PYRAZINES AND PYRROLO[1,2-A][1,4]DIAZEPINES AS TREX1 INHIBITORS

(71) Applicant: VENENUM BIODESIGN, LLC, Hamilton, NJ (US)

(72) Inventors: Jeffrey J. Letourneau, East Windsor, NJ (US); Kiruthika Selvarangan Elamparuthi, Princeton Junction, NJ (US); Chia-Yu Huang, West Windsor, NJ (US); Venugopalareddy Bommireddy Venkata, Princeton Junction, NJ (US)

(73) Assignee: Venenum Biodesign, LLC, Hamilton, NJ (US)

( * ) Notice: Subject to any disclaimer, the term of this patent is extended or adjusted under 35 U.S.C. 154(b) by 35 days.

(21) Appl. No.: 16/829,655

(22) Filed: Mar. 25, 2020

(65) Prior Publication Data
US 2020/0317677 A1    Oct. 8, 2020

Related U.S. Application Data

(60) Provisional application No. 62/830,626, filed on Apr. 8, 2019.

(51) Int. Cl.
| | | |
|---|---|---|
| A61K 31/4985 | (2006.01) | |
| A61K 31/551 | (2006.01) | |
| C07D 487/04 | (2006.01) | |
| A61P 35/00 | (2006.01) | |
| A61K 45/06 | (2006.01) | |

(52) U.S. Cl.
CPC ............ *C07D 487/04* (2013.01); *A61P 35/00* (2018.01); *A61K 45/06* (2013.01)

(58) Field of Classification Search
CPC . A61K 31/4985; A61K 31/551; C07D 487/04
USPC .............. 514/211.09, 249; 540/567; 544/349
See application file for complete search history.

(56) References Cited

FOREIGN PATENT DOCUMENTS

WO    WO-2020210032 A1 * 10/2020 ............... A61P 35/00

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Andrea Ablasser, et al. Trex1 Deficiency Triggers Cell-Autonomous Immunity in a cGAS-Dependent Manner; 2014.
Daniel Stetson, et al. TREX1 pREVENTS cELL-Intrinsic Initiation of Autoimmunity, 2008.
Claire Vanpouille-Box, et al. DNA exonuclease Trex1 regulates radiotheraphy-induced tumour immunigenicity 2017.
Nan Yan; Immune Diseases Associated with TREX1 and STING Dysfunction; 2017.
Yun-Gui Yang; Trex1 Exonuclease Degrades ssDNA to Prevent Chronic Checkpoint Activation and Autoimmune Disease, 2007.

* cited by examiner

*Primary Examiner* — Douglas M Willis
(74) *Attorney, Agent, or Firm* — Heslin Rothenberg Farley & Mesiti, P.C.

(57) ABSTRACT

The present invention provides compounds of Formula I

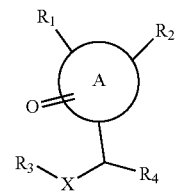

wherein

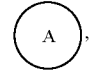

$X$, $R_1$, $R_2$, $R_3$ and $R_4$ are as defined herein, or a stereoisomer, tautomer, pharmaceutically acceptable salt, prodrug ester or solvate form thereof, wherein all of the variables are as defined herein. These compounds are effective at modulating the TREX1 protein and thus can be used as medicaments for treating or preventing disorders affected by the inhibition of TREX1.

13 Claims, No Drawings

Specification includes a Sequence Listing.

SUBSTITUTED PYRROLO[1,2-A]PYRAZINES AND PYRROLO[1,2-A][1,4]DIAZEPINES AS TREX1 INHIBITORS

CROSS REFERENCES TO RELATED APPLICATIONS

This application claims the benefit under 35 U.S.C. § 119 (e) to U.S. Provisional Application No. 62/830,626, filed on Apr. 8, 2019, the contents of which are incorporated by reference herein in its entirety.

FIELD OF THE INVENTION

The present invention provides novel cyclic compounds, and analogues thereof, which are three prime repair exonuclease 1 (TREX1) inhibitors and are useful in preventing or treating disorders associated with TREX1. This invention also relates to pharmaceutical compositions containing these compounds and methods of using the same.

BACKGROUND OF THE INVENTION

Three-prime repair exonuclease 1 (gene name TREX-1), also called Deoxyribonuclease III or DNase III, is an enzyme that degrades deoxyribonucleic acid by cleaving the 3' terminal base of a DNA polymer. TREX1 can digest single-stranded and double-stranded DNA containing a mismatched 3' overhang. TREX1 is an endoplasmic reticulum-associated cytosolic protein and can also be found in the nucleus.

TREX1 functions to prevent cell-intrinsic initiation of autoimmunity by degrading cytosolic self DNA from endogenous retroelements (Stetson, D. B et al. (2008) Cell. 134(4). 587-598). TREX 1 prevents chronic ATM-dependent checkpoint activation by processing ssDNA polynucleotide species arising from the processing of aberrant DNA replication intermediates (Yang Y. G. et. al. (2007) Cell 131(5), 873-86). Cytosolic DNA fragments and retroelements are sensed by pattern recognition receptors, such as cyclic GMP-AMP synthase (gene name cGAS). When cGAS binds DNA its enzyme activity is greatly enhanced and it produces cyclic GMP-AMP which serves as a secondary messenger that binds to and activates Stimulator of Interferon Genes (STING) and thereby initiating a type 1 interferon immune response (Wu J. et al., (2012) Science. 339(6121), 826-30; Sun L. et al., (2012). Science. 339(6121). TREX1 DNA degrading activity can attenuate such responses as a check to prevent excessive type 1 interferon responses.

Defects in TREX1 have numerous biological consequences. Defects in TREX1 function are associated with type 1 interferon driven systemic inflammatory and autoimmune conditions. These include Familial Chilblain Lupus, Aicardi-Goutie'res syndrome (AGS), Retinal Vasculopathy and Cerebral leukodystrophy (RVCL) (Ablasser, A. et al. (2014) J. Immun. 192, 5993-5997). Similar to activating mutations of STING (Jeremiah, N. et al. (2014) JCI, 124 (12), 5516-5520), inactivating mutations in TREX1 (Yan, N. et al. (2017) J. Interfer. Cyt. Res. 2017 37(5), 198-206) are associated with type 1 interferon-driven systemic inflammatory and autoimmune conditions. It follows then that TREX1 inhibitors should have the same therapeutic consequence as STING agonists in the context of cancer immunotherapy. TREX1 inhibitors can be used in combinatorial strategies to maximizing the immunogenicity of radiation therapy (Vanpouille-Box (2017) Nature Commun. 8, 81658). Inactivating mutations in TREX1 confers resistance to RNA viruses, including HIV, VSV, influenza, West Nile and Sendai viruses. Therefore, TREX1 inhibition could be used in antiviral therapy as well.

The potential therapeutic benefits of enhancing both innate and adaptive immunity make TREX1 an attractive therapeutic target that demonstrates impressive activity by itself and can also be combined with other immunotherapies.

SUMMARY OF THE INVENTION

It has been found that cyclic compounds in accordance with the present invention are effective at inhibiting TREX1 in assays. Accordingly, the present invention provides novel cyclic analogues which are TREX1 inhibitors and are useful as selective immunotherapies, including stereoisomers, tautomers, pharmaceutically acceptable salts, solvates, or prodrug esters thereof.

The present invention also provides processes and intermediates for making the compounds of the present invention or stereoisomers, tautomers, pharmaceutically acceptable salts, solvates, or prodrug esters thereof.

The present invention also provides pharmaceutical compositions comprising a pharmaceutically acceptable carrier and at least one of the compounds of the present invention or stereoisomers, tautomers, pharmaceutically acceptable salts, solvates, or prodrug esters thereof.

The present invention also provides a method for the treatment or prophylaxis of disorders, diseases, syndromes, or conditions affected by the inhibition of TREX1 comprising administering to a patient in need of such treatment or prophylaxis a therapeutically effective amount of at least one of the compounds of the present invention or stereoisomers, tautomers, pharmaceutically acceptable salts, solvates, or prodrug esters thereof.

The present invention also provides the compounds of the present invention or stereoisomers, tautomers, pharmaceutically acceptable salts, solvates, or prodrug esters thereof, for use in therapy.

The present invention also provides the use of the compounds of the present invention or stereoisomers, tautomers, pharmaceutically acceptable salts, solvates, or prodrug esters thereof, for the manufacture of a medicament for the treatment or prophylaxis of a disorder, disease, syndrome, or condition affected by the inhibition of TREX1.

Other features and advantages of the invention will be apparent from the following detailed description and claims.

DETAILED DESCRIPTION

In one embodiment, the present invention provides cyclic compounds, stereoisomers, tautomers, salts, solvates or prodrugs thereof, of Formula I having the structure:

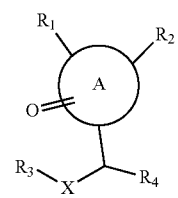

I wherein:
A is a 6 to 7-membered monocyclic heterocyclyl or a 8- to 12-membered bicyclic heterocyclyl, wherein the bicyclic heterocyclyl contains at least two N atoms;

X is independently selected from —C(═O)—NR$_5$—; —C(═O)—NR$_5$—S(═O)$_2$—; —C$_1$-C$_6$ alkyl-NR$_5$—S(═O)$_2$—; —C$_1$-C$_6$ alkyl-NR$_5$—C(═O)—; and a 5-membered nitrogen containing heteroaryl;

R$_1$ is independently selected from —C$_1$-C$_6$ alkyl-NR$_5$R$_6$ and —NR$_5$R$_6$;

R$_2$ is independently selected from C$_1$-C$_6$ alkyl, C$_6$-C$_{10}$ aryloxy-C$_1$-C$_6$-alkyl, C$_6$-C$_{10}$ aryl-S—C$_1$-C$_6$-alkyl, C$_6$-C$_{10}$ aryl-S(═O)—C$_1$-C$_6$-alkyl, C$_6$-C$_{10}$ aryl-S(═O)$_2$—C$_1$-C$_6$-alkyl, C$_6$-C$_{10}$ aryl-C$_1$-C$_6$-alkyl, a 5- to 10-membered heteroaryl-oxy-C$_1$-C$_6$-alkyl, a 5- to 10-membered heteroaryl-S—C$_1$-C$_6$-alkyl, a 5- to 10-membered heteroaryl-S(═O)—C$_1$-C$_6$-alkyl, a 5- to 10-membered heteroaryl-S(═O)$_2$—C$_1$-C$_6$-alkyl and a 5- to 10-membered heteroaryl-C$_1$-C$_6$-alkyl, wherein any aryl and heteroaryl may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_4$ alkoxy;

R$_3$ is independently selected from C$_1$-C$_6$ alkyl, C$_6$-C$_{10}$ aryl, C$_6$-C$_{10}$ aryl-C$_1$-C$_6$-alkyl, a 5- to 10-membered heteroaryl-C$_1$-C$_6$-alkyl, and C$_3$-C$_6$ cycloalkyl-C$_1$-C$_6$-alkyl, wherein any cycloalkyl, aryl and heteroaryl, may be optionally substituted with one or more substituents selected from the group consisting of OH, CN, halo, C$_1$-C$_4$ alkyl, C$_1$-C$_4$ alkoxy, halo-C$_1$-C$_4$ alkyl or halo-C$_1$-C$_6$ alkoxy;

R$_4$ is C$_1$-C$_6$ alkyl, optionally substituted with one or more substituents selected from the group consisting of OH, CN, —C(═O)OH, —C(═O)NR$_8$R$_9$; —NR$_8$R$_9$; —O—NR$_8$R$_9$; —S(═O)$_2$OH; —S(═O)$_2$NR$_8$R$_9$; —NR$_8$—S(═O)$_2$—R$_9$; —C(═O)NR$_8$—S(═O)$_2$—R$_9$; —C(═O)NR$_8$—S(═O)$_2$—NR$_{28}$R$_{29}$; —NR$_{28}$—C(═O)NR$_8$—S(═O)$_2$—R$_9$; —NR$_{28}$—C(═O)NR$_8$R$_9$; —S(═O)$_2$—R$_9$; —S(═O)—R$_9$; —S—R$_9$; C$_6$-C$_{10}$ aryl, or a 5-membered nitrogen containing heteroaryl, wherein the aryl and heteroaryl may be optionally substituted with one or more substituents selected from the group consisting of OH, ═O, CN, halo, C$_1$-C$_4$ alkyl, C$_1$-C$_4$ alkoxy, halo-C$_1$-C$_4$ alkyl or halo-C$_1$-C$_4$ alkoxy;

R$_5$, at each occurrence, is independently selected from H, C$_1$-C$_6$ alkyl and halo C$_1$-C$_6$ alkyl;

R$_6$ is independently selected from H, C$_1$-C$_6$ alkyl, halo C$_1$-C$_6$ alkyl and —C(═O)R$_7$;

R$_7$ is independently selected from C$_1$-C$_6$ alkyl and C$_1$-C$_6$ alkoxy;

R$_8$ is independently selected from H, C$_1$-C$_4$ alkyl, C$_1$-C$_4$ alkoxy, halo-C$_1$-C$_4$-alkyl, —C(═O)—C$_1$-C$_4$ alkyl, and halo-C$_1$-C$_4$ alkoxy;

R$_9$ is independently selected from H, OH, C$_1$-C$_4$ alkyl, C$_1$-C$_4$ alkoxy, C$_3$-C$_6$ cycloalkyl and C$_6$-C$_{10}$ aryl, wherein the alkyl, alkoxy, cycloalkyl and aryl may be optionally substituted with one or more substituents selected from the group consisting of OH, ═O, CN, halo, C$_1$-C$_4$ alkyl, C$_1$-C$_4$ alkoxy, halo-C$_1$-C$_4$ alkyl or halo-C$_1$-C$_4$ alkoxy;

R$_{28}$ is independently selected from H, C$_1$-C$_4$ alkyl, C$_1$-C$_4$ alkoxy, halo-C$_1$-C$_4$-alkyl and halo-C$_1$-C$_4$ alkoxy; and R$_{29}$ is independently selected from H, C$_1$-C$_4$ alkyl, C$_1$-C$_4$ alkoxy, halo-C$_1$-C$_4$-alkyl and halo-C$_1$-C$_4$ alkoxy.

In another embodiment, the present invention provides compounds, stereoisomers, tautomers, salts, solvates or prodrugs thereof, wherein A is a 8- to 11-membered bicyclic heterocyclyl, wherein the bicyclic heterocyclyl contains at least two N atoms.

In yet another embodiment, the present invention provides compounds, stereoisomers, tautomers, salts, solvates or prodrugs thereof, wherein A is a 8- to 10-membered bicyclic heterocyclyl, wherein the bicyclic heterocyclyl contains at least two N atoms.

In still yet another embodiment, the present invention provides compounds, stereoisomers, tautomers, salts, solvates or prodrugs thereof, wherein A is

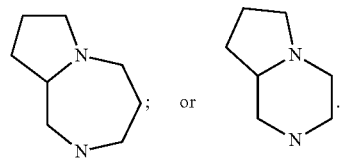 [SMILES: C1CNCC2CCCN2C1 ; C1CC2CNCCN2C1]

In one embodiment, the present invention provides compounds, stereoisomers, tautomers, salts, solvates or prodrugs thereof, wherein the compound is a compound of Formula Ia or Ib:

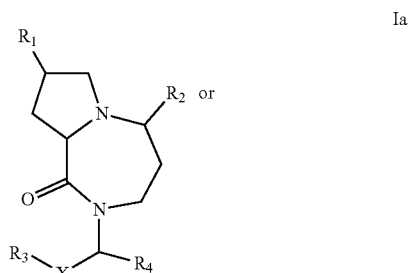

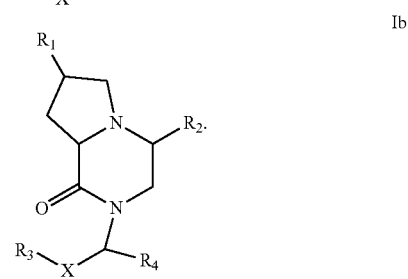

In one embodiment, the present invention provides compounds, stereoisomers, tautomers, salts, solvates or prodrugs thereof, wherein A is a 6- to 7-membered monocyclic heterocyclyl, wherein the heterocyclyl contains at least two N atoms.

In one embodiment, the present invention provides compounds, stereoisomers, tautomers, salts, solvates or prodrugs thereof, wherein X is independently selected from —C(═O)—NR$_5$—; —C(═O)—NR$_5$—S(═O)$_2$—; —C$_1$-C$_6$ alkyl-NR$_5$—C(═O)—; and a 5-membered nitrogen containing heteroaryl.

In yet another embodiment, the present invention provides compounds, stereoisomers, tautomers, salts, solvates or prodrugs thereof, wherein X is independently selected from —C(═O)—NR$_5$—; —C$_1$-C$_6$ alkyl-NR$_5$—C(═O)—; and a 5-membered nitrogen containing heteroaryl.

In yet another embodiment, the present invention provides compounds, stereoisomers, tautomers, salts, solvates or prodrugs thereof, wherein X is independently selected from —C(═O)—NR$_5$—; and —C$_1$-C$_6$ alkyl-NR$_5$—C(═O)—.

In yet another embodiment, the present invention provides compounds, stereoisomers, tautomers, salts, solvates or prodrugs thereof, wherein X is —C(═O)—NR$_5$—.

In still yet another embodiment, the present invention provides compounds, stereoisomers, tautomers, salts, solvates or prodrugs thereof, wherein $R_2$ is independently selected from $C_1$-$C_6$ alkyl, $C_6$-$C_{10}$ aryloxy-$C_1$-$C_6$-alkyl, $C_6$-$C_{10}$ aryl-S—$C_1$-$C_6$-alkyl, $C_6$-$C_{10}$ aryl-S(=O)$_2$—$C_1$-$C_6$-alkyl and $C_6$-$C_{10}$ aryl-$C_1$-$C_6$-alkyl, wherein any aryl may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_4$ alkoxy.

In one embodiment, the present invention provides compounds, stereoisomers, tautomers, salts, solvates or prodrugs thereof, wherein $R_2$ is independently selected from $C_1$-$C_6$ alkyl, $C_6$-$C_{10}$ aryloxy-$C_1$-$C_6$-alkyl, $C_6$-$C_{10}$ aryl-S—$C_1$-$C_6$-alkyl and $C_6$-$C_{10}$ aryl-$C_1$-$C_6$-alkyl, wherein any aryl may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_4$ alkoxy.

In another embodiment, the present invention provides compounds, stereoisomers, tautomers, salts, solvates or prodrugs thereof, wherein $R_2$ is independently selected from $C_1$-$C_6$ alkyl and $C_6$-$C_{10}$ aryl-$C_1$-$C_6$-alkyl, wherein the aryl may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_4$ alkoxy.

In yet another embodiment, the present invention provides compounds, stereoisomers, tautomers, salts, solvates or prodrugs thereof, wherein $R_3$ is independently selected from $C_1$-$C_6$ alkyl, $C_6$-$C_{10}$ aryl, $C_6$-$C_{10}$ aryl-$C_1$-$C_6$-alkyl, and a 5- to 10-membered heteroaryl-$C_1$-$C_6$-alkyl, wherein any $C_6$-$C_{10}$ aryl and heteroaryl, may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_6$ alkoxy.

In yet another embodiment, the present invention provides compounds, stereoisomers, tautomers, salts, solvates or prodrugs thereof, wherein $R_3$ is independently selected from $C_1$-$C_6$ alkyl, $C_6$-$C_{10}$ aryl, $C_6$-$C_{10}$ aryl-$C_1$-$C_6$-alkyl, a 5-membered heteroaryl-$C_1$-$C_6$-alkyl, and a 6-membered heteroaryl-$C_1$-$C_6$-alkyl, wherein any aryl and heteroaryl, may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_6$ alkoxy.

In yet another embodiment, the present invention provides compounds, stereoisomers, tautomers, salts, solvates or prodrugs thereof, wherein $R_3$ is independently selected from $C_1$-$C_6$ alkyl, $C_6$-$C_{10}$ aryl, and $C_6$-$C_{10}$ aryl-$C_1$-$C_6$-alkyl, wherein any aryl may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_6$ alkoxy.

In still yet another embodiment, the present invention provides compounds, stereoisomers, tautomers, salts, solvates or prodrugs thereof, wherein:

$R_4$ is $C_1$-$C_6$ alkyl, optionally substituted with one or more substituents selected from the group consisting of OH, CN, —C(=O)OH, —C(=O)NR$_8$R$_9$; $C_6$-$C_{10}$ aryl, or a 5-membered nitrogen containing heteroaryl, wherein the aryl and heteroaryl may be optionally substituted with OH, =O, CN, halo, $C_1$-$C_4$ alkyl, $C_1$-$C_4$ alkoxy, halo-$C_1$-$C_4$ alkyl or halo-$C_1$-$C_4$ alkoxy;

$R_8$ is independently selected from H, $C_1$-$C_4$ alkyl, $C_1$-$C_4$ alkoxy, halo-$C_1$-$C_4$-alkyl and halo-$C_1$-$C_4$ alkoxy; and $R_9$ is independently selected from H, $C_1$-$C_4$ alkyl, $C_1$-$C_4$ alkoxy, halo-$C_1$-$C_4$-alkyl and halo-$C_1$-$C_4$ alkoxy.

In one embodiment, the present invention provides compounds, stereoisomers, tautomers, salts, solvates or prodrugs thereof, wherein the 5-membered nitrogen containing heteroaryl in the definition of $R_4$ is selected from the group consisting of

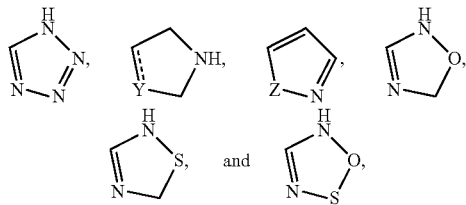

wherein Y is O, S, N or C and Z is O, S, or N(CH$_3$).

In another embodiment, the present invention provides compounds, stereoisomers, tautomers, salts, solvates or prodrugs thereof, wherein:

A is a 8- to 11-membered bicyclic heterocyclyl, wherein the bicyclic heterocyclyl contains at least two N atoms;

X is independently selected from —C(=O)—NR$_5$—; —C(=O)—NR$_5$—S(=O)$_2$—; —C$_1$-C$_6$ alkyl-NR$_5$—C(=O)—; and a 5-membered nitrogen containing heteroaryl;

$R_1$ is independently selected from —C$_1$-$C_6$ alkyl-NR$_5$R$_6$ and —NR$_5$R$_6$;

$R_2$ is independently selected from $C_1$-$C_6$ alkyl, $C_6$-$C_{10}$ aryloxy-$C_1$-$C_6$-alkyl, $C_6$-$C_{10}$ aryl-S—$C_1$-$C_6$-alkyl, $C_6$-$C_{10}$ aryl-S(=O)—$C_1$-$C_6$-alkyl, $C_6$-$C_{10}$ aryl-S(=O)$_2$—$C_1$-$C_6$-alkyl and $C_6$-$C_{10}$ aryl-$C_1$-$C_6$-alkyl, wherein any aryl may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_4$ alkoxy;

$R_3$ is independently selected from $C_1$-$C_6$ alkyl, $C_6$-$C_{10}$ aryl, $C_6$-$C_{10}$ aryl-$C_1$-$C_6$-alkyl, and a 5- to 10-membered heteroaryl-$C_1$-$C_6$-alkyl, wherein any $C_6$-$C_{10}$ aryl and heteroaryl, may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_6$ alkoxy;

$R_4$ is $C_1$-$C_6$ alkyl, optionally substituted with one or more substituents selected from the group consisting of OH, CN, —C(=O)OH, —C(=O)NR$_8$R$_9$; $C_6$-$C_{10}$ aryl, or a 5-membered nitrogen containing heteroaryl, wherein the aryl or heteroaryl may be optionally substituted with OH, =O, CN, halo, $C_1$-$C_4$ alkyl, $C_1$-$C_4$ alkoxy, halo-$C_1$-$C_4$ alkyl or halo-$C_1$-$C_4$ alkoxy;

$R_5$, at each occurrence, is independently selected from H, $C_1$-$C_6$ alkyl and halo $C_1$-$C_6$ alkyl;

$R_6$ is independently selected from H, $C_1$-$C_6$ alkyl, halo $C_1$-$C_6$ alkyl and —C(=O)R$_7$;

$R_7$ is independently selected from $C_1$-$C_6$ alkyl and $C_1$-$C_6$ alkoxy;

$R_8$ is independently selected from H, $C_1$-$C_4$ alkyl, $C_1$-$C_4$ alkoxy, and halo-$C_1$-$C_4$-alkyl; and $R_9$ is independently selected from H, $C_1$-$C_4$ alkyl, $C_1$-$C_4$ alkoxy, and halo-$C_1$-$C_4$-alkyl.

In yet another embodiment, the present invention provides compounds, stereoisomers, tautomers, salts, solvates or prodrugs thereof, wherein:

A is a 8- to 10-membered bicyclic heterocyclyl, wherein the bicyclic heterocyclyl contains at least two N atoms;

X is independently selected from —C(=O)—NR$_5$—; —C$_1$-$C_6$ alkyl-NR$_5$—C(=O)—; and a 5-membered nitrogen containing heteroaryl;

$R_1$ is independently selected from —C$_1$-$C_6$ alkyl-NR$_5$R$_6$ and —NR$_5$R$_6$;

$R_2$ is independently selected from $C_1$-$C_6$ alkyl, $C_6$-$C_{10}$ aryloxy-$C_1$-$C_6$-alkyl, $C_6$-$C_{10}$ aryl-S—$C_1$-$C_6$-alkyl and $C_6$-$C_{10}$ aryl-$C_1$-$C_6$-alkyl, wherein any aryl may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_4$ alkoxy;

$R_3$ is independently selected from $C_1$-$C_6$ alkyl, $C_6$-$C_{10}$ aryl, $C_6$-$C_{10}$ aryl-$C_1$-$C_6$-alkyl, and a 5-membered heteroaryl-$C_1$-$C_6$-alkyl, wherein any $C_6$-$C_{10}$ aryl and heteroaryl, may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_6$ alkoxy;

$R_4$ is $C_1$-$C_6$ alkyl, optionally substituted with one or more substituents selected from the group consisting of OH, CN, —C(=O)OH, —C(=O)NR$_8$R$_9$; $C_6$-$C_{10}$ aryl, or a 5-membered nitrogen containing heteroaryl, wherein the aryl or heteroaryl may be optionally substituted with OH, =O, CN, halo, $C_1$-$C_4$ alkyl, $C_1$-$C_4$ alkoxy, halo-$C_1$-$C_4$ alkyl or halo-$C_1$-$C_4$ alkoxy;

$R_5$, at each occurrence, is independently selected from H, $C_1$-$C_6$ alkyl and halo $C_1$-$C_6$ alkyl;

$R_6$ is independently selected from H, $C_1$-$C_6$ alkyl, halo $C_1$-$C_6$ alkyl and —C(=O)R$_7$;

$R_7$ is independently selected from $C_1$-$C_6$ alkyl and $C_1$-$C_6$ alkoxy;

$R_8$ is independently selected from H, $C_1$-$C_4$ alkyl, $C_1$-$C_4$ alkoxy, and halo-$C_1$-$C_4$-alkyl; and $R_9$ is independently selected from H, $C_1$-$C_4$ alkyl, $C_1$-$C_4$ alkoxy, and halo-$C_1$-$C_4$-alkyl.

In one embodiment, the present invention provides compounds, stereoisomers, tautomers, salts, solvates or prodrugs thereof, wherein:

A is a 8- to 10-membered bicyclic heterocyclyl, wherein the bicyclic heterocyclyl contains at least two N atoms;

X is independently selected from —C(=O)—NR$_5$—; and —$C_1$-$C_6$ alkyl-NR$_5$—C(=O)—;

$R_1$ is independently selected from —$C_1$-$C_6$ alkyl-NR$_5$R$_6$ and —NR$_5$R$_6$;

$R_2$ is independently selected from $C_1$-$C_6$ alkyl, $C_6$-$C_{10}$ aryloxy-$C_1$-$C_6$-alkyl, and $C_6$-$C_{10}$ aryl-$C_1$-$C_6$-alkyl, wherein any aryl may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_4$ alkoxy;

$R_3$ is independently selected from $C_1$-$C_6$ alkyl, $C_6$-$C_{10}$ aryl and $C_6$-$C_{10}$ aryl-$C_1$-$C_6$-alkyl, wherein any $C_6$-$C_{10}$ aryl may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_6$ alkoxy;

$R_4$ is $C_1$-$C_6$ alkyl, optionally substituted with one or more substituents selected from the group consisting of OH, CN, —C(=O)OH, —C(=O)NR$_8$R$_9$; or $C_6$-$C_{10}$ aryl, wherein the aryl may be optionally substituted with OH, CN, halo, $C_1$-$C_4$ alkyl, $C_1$-$C_4$ alkoxy, halo-$C_1$-$C_4$ alkyl or halo-$C_1$-$C_4$ alkoxy;

$R_5$, at each occurrence, is independently selected from H, $C_1$-$C_6$ alkyl and halo $C_1$-$C_6$ alkyl;

$R_6$ is independently selected from H, $C_1$-$C_6$ alkyl, halo $C_1$-$C_6$ alkyl and —C(=O)R$_7$;

$R_7$ is independently selected from $C_1$-$C_6$ alkyl and $C_1$-$C_6$ alkoxy;

$R_8$ is independently selected from H, $C_1$-$C_4$ alkyl, $C_1$-$C_4$ alkoxy, and halo-$C_1$-$C_4$-alkyl; and $R_9$ is independently selected from H, $C_1$-$C_4$ alkyl, $C_1$-$C_4$ alkoxy, and halo-$C_1$-$C_4$-alkyl.

In yet another embodiment, the present invention provides compounds, stereoisomers, tautomers, salts, solvates or prodrugs thereof, wherein:

A is

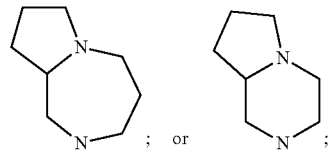 [SMILES: C1CNCC2CCCN2C1 ; C1CC2CNCCN2C1]

X is independently selected from —C(=O)—NR$_5$—; and —$C_1$-$C_6$ alkyl-NR$_5$—C(=O)—;

$R_1$ is independently selected from —$C_1$-$C_6$ alkyl-NR$_5$R$_6$ and —NR$_5$R$_6$;

$R_2$ is independently selected from $C_1$-$C_6$ alkyl and $C_6$-$C_{10}$ aryl-$C_1$-$C_6$-alkyl, wherein the aryl may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_4$ alkoxy;

$R_3$ is independently selected from $C_1$-$C_6$ alkyl, $C_6$-$C_{10}$ aryl, and $C_6$-$C_{10}$ aryl-$C_1$-$C_6$-alkyl, wherein any $C_6$-$C_{10}$ aryl may be optionally substituted with one or more substituents selected from the group consisting of OH, CN, halo, $C_1$-$C_4$ alkyl, $C_1$-$C_4$ alkoxy, halo-$C_1$-$C_4$ alkyl or halo-$C_1$-$C_6$ alkoxy;

$R_4$ is $C_1$-$C_6$ alkyl, optionally substituted with one or more substituents selected from the group consisting of OH, —C(=O)OH, —C(=O)NR$_8$R$_9$; or $C_6$-$C_{10}$ aryl, wherein the aryl may be optionally substituted with OH, CN, halo, $C_1$-$C_4$ alkyl, $C_1$-$C_4$ alkoxy, halo-$C_1$-$C_4$ alkyl or halo-$C_1$-$C_4$ alkoxy;

$R_5$, at each occurrence, is independently selected from H and $C_1$-$C_6$ alkyl;

$R_6$ is independently selected from H, $C_1$-$C_6$ alkyl and —C(=O)R$_7$;

$R_7$ is independently selected from $C_1$-$C_6$ alkyl and $C_1$-$C_6$ alkoxy;

$R_8$ is independently selected from H, $C_1$-$C_4$ alkyl and halo-$C_1$-$C_4$-alkyl; and $R_9$ is independently selected from H, $C_1$-$C_4$ alkyl and halo-$C_1$-$C_4$-alkyl.

In still yet another embodiment, the present invention provides compounds, stereoisomers, tautomers, salts, solvates or prodrugs thereof, wherein:

A is

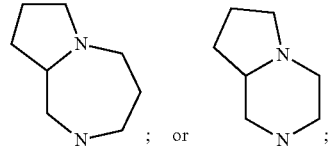 [SMILES: C1CNCC2CCCN2C1 ; C1CC2CNCCN2C1]

X is —C(=O)—NR$_5$—;

$R_1$ is —NR$_5$R$_6$;

$R_2$ is independently selected from $C_1$-$C_6$ alkyl and $C_6$-$C_{10}$ aryl-$C_1$-$C_6$-alkyl, wherein the aryl may be optionally substituted with one or more substituents selected from the group consisting of OH, CN, halo, $C_1$-$C_4$ alkyl or halo-$C_1$-$C_4$ alkyl;

$R_3$ is independently selected from $C_1$-$C_6$ alkyl, $C_6$-$C_{10}$ aryl, and $C_6$-$C_{10}$ aryl-$C_1$-$C_6$-alkyl, wherein any $C_6$-$C_{10}$ aryl may be optionally substituted with one or more substituents selected from the group consisting of OH, CN, halo, $C_1$-$C_4$ alkyl or halo-$C_1$-$C_4$ alkyl;

R$_4$ is C$_1$-C$_6$ alkyl, optionally substituted with one or more substituents selected from the group consisting of OH, —C(=O)OH, or C$_6$-C$_{10}$ aryl, wherein the aryl may be optionally substituted with OH, CN, halo, C$_1$-C$_4$ alkyl or halo-C$_1$-C$_4$ alkyl;

R$_5$, at each occurrence, is independently selected from H and C$_1$-C$_6$ alkyl;

R$_6$ is independently selected from H, C$_1$-C$_6$ alkyl and —C(=O)R$_7$; and

R$_7$ is independently selected from C$_1$-C$_6$ alkyl and C$_1$-C$_6$ alkoxy.

In one embodiment, the present invention provides compounds, stereoisomers, tautomers, salts, solvates or prodrugs thereof, wherein the compound is selected from a compound set forth in the examples.

In another embodiment, the present invention provides compounds, stereoisomers, tautomers, salts, solvates or prodrugs thereof, wherein the compound is selected from the compounds set forth in Examples 1, 2B, 3, 4, 14B, 15, 16, 17, 18, 36, 38, 39, 45 and 48.

The compounds, stereoisomers, tautomers, salts, solvates or prodrugs of the invention have IC$_{50}$ values in the TREX1 exonuclease assay (described hereinafter) of about 100 µM or less, preferably 50 µM or less, and more preferably 25 µM or less, even more preferably 10 µM or less. Activity data for compounds, stereoisomers, tautomers, salts, solvates or prodrugs of the present invention are presented in Table 5.

In some embodiments, the present invention provides a pharmaceutical composition, which includes a pharmaceutically acceptable carrier and a therapeutically effective amount of a compound of Formula I, preferably, a compound selected from one of the examples, more preferably, Examples 1, 2B, 3, 4, 14B, 15, 16, 17, 18, 36, 38, 39, 45 and 48, or stereoisomers, tautomers, pharmaceutically acceptable salts, prodrug esters, or solvates thereof, alone or in combination with another therapeutic agent.

In some embodiments, the present invention provides a pharmaceutical composition which further includes another therapeutic agent(s). In a preferred embodiment, the present invention provides a pharmaceutical composition, wherein the additional therapeutic agent(s) are an anti-cancer agent, an anti-viral compound, an antigen, an adjuvant, a lipid, a liposome, a peptide, a cytotoxic agent, a chemotherapeutic agent, an immunomodulatory cell line, a checkpoint inhibitor, a biotherapeutic agent, an immunogenic agent, and cells transfected with genes encoding immune stimulating cytokines or a combination thereof. Preferably, the additional therapeutic agents are VEGF, VEGFR, EGFR, Her2/neu, other growth factor receptors, CD20, CD40, CD-40L, CTLA-4, OX-40, 4-1BB, ICOS, IL-2, IFNa2, GM-CSF, a STING agonist, another TREX1 inhibitor, a CTLA-4 pathway antagonist, a LAG-3 pathway antagonist, a PD-1 pathway antagonist, a PD-L1 antibody, a vascular endothelial growth factor (VEGF) receptor inhibitor, a topoisomerase II inhibitor, a smoothen inhibitor, an alkylating agent, an anti-tumor antibiotic, an anti-metabolite, a retinoid, Tim-3/gal9, CD73 inhibitors, adenosine A2A+/−A2B antagonists and an anti-cancer vaccine.

In one embodiment, the present invention provides a pharmaceutical composition which is utilized in combination with radiation therapy.

In some embodiments, the present invention provides a method for the treatment or prophylaxis of a disorder, disease, syndrome, or condition, wherein said disease, syndrome, or condition is affected by the inhibition of TREX1, which includes the step of administering to a subject (for example, a human) in need of such treatment or prophylaxis a therapeutically effective amount of at least one of the compounds of the present invention or stereoisomers, tautomers, pharmaceutically acceptable salts, solvates, or prodrug esters thereof.

In some embodiments, the present invention provides methods for the treatment of a disorder, disease, syndrome, or condition affected by the inhibition of TREX1, which includes the steps of administering to a patient (for example, a human) in need thereof a therapeutically effective amount of a compound of Formula I, preferably, a compound selected from one of the examples, more preferably, Examples 1, 2B, 3, 4, 14B, 15, 16, 17, 18, 36, 38, 39, 45, and 48, or stereoisomers, tautomers, pharmaceutically acceptable salts, prodrug esters, or solvates thereof, wherein the disorder, disease, syndrome, or condition is selected cancer or a viral infection.

In some embodiments, the present invention provides methods for the treatment of a disease, syndrome, or condition affected by the inhibition of TREX1, which includes the steps of administering to a patient (for example, a human) in need thereof a therapeutically effective amount of a compound of Formula I, preferably, a compound selected from one of the examples, more preferably, Examples 1, 2B, 3, 4, 14B, 15, 16, 17, 18, 36, 38, 39, 45 and 48, or stereoisomers, tautomers, pharmaceutically acceptable salts, prodrug esters, or solvates thereof, wherein the disorder, disease, syndrome, or condition is cancer.

In some embodiments, the present invention provides methods for the treatment of cancer, which includes the steps of administering to a patient (for example, a human) in need thereof a therapeutically effective amount of a compound of Formula I, preferably, a compound selected from one of the examples, more preferably, Examples 1, 2B, 3, 4, 14B, 15, 16, 17, 18, 36, 38, 39, 45 and 48, or stereoisomers, tautomers, pharmaceutically acceptable salts, prodrug esters, or solvates thereof, in combination with radiation therapy.

In some embodiments, the present invention provides methods for the treatment of a disorder, disease, syndrome, or condition affected by the inhibition of TREX1, which includes the steps of administering to a patient (for example, a human) in need thereof a therapeutically effective amount of a compound of Formula I, preferably, a compound selected from one of the examples, more preferably, Examples 1, 2B, 3, 4, 14B, 15, 16, 17, 18, 36, 38, 39, 45 and 48, or stereoisomers, tautomers, pharmaceutically acceptable salts, prodrug esters, or solvates thereof, wherein the disorder, disease, syndrome, or condition is selected from the group consisting of melanoma, colon cancer, breast cancer, prostate cancer, lung cancer, bladder cancer and fibrosarcoma.

In some embodiments, the present invention provides methods for the treatment of a disorder, disease, syndrome, or condition affected by the inhibition of TREX1, which includes the steps of administering to a patient (for example, a human) in need thereof a therapeutically effective amount of a compound of Formula I, preferably, a compound selected from one of the examples, more preferably, Examples 1, 2B, 3, 4, 14B, 15, 16, 17, 18, 36, 38, 39, 45 and 48, or stereoisomers, tautomers, pharmaceutically acceptable salts, prodrug esters, or solvates thereof, wherein the disorder, disease, syndrome, or condition is a viral infection, preferably HIV.

In some embodiments, the present invention provides methods for the treatment of a disorder, disease, syndrome, or condition affected by the inhibition of TREX1, which includes the steps of administering to a patient (for example, a human) in need thereof a therapeutically effective amount of a compound of Formula I, preferably, a compound selected from one of the examples, more preferably, Examples 1, 2B, 3, 4, 14B, 15, 16, 17, 18, 36, 38, 39, 45 and 48, or stereoisomers, tautomers, pharmaceutically acceptable salts, prodrug esters, or solvates thereof, wherein the disorder, disease, syndrome, or condition is a HIV, melanoma, colon cancer, breast cancer, prostate cancer, lung cancer, bladder cancer or fibrosarcoma.

In yet another embodiment, the present invention provides uses a compound of Formula I, preferably, a compound selected from one of the examples, more preferably, Examples 1, 2B, 3, 4, 14B, 15, 16, 17, 18, 36, 38, 39, 45 and 48, or stereoisomers, tautomers, pharmaceutically acceptable salts, prodrug esters, or solvates thereof, for the preparation of a medicament for treating a disorder, disease, syndrome, or condition selected from the group consisting of viral infection, melanoma, colon cancer, breast cancer, prostate cancer, lung cancer, bladder cancer and fibrosarcoma, in a subject in need thereof.

In still yet another embodiment, the present invention provides uses a compound of Formula I, preferably, a compound selected from one of the examples, more preferably, Examples 1, 2B, 3, 4, 14B, 15, 16, 17, 18, 36, 38, 39, 45 and 48, or stereoisomers, tautomers, pharmaceutically acceptable salts, prodrug esters, or solvates thereof, in a method for treating a disorder, disease, syndrome, or condition selected from the group consisting of viral infection, melanoma, colon cancer, breast cancer, prostate cancer, lung cancer, bladder cancer and fibrosarcoma, in a subject in need thereof.

Other Embodiments of the Invention

In some embodiments, the present invention provides a process for making a compound of the present invention or a stereoisomer, tautomer, pharmaceutically acceptable salt, solvate or prodrug ester thereof.

In some embodiments, the present invention provides an intermediate for making a compound of the present invention or a stereoisomer, tautomer, pharmaceutically acceptable salt, solvate or prodrug ester thereof.

In some embodiments, the present invention provides a compound of the present invention or stereoisomers, tautomers, pharmaceutically acceptable salts, solvates, or prodrug esters thereof, for use in therapy for the treatment or prophylaxis of a disorder, disease, syndrome, or condition affected by the inhibition of TREX1.

In some embodiments, the present invention also provides the use of a compound of the present invention or stereoisomers, tautomers, pharmaceutically acceptable salts, solvates, or prodrug esters thereof, for the manufacture of a medicament for the treatment or prophylaxis of a disorder, disease, syndrome, or condition affected by the inhibition of TREX1.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

Chemistry

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. When no specific mention is made of the configuration (cis, trans or R or S) of a compound (or of an asymmetric carbon), then any one of the isomers or a mixture of more than one isomer is intended. Preferably, diastereomers are resolved prior to any type of in vitro or in vivo testing. The processes for preparation can use racemates, enantiomers, or diastereomers as starting materials. All processes used to prepare compounds of the present invention and intermediates made therein are considered to be part of the present invention. When enantiomeric or diastereomeric products are prepared, they can be separated by conventional methods, for example, by chromatography or fractional crystallization. Compounds of the present invention, and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene", alone or as part of another group, is intended to include both branched and straight-chain saturated aliphatic hydrocarbon groups having from 1 to 10 carbons or the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl), as well as chain isomers thereof, and the like as well as such groups which may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio as well as (=O), $OR_{18}$, $SR_{18}$, (=S), $-NR_{18}R_{19}$, $-N(alkyl)_3^+$, $-NR_{18}SO_2$, $-NR_{18}SO_2R_{20}$, $-SO_2R_{20}$, $-SO_2NR_{18}R_{19}$, $-SO_2NR_{18}C(=O)R_{19}$, $SO_3H$, $-PO(OH)_2$, $-C(=O)R_{18}$, $-CO_2R_{18}$, $-C(=O)NR_{18}R_{19}$, $-C(=O)(C_1$-$C_4$ alkylene)$NR_{18}R_{19}$, $-C(=O)NR_{18}(SO_2)R_{19}$, $-CO_2(C_1$-$C_4$ alkylene)

NR$_{18}$R$_{19}$, —NR$_{18}$C(=O)R$_{19}$, —NR$_{18}$CO$_2$R$_{19}$, —NR$_{18}$(C$_1$-C$_4$ alkylene)CO$_2$R$_{19}$, =N—OH, =N—O-alkyl, wherein R$_{18}$ and R$_{19}$ are the same or different and are independently selected from hydrogen, alkyl, alkenyl, CO$_2$H, CO$_2$(alkyl), C$_3$-C$_7$cycloalkyl, phenyl, benzyl, phenylethyl, naphthyl, a 4- to 7-membered heterocyclo, or a 5- to 6-membered heteroaryl, or when attached to the same nitrogen atom may join to form a heterocyclo or heteroaryl, and R$_{20}$ is selected from same groups as R$_{18}$ and R$_{19}$ but is not hydrogen. Each group R$_{18}$ and R$_{19}$ when other than hydrogen, and each R$_{20}$ group optionally has up to three further substituents attached at any available carbon or nitrogen atom of R$_{18}$, R$_{19}$, and/or R$_{20}$, said substituent(s) being the same or different and are independently selected from the group consisting of (C$_1$-C$_6$)alkyl, (C$_2$-C$_6$)alkenyl, hydroxy, halogen, cyano, nitro, CF$_3$, O(C$_1$-C$_6$ alkyl), OCF$_3$, C(=O)H, C(=O)(C$_1$-C$_6$ alkyl), CO$_2$H, CO$_2$(C$_1$-C$_6$ alkyl), NHCO$_2$(C$_1$-C$_6$ alkyl), —S(C$_1$-C$_6$ alkyl), —NH$_2$, NH(C$_1$-C$_6$ alkyl), N(C$_1$-C$_6$ alkyl)$_2$, N(CH$_3$)$_3^+$, SO$_2$(C$_1$-C$_6$ alkyl), C(=O)(C$_1$-C$_4$ alkylene)NH$_2$, C(=O)(C$_1$-C$_4$ alkylene)NH(alkyl), C(=O)(C$_1$-C$_4$ alkylene)N(C$_1$-C$_4$ alkyl)$_2$, C$_3$-C$_7$ cycloalkyl, phenyl, benzyl, phenylethyl, phenyloxy, benzyloxy, naphthyl, a 4- to 7-membered heterocyclo, or a 5- to 6-membered heteroaryl. When a substituted alkyl is substituted with an aryl, heterocyclo, cycloalkyl, or heteroaryl group, said ringed systems are as defined below and thus may have zero, one, two, or three substituents, also as defined below.

"Alkenyl" or "alkenylene", alone or as part of another group, is intended to include hydrocarbon chains of either straight or branched configuration and having one or more carbon-carbon double bonds that may occur in any stable point along the chain. For example, "C$_{2-6}$ alkenyl" (or alkenylene), is intended to include C$_2$, C$_3$, C$_4$, C$_5$, and C$_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, and 4-methyl-3-pentenyl, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, and/or alkylthio.

"Alkynyl" or "alkynylene", alone or as part of another group, is intended to include hydrocarbon chains of either straight or branched configuration and having one or more carbon-carbon triple bonds that may occur in any stable point along the chain. For example, "C$_{2-6}$ alkynyl" (or alkynylene), is intended to include C$_2$, C$_3$, C$_4$, C$_5$, and C$_6$ alkynyl groups; such as ethynyl, propynyl, butynyl, pentynyl, and hexynyl, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio.

The term "alkoxy" or "alkyloxy", alone or as part of another group, refers to an —O-alkyl group, where alkyl is as defined above. "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy", alone or as part of another group, represents an alkyl group or alkoxy group as defined above with the indicated number of carbon atoms attached through a sulphur bridge; for example methyl-S— and ethyl-S—.

"Halo" or "halogen", alone or as part of another group, includes fluoro, chloro, bromo, and iodo.

"Halo-C$_1$-C$_6$-alkyl" or "Haloalkyl" is intended to include both branched and straight-chain saturated aliphatic hydrocarbon groups having the specified number of carbon atoms, substituted with 1 to 7 halogens, preferably 1 to 4 halogens, preferably F and/or Cl. Examples of haloalkyl include, but are not limited to, fluoromethyl, difluoromethyl, trifluoromethyl, trichloromethyl, pentafluoroethyl, pentachloroethyl, 1,1-difluoroethyl, 1-fluoroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 to 7 fluorine atoms, preferably 1 to 4 fluorine atoms.

"Halo-C$_1$-C$_4$-alkoxy" or "haloalkyloxy" represents a haloalkyl group as defined above with the indicated number of carbon atoms attached through an oxygen bridge. For example, "C$_{1-6}$ haloalkoxy", is intended to include C$_1$, C$_2$, C$_3$, C$_4$, C$_5$, and C$_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl), and tricyclic alkyl, containing a total of 3 to 10 carbons forming the ring (C$_3$-C$_{10}$ cycloalkyl), and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl, cyclobutenyl, norbornyl,

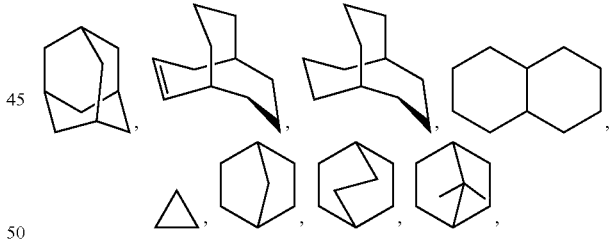

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl, as well as such groups including 2 free bonds and thus are linking groups.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "C$_{6-10}$ aryl" includes phenyl and naphthyl. Unless otherwise specified, "aryl", "C$_{6-10}$ aryl" or "aromatic residue" may be unsubstituted or substituted with 1 to 3 groups selected from OH, OC$_1$-C$_3$ alkoxy, Cl, F, Br, I, CN, NO$_2$, NH$_2$, N(CH$_3$)H, N(CH$_3$)$_2$, CF$_3$, OCF$_3$, OCHF$_2$, C(=O)CH$_3$, SCH$_3$, S(=O)CH$_3$, S(=O)$_2$CH$_3$, C$_1$-C$_3$ alkyl, CO$_2$H, and CO$_2$CH$_3$.

As used herein, the term "heterocycle," "heterocyclo", "heterocyclyl" or "heterocyclic" group is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may optionally be substituted on carbon or on a nitrogen atom if the resulting compound is stable, with 1 to 3 groups selected from OH, OC$_1$-C$_3$ alkoxy, Cl, F, Br, I, CN, NO$_2$, NH$_2$, N(CH$_3$)H, N(CH$_3$)$_2$, CF$_3$, OCF$_3$, OCHF$_2$, =O, C(=O)CH$_3$, SCH$_3$, S(=O)CH$_3$, S(=O)$_2$CH$_3$, C$_1$-C$_3$ alkyl, CO$_2$H and CO$_2$CH$_3$. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. Spiro and bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. When the term "heterocycle" or "heterocyclyl" is used, it is not intended to include heteroaryl.

Exemplary monocyclic heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, and tetrahydro-1,1-dioxothienyl, and the like.

Exemplary bicyclic heterocyclo groups include quinuclidinyl.

Preferred heterocyclo groups include:

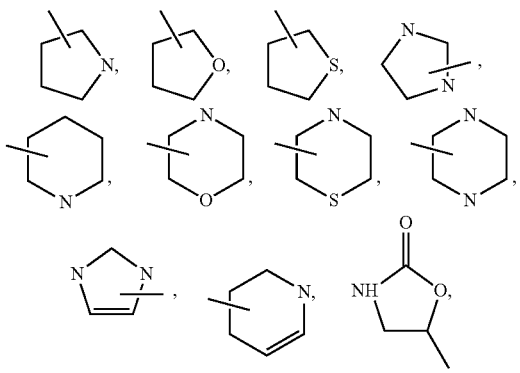

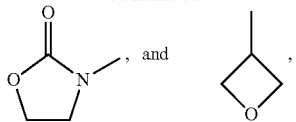

which optionally may be substituted.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are unsubstituted or substituted with 1 to 3 groups selected from OH, OC$_1$-C$_3$ alkoxy, Cl, F, Br, I, CN, NO$_2$, NH$_2$, N(CH$_3$)H, N(CH$_3$)$_2$, CF$_3$, OCF$_3$, OCHF$_2$, =O, C(=O)CH$_3$, SCH$_3$, S(=O)CH$_3$, S(=O)$_2$CH$_3$, C$_1$-C$_3$ alkyl, CO$_2$H and CO$_2$CH$_3$. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2). Bridged rings are also included in the definition of heteroaryl. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

Preferred heteroaryl groups include:

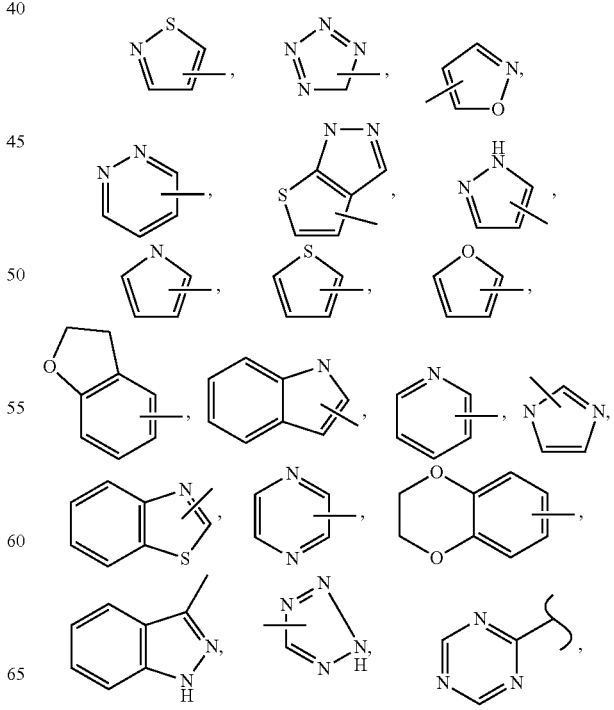

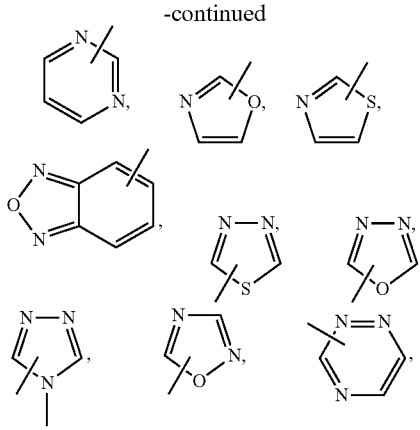

and the like.

The designation "∿" or

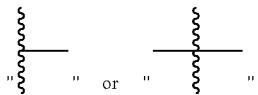

attached to a ring or other group refers to a free bond or linking group.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative. In cases in which there are quaternary carbon atoms in compounds of the present invention, these can be replaced by silicon atoms, provided they do not form Si—N or Si—O bonds.

When any variable occurs more than one time in any constituent or formula for a compound, its definition at each occurrence is independent of its definition at every other occurrence. Thus, for example, if a group is shown to be substituted with 0 to 3 $R^{10}$, then said group may optionally be substituted with up to three $R^{10}$ groups, and at each occurrence $R^{10}$ is selected independently from the definition of $R^{10}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, 22$^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Preparation of prodrugs is well known in the art and described in, for example, King, F. D., ed., *Medicinal Chemistry: Principles and Practice*, The Royal Society of Chemistry, Cambridge, UK (2$^{nd}$ edition, reproduced, 2006);

Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

Isotopically labeled compounds of the present invention, i.e., wherein one or more of the atoms described are replaced by an isotope of that atom (e.g., $^{12}$C replaced by $^{13}$C or by $^{14}$C; and isotopes of hydrogen including tritium and deuterium), are also provided herein. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 98%, preferably 99%, compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: AcOH=acetic acid; Ala=alanine; Atm=atmosphere; ACN=acetonitrile; Boc=t-butoxycarbonyl; BOP-Cl=bis(2-oxo-3-oxazolidinyl)phosphinic chloride; t-Bu=tert-butyl; Cbz=carboxybenzyl; d=day; DCM=dichloromethane; DIEA=DIPEA=N,N-diisopropylethylamine; DMSO=dimethylsulfoxide; EDAC=1-ethyl-3-(3-dimethylaminopropyl)carbodiimide hydrochloride; EtOAc=ethyl acetate; FCC=flash column chromatography; Fmoc=fluorenylmethyloxycarbonyl; Glu=glutamic acid; h=hour; HOBt=1-hydroxybenzotriazole; HPLC=high pressure liquid chromatography; LCMS=liquid chromatography-mass spectrometry; Leu=leucine; min=minute; MeOH=methanol; MPLC=medium pressure liquid chromatography; NMR=nuclear magnetic resonance; Pd/C=palladium on carbon; PyBOP=benzotriazol-1-yloxy)tripyrrolidinophosphonium hexafluorophosphate; sat.=saturated; Ser=serine; SiO$_2$=silica gel; TEA=trimethylamine; TFA=trifluoroacetic acid; Tyr=tyrosine; and Z=Cbz=carboxybenzyl.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

During the chemical syntheses, various protecting groups may be employed and subsequently removed in order to generate the compounds of the present invention. Exemplary protecting groups and conditions for their removal are described in Greene's *Protecting Groups in Organic Synthesis* P. G. M. Nuts, T. W. Greene, Fourth Edition, Wiley, New York, 2006.

EXAMPLES

The following compounds of the invention have been prepared, isolated and characterized using the methods disclosed herein. They demonstrate a partial scope of the invention and are not meant to be limiting of the scope of the invention.

LCMS Analysis Methods:

Compounds were analyzed on an Acquity Ultra Performance Liquid Chromatography system employing an Acquity UPLC BEH C18, 1.7 µm, 2.1×50 mm column. Detection was via an Aquity Ultra Performance LC PDA detector and an Acquity SQD single quadrupole mass spectrometer using H$_2$O+0.1% formic acid (A) and ACN+0.1% formic acid (B) as eluents.

Method A—Gradient: 0-0.1 min—Isocratic—10% B; 0.1-1.3 min—Linear gradient 10%-90% B; 1.3-1.8 min—Isocratic 90% B; 1.8-1.9 min—Linear gradient—90%-10% B; 1.9-2.0 min—Isocratic—B. Flow rate: 0.6 mL/min.

Method B—Gradient: 0-0.1 min—Isocratic—40% B; 0.1-1.3 min—Linear gradient—5%-95% B; 1.3-1.8 min—Isocratic—95% B; 1.8-1.9 min—Linear gradient—60%-40% B; 1.9-2.0 min—Isocratic—40% B. Flow rate: 0.6 mL/min.

Method C—Gradient: 0-0.1 min—Isocratic—40% B; 0.1-1.0 min—Linear gradient 40%-99% B; 1.0-1.8 min—Isocratic 99% B; 1.8-1.9 min—Linear gradient—99%-40% B; 1.9-2.0 min—Isocratic—40% B. Flow rate: 0.6 mL/min.

HPLC Analysis Method:

Compounds were analyzed on a Waters Alliance 2695 High-Performance Liquid Chromatography system employing a SunFire C18, 5 µm, 4.6×100 mm column. Detection was via a Waters 996 PDA detector using H$_2$O+0.1% trifluoroacetic acid (A) and ACN+0.1% trifluoroacetic acid (B) as eluents.

Gradient: 0-7.0 min—Linear gradient 10%-100% B; 7.0-8.0 min—Isocratic 100% B; 8.0-8.3 min—Linear gradient—100%-10% B; 8.3-10.0 min—Isocratic—10% B. Flow rate: 1.5 mL/min.

NMR Spectroscopy:

$^1$H NMR Spectroscopy was performed on a Bruker 400 MHz Avance II FTNMR Spectrometer. All $^1$H NMR chemical shifts are reported in parts per million (ppm) and either referenced to the residual C—H signal from the deuterated solvent indicated or to tetramethylsilane.

Intermediate I.1

(R)-tert-butyl 4-amino-5-oxo-5-((4-(trifluoromethyl)benzyl)amino)pentanoate

Step 1: (R)-tert-butyl 4-(((benzyloxy)carbonyl)amino)-5-oxo-5-((4-(trifluoromethyl)benzyl)amino)pentanoate

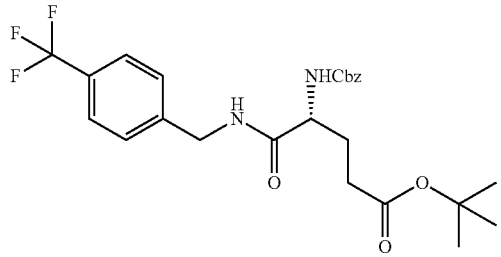 [SMILES: CC(C)(C)OC(=O)CC[C@@H](NC(=O)OCc1ccccc1)C(=O)NCc1ccc(C(F)(F)F)cc1]

To a mixture of Z-D-Glu-(Ot-Bu)-OH (1.00 g, 2.96 mmol) and 4-trifluoromethylbenzyl amine (0.42 mL, 3.0 mmol) in DCM (10 mL) was added EDAC (680 mg, 3.55 mmol) followed by HOBt H$_2$O (480 mg, 3.55 mmol). The resultant reaction mixture was stirred at ambient temperature for 16 h. The mixture was then concentrated in vacuo and the crude residue was taken up in EtOAc (100 mL). This was washed successively with sat. NaHSO$_4$ (aq) (1×50 mL), sat. NaHCO$_3$ (aq) (1×50 mL) and brine (1×50 mL). The organic layer was then dried (Na$_2$SO$_4$), filtered and concentrated in vacuo to provide 1.39 g (95%) of (R)-tert-butyl 4-(((benzyloxy)carbonyl)amino)-5-oxo-5-((4-(trifluoromethyl)benzyl)amino)pentanoate which was used in the next step without further purification.

Step 2: (R)-tert-butyl 4-amino-5-oxo-5-((4-(trifluoromethyl)benzyl)amino)pentanoate (Intermediate I.1)

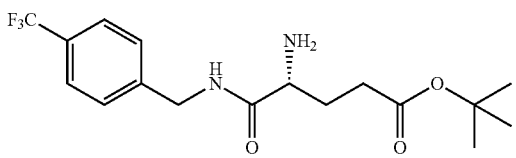 [SMILES: CC(C)(C)OC(=O)CC[C@@H](N)C(=O)NCc1ccc(C(F)(F)F)cc1]

A mixture of the crude product obtained in step 1 above (1.39 g, 2.81 mmol) and 10% Pd/C (100 mg) in MeOH (20 mL) was stirred vigorously under 1 atm of H$_2$ (g) (balloon) for 2.5 h. The mixture was then filtered through a pad of Celite rinsing with DCM and the filtrate was concentrated in vacuo to provide 1.01 g (100%) of Intermediate I.1. $^1$H NMR (400 MHz, CDCl$_3$): δ 7.73 (br t, 1H, N—H), 7.59 (d, 2H), 7.40 (d, 2H), 4.51 (d, 2H), 3.46 (dd, 1H), 2.44-2.31 (m, 2H), 2.20-2.12 (m, 1H), 1.89-1.80 (m, 1H), 1.44 (s, 9H) ppm; LCMS (Method A): t$_R$=0.94 min, m/z 361.3 (M+H)$^+$, 305.2 (M+H-C$_4$H$_8$)$^+$, 721.4 (2M+H)$^+$.

Intermediate I.2

(R)-2-amino-N-(3,4-dichlorobenzyl)-4-methylpentanamide

Step 1: (R)-tert-butyl (1-((3,4-dichlorobenzyl)amino)-4-methyl-1-oxopentan-2-yl)carbamate

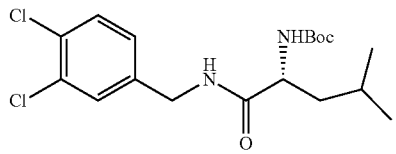 [SMILES: CC(C)C[C@@H](NC(=O)OC(C)(C)C)C(=O)NCc1ccc(Cl)c(Cl)c1]

Using the same general procedure as described in Step 1 for the preparation of Intermediate I.1, 3,4-dichlorobenzyl amine (1.14 g, 6.49 mmol) was reacted with Boc-D-Leu-OH (1.50 g, 6.49 mmol) to provide 1.94 g (77%) of (R)-tert-butyl (1-((3,4-dichlorobenzyl)amino)-4-methyl-1-oxopentan-2-yl)carbamate after purification by FCC (SiO$_2$, elution with 40% EtOAc/hexanes). $^1$H NMR (400 MHz, CDCl$_3$): δ 7.37 (d, 1H), 7.34 (d, 1H), 7.09 (dd, 1H), 6.70 (br t, 1H), 4.86 (br d, 1H), 4.38 (m, 2H), 4.11 (m, 1H), 1.74-1.66 (m, 2H), 1.52-1.47 (m, 1H), 1.42 (s, 9H), 0.95 (d, 3H), 0.93 (d, 2H) ppm; LCMS (Method A): t$_R$=1.41 min, m/z 389.3/391.3 (M+H)$^+$.

Step 2: (R)-2-amino-N-(3,4-dichlorobenzyl)-4-methylpentanamide (Intermediate I.2)

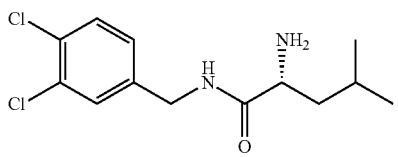 [SMILES: CC(C)C[C@@H](N)C(=O)NCc1ccc(Cl)c(Cl)c1]

To a mixture of the intermediate obtained in step 1 above (1.94 g, 5.00 mmol) in DCM (15 mL) was added dropwise TFA (15 mL). The reaction mixture was stirred at ambient temperature for 2 h, then quenched with 2M NaOH to bring the pH to ~9 and extracted with DCM (2×50 mL). The combined organic layers were washed with sat. NaHCO$_3$ (aq) (1×50 mL), brine (1×50 mL), dried (Na$_2$SO$_4$) and then filtered to provide 1.30 g (90%) of Intermediate I.2 after purification by FCC (SiO$_2$, elution with 0-10% MeOH/DCM). $^1$H NMR (400 MHz, CDCl$_3$): δ 7.79 (br t, 1H, N—H), 7.39 (d, 1H), 7.36 (d, 1H), 7.12 (dd, 1H), 4.39 (d, 2H), 3.45 (dd, 1H), 1.80-1.69 (m, 2H), 1.42-1.31 (m, 1H), 0.97 (d, 3H), 0.94 (d, 3H) ppm; LCMS (Method A): t$_R$=0.88 min, m/z 289.2/291.2 (M+H)$^+$.

Intermediate I.3

(R)-2-amino-3-(tert-butoxy)-N-(3,4-dichlorobenzyl) propanamide

Step 1: (R)-(9H-fluoren-9-yl)methyl(3-(tert-butoxy)-1-((3,4-dichlorobenzyl)amino)-1-oxopropan-2-yl)carbamate

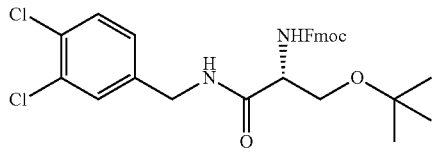

Using the same general procedure as described in Step 1 for the preparation of Intermediate I.1, 3,4-dichlorobenzyl amine (173 μL, 1.30 mmol) was reacted with Fmoc-D-Ser (t-Bu)OH (0.50 g, 1.3 mmol) to provide 0.64 g (91%) of (R)-(9H-fluoren-9-yl)methyl (3-(tert-butoxy)-1-((3,4-dichlorobenzyl)amino)-1-oxopropan-2-yl)carbamate after purification by FCC (SiO$_2$, elution with 0-100% EtOAc/hexanes). $^1$H NMR (400 MHz, d$_6$-DMSO): δ 8.55 (t, 1H), 7.89 (d, 2H), 7.74 (br d, 2H), 7.54 (d, 1H), 7.50 (d, 1H), 7.45-7.40 (m, 3H), 7.31 (td, 2H), 7.26 (dd, 1H), 4.37-4.20 (m, 5H), 4.12 (m, 1H), 3.50 (m, 2H), 1.11 (s, 9H) ppm; LCMS (Method B): t$_R$=1.36 min, m/z 541.3/543.4 (M+H)$^+$.

Step 2: (R)-2-amino-3-(tert-butoxy)-N-(3,4-dichlorobenzyl)propanamide (Intermediate I.3)

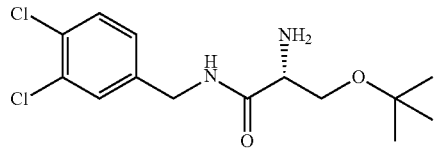 [SMILES: CC(C)(C)OC[C@@H](N)C(=O)NCc1ccc(Cl)c(Cl)c1]

To a solution of (R)-(9H-fluoren-9-yl)methyl (3-(tert-butoxy)-1-((3,4-dichlorobenzyl)amino)-1-oxopropan-2-yl)carbamate (0.64 g, 1.18 mmol) in DCM (12 mL) was added diethylamine (2.50 mL, 23.7 mmol) and the reaction mixture was then stirred at ambient temperature for 4 h. This was then concentrated in vacuo and the crude residue was purified by FCC (SiO$_2$, elution with 0-10% MeOH/DCM) to provide 0.38 g (99%) of Intermediate I.3. $^1$H NMR (400 MHz, d$_6$-DMSO): δ 8.46 (br t, 1H, N—H), 7.55 (d, 1H), 7.49 (d, 1H), 7.26 (dd, 1H), 4.28 (m, 2H), 3.39 (m, 2H), 3.27 (t, 1H), 1.81 (br s, 2H, NH2), 1.11 (s, 9H) ppm; LCMS (Method A): t$_R$=0.92 min, m/z 319.3/321.3 (M+H)$^+$.

Following the methods described above for the preparation of Intermediates I.1-I.3, and substituting the corresponding reagents, the following intermediates were prepared as indicated in Table 1.

TABLE 1

| Intermediate | Structure | Reagents | LCMS Method | t$_R$ (min) | (M + H)$^+$ observed |
|---|---|---|---|---|---|
| I.4 | 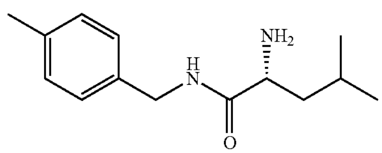 [SMILES: Cc1ccc(CNC(=O)[C@H](N)CC(C)C)cc1] | 4-methylbenzyl amine and Boc-D-Leu-OH | A | 0.75 | 235.3 |
| I.5 | 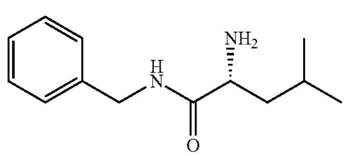 [SMILES: CC(C)C[C@@H](N)C(=O)NCc1ccccc1] | Benzylamine and Boc-D-Leu-OH | A | 0.70 | 221.3 |
| I.6 | 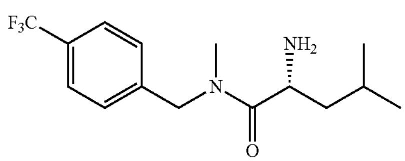 [SMILES: CC(C)C[C@@H](N)C(=O)N(C)Cc1ccc(C(F)(F)F)cc1] | N-methyl-4-trifluoromethyl-benzylamine and Boc-D-Leu-OH | A | 0.89 | 303.3 |
| I.7 | 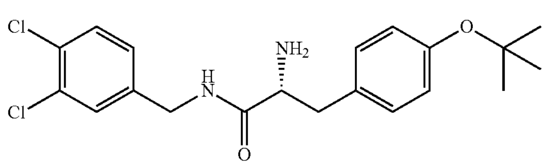 [SMILES: CC(C)(C)Oc1ccc(C[C@@H](N)C(=O)NCc2ccc(Cl)c(Cl)c2)cc1] | 3,4-dichlorobenzyl amine and Fmoc-D-Tyr(t-Bu)OH | A | 1.06 | 395.3/397.3 |
| I.8 | 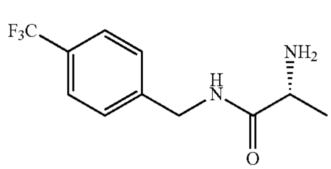 [SMILES: C[C@@H](N)C(=O)NCc1ccc(C(F)(F)F)cc1] | 4-(trifluoromethyl)benzyl amine and Boc-D-Ala-OH | A | 0.74 | 247.3 |

TABLE 1-continued

| Intermediate | Structure | Reagents | LCMS Method | $t_R$ (min) | $(M + H)^+$ observed |
|---|---|---|---|---|---|
| I.9 | 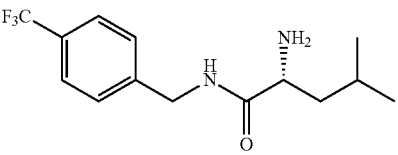 [SMILES: CC(C)C[C@@H](N)C(=O)NCc1ccc(C(F)(F)F)cc1] | 4-(trifluoromethyl)benzyl amine and Boc-D-Leu-OH | A | 0.84 | 289.3 |
| I.10 | 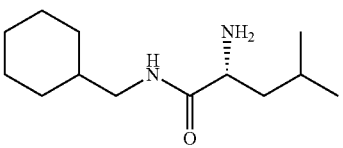 [SMILES: CC(C)C[C@@H](N)C(=O)NCC1CCCCC1] | Cyclohexylmethyl amine and Boc-D-Leu-OH | A | 0.80 | 227.3 |
| I.11 | 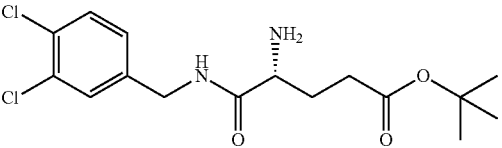 [SMILES: CC(C)(C)OC(=O)CC[C@@H](N)C(=O)NCc1ccc(Cl)c(Cl)c1] | 3,4-dichlorobenzyl amine and Cbz-D-Glu-(Ot-Bu)-OH | A | 0.97 | 361.3/363.3 |
| I.12 | 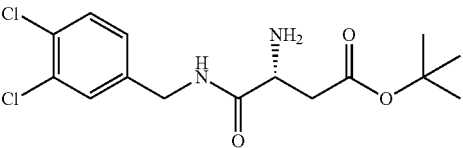 [SMILES: CC(C)(C)OC(=O)C[C@@H](N)C(=O)NCc1ccc(Cl)c(Cl)c1] | 3,4-dichlorobenzyl amine and Cbz-D-Asp-(Ot-Bu)-OH | A | 0.92 | 347.2/349.2 |
| I.13 | 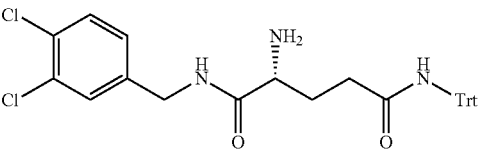 | 3,4-dichlorobenzyl amine and Fmoc-D-Glu-(Trt)-OH | A | 1.22 | 546.3/548.3 |

Intermediate II.1

5-phenylpent-1-en-3-one

Step 1: N-methoxy-N-methyl-3-phenylpropanamide

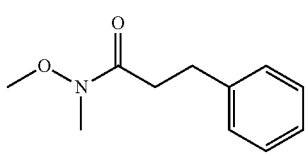

To a solution of 3-phenylpropionic acid (1.00 g, 6.66 mmol) in DCM (20 mL) was added PyBOP (3.47 g, 6.66 mmol) followed by TEA (1.1 mL, 7.6 mmol). The resultant mixture was stirred at ambient temperature for 30 min. This was then cooled to 0° C. and N,O-dimethylhydroxyl amine.HCl (0.72 g, 7.33 mmol) was added followed by additional TEA (1.1 mL, 7.6 mmol). The reaction mixture was warmed to room temperature and stirred for 16 h. This was then concentrated in vacuo and the crude residue was purified by FCC (SiO₂, elution with 0-100% EtOAc/hexanes) to provide 1.21 g (94%) of N-methoxy-N-methyl-3-phenylpropanamide. ¹H NMR (400 MHz, CDCl₃): δ 7.32-7.18 (m, 5H), 3.61 (s, 3H), 3.18 (s, 3H), 2.97 (t, 2H), 2.75 (t, 2H) ppm; LCMS (Method A): $t_R$=1.04 min, m/z 194.4 (M+H)⁺.

Step 2: 5-phenylpent-1-en-3-one (Intermediate II.1)

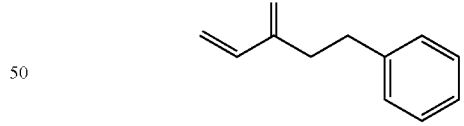

To a solution of the Weinreb amide obtained in step 1 above (0.20 g, 1.04 mmol) in anhydrous Et₂O (5 mL) at 0° C. was added vinyl magnesium bromide (1.0 M in THF, 1.25 mL, 1.25 mmol). The reaction mixture was stirred at 0° C. for 30 min then allowed to warm to room temperature and was stirred an additional 2.5 h. The reaction mixture was then cooled to 0° C. and additional vinyl magnesium bromide (1.0 M in THF, 0.40 mL, 0.40 mmol) was added. The resultant mixture was warmed to room temperature and stirred an additional 1 h. The reaction mixture was then quenched with 2 N HCl (aq) and extracted with EtOAc (3×). The combined organic extracts were dried (Na₂SO₄), filtered and concentrated in vacuo. The crude residue was then taken up in DCM and filtered through a 1 gram cartridge of SiO₂, eluting with additional DCM. The filtrate was concentrated in vacuo to provide 0.13 g (78%) of Intermediate II.1. $^1$H NMR (400 MHz, CDCl$_3$): δ 7.31-7.19 (m, 5H), 6.37 (dd, 1H), 6.22 (dd, 1H), 5.84 (dd, 1H), 2.99-2.89 (m, 4H) ppm.

Using the synthetic method outlined above for the preparation of Intermediate II.1 the following intermediates were made from the corresponding reagent as indicated in Table 2.

stirred at ambient temperature for 16 h. The mixture was then concentrated in vacuo and the crude residue purified by FCC (SiO$_2$, elution with 0-10% MeOH/DCM) to provide 297 mg (88%) of Compound 1-1 as a clear oil. $^1$H NMR (400 MHz, CDCl$_3$): δ 7.88 (br t, 1H, amide N—H), 7.40 (d, 1H), 7.38 (d, 1H), 7.29-7.25 (m partially obscured by solvent peak, 2H), 7.21-7.43 (m, 4H), 4.40 (m, 2H), 3.10

TABLE 2

| Intermediate | Structure | Reagent | $^1$H NMR |
| --- | --- | --- | --- |
| II.2 | 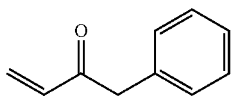 | Phenylacetic acid | (400 MHz,CDCl$_3$): δ 7.36-7.21 (m, 5H), 6.42 (dd, 1H), 6.32 (dd, 1H), 6.84 (dd, 1H), 3.89 (s, 2H) ppm |
| II.3 | 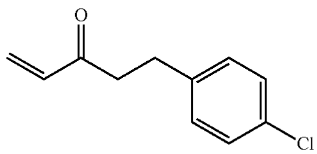 | 4-Chloro-phenylpropionic acid | (400 MHz, CDCl$_3$): δ 7.25 (d, 2H), 7.13 (d, 2H), 6.35 (dd, 1H), 6.21 (dd, 1H), 5.84 (dd, 1H), 2.95-2.87 (m, 4H) ppm |

Example 1

(2R)-2-((8R,9aS)-8-amino-1-oxo-5-phenethylhexahydro-1H-pyrrolo[1,2-a][1,4]diazepin-2(3H)-yl)-N-(3,4-dichlorobenzyl)-4-methylpentanamide.HCl Step 1: (R)—N-(3,4-dichlorobenzyl)-4-methyl-2-((3-oxo-5-phenylpentyl)amino)pentanamide (Compound 1-1)

(dd, 1H), 2.89 (app t, 2H), 2.81-2.67 (m, 4H), 2.53 (m, 2H), 1.71-1.24 (m, 4H including amine N—H), 0.95 (d, 3H), 0.93 (d, 3H) ppm.

Step 2: (2S,4R)-(9H-fluoren-9-yl)methyl 4-((tert-butoxycarbonyl)amino)-2-(((R)-1-((3,4-dichlorobenzyl)amino)-4-methyl-1-oxopentan-2-yl)(3-oxo-5-phenylpentyl)carbamoyl)pyrrolidine-1-carboxylate (Compound 1-2)

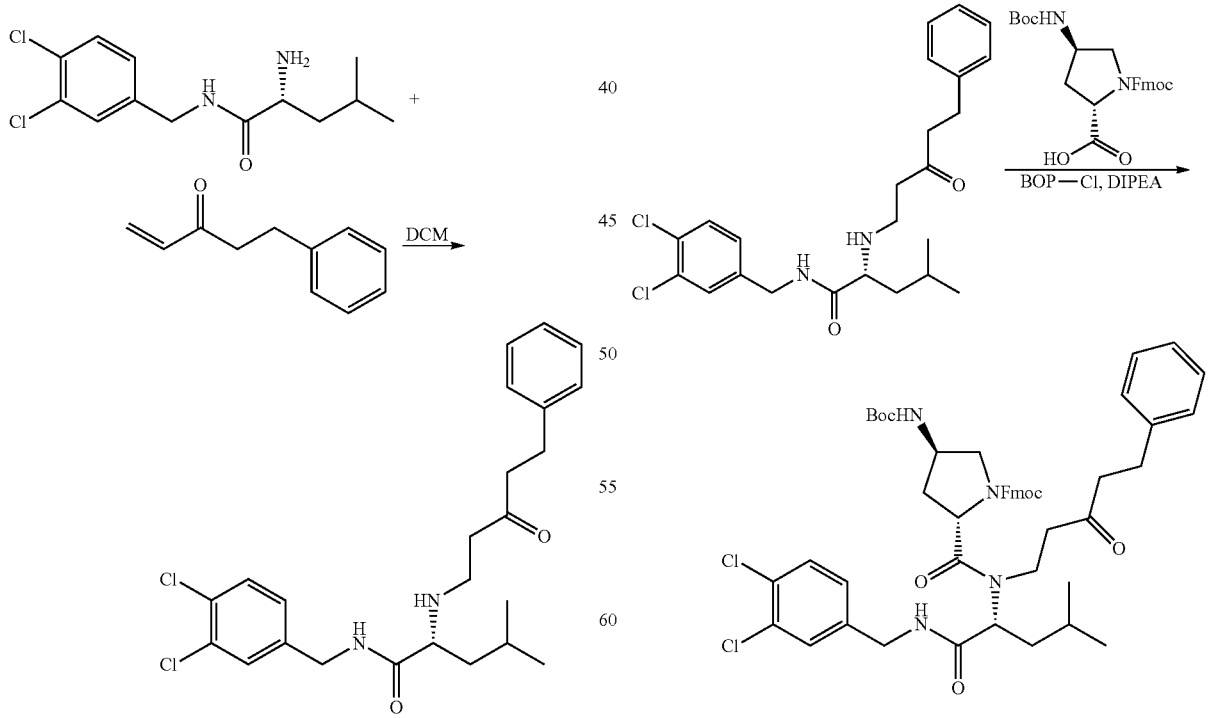

A mixture of Intermediate I.2 (218 mg, 0.755 mmol) and Intermediate II.1 (121 mg, 0.755 mmol) in DCM (5 mL) was To a solution of (2S,4R)-Boc-4-amino-Fmoc proline (330 mg, 0.729 mmol) in DCM (2 mL) was added DIPEA (0.35 mL, 2.0 mmol). This mixture was then added via pipette to a reaction vial containing Compound 1-1 (297 mg, 0.662 mmol). The vessel originally containing the proline reagent and DIPEA mixture was rinsed with DCM (1 mL) and this was also added via pipette to the reaction vial. BOP-Cl (96 mg, 0.38 mmol) was then added and the resultant reaction mixture was stirred at ambient temperature for 3 d. The reaction mixture was quenched with sat. NaHCO₃ (aq) and extracted with DCM (3×). The combined organic extracts were dried (Na₂SO₄), filtered and concentrated in vacuo. The crude residue was purified by FCC (SiO₂, elution with 0-50% EtOAc/hexanes) to provide 449 mg (77%) of Compound 1-2 as an off-white solid. LCMS (Method A): $t_R$=1.83 min, m/z 883.6/885.6 (M+H)⁺.

Steps 3 and 4: tert-butyl ((8R,9aS)-2-((R)-1-((3,4-dichlorobenzyl)amino)-4-methyl-1-oxopentan-2-yl)-1-oxo-5-phenethyloctahydro-1H-pyrrolo[1,2-a][1,4]diazepin-8-yl)carbamate (Compound 1-3)

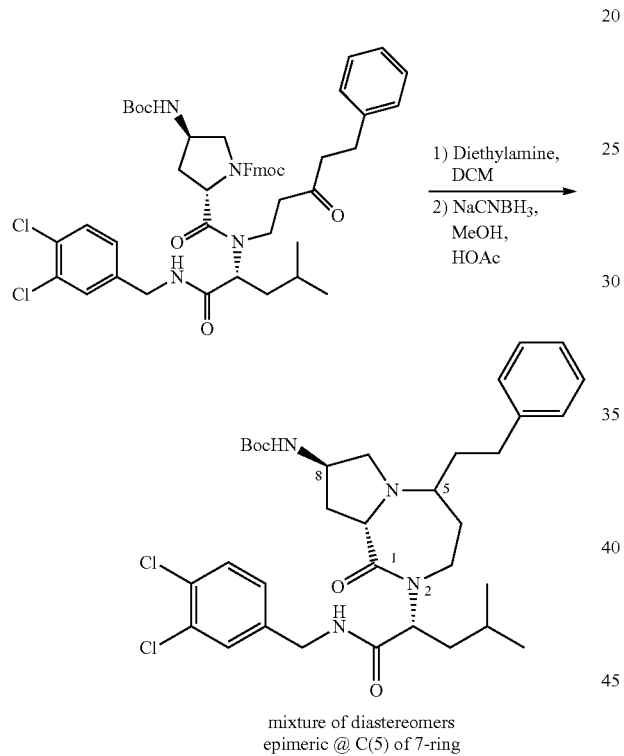

mixture of diastereomers
epimeric @ C(5) of 7-ring

To a solution of Compound 1-2 (445 mg; 0.503 mmol) in DCM (5 mL) was added dimethylamine (1.00 mL, 10.1 mmol) and this was stirred for 3 h at ambient temperature. This mixture was then concentrated in vacuo and the crude residue was taken up in MeOH (5 mL) and to this was added AcOH (0.10 mL) followed by NaCNBH₃ (1 M in THF, 0.65 mL, 0.65 mmol). The reaction mixture was stirred for 45 min. The mixture was then quenched with sat. NaHCO₃ (aq) and extracted with DCM (3×). The combined organic extracts were dried (Na₂SO₄), filtered and concentrated in vacuo. The crude residue was purified by FCC (SiO₂, elution with 0-50% EtOAc/hexanes) to provide 255 mg (78%) of Compound 1-3 as white solid. Analysis by LCMS indicated Compound 1-3 to be a mixture of two diastereomers in a ratio of 88:12. This mixture was carried directly into the next step. LCMS (Method A): $t_R$=1.38 min (major diastereomer, 88%) and 1.45 min (minor diastereomer, 12%), m/z 645.5/647.5 (M+H)⁺.

Step 5: Example 1

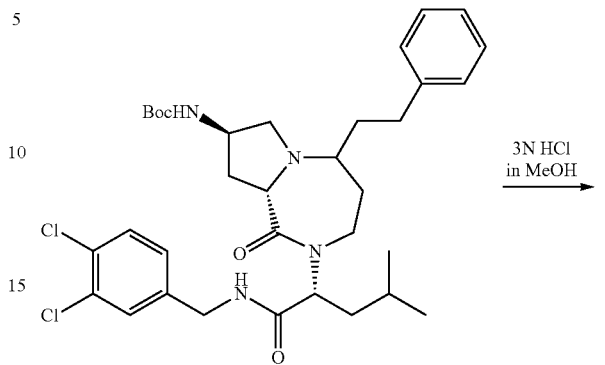

Compound 1-3 (255 mg, 0.395 mmol) was taken up in 3N HCl in MeOH (2 mL) and stirred at 40° C. in a tightly capped reaction vial for 2 h. The reaction temperature was increased to 50° C. and stirring was continued for 30 min. The reaction mixture was then cooled, concentrated in vacuo and the crude residue was purified directly by mass-directed, preparative reverse phase HPLC (C18 column, elution with 5-95% ACN/H₂O containing 0.25% formic acid). The desired fractions containing mainly the desired first eluting (major) diastereomer and a small amount of second eluting (minor) diastereomer were combined and partially concentrated in vacuo. To this was added 3N HCl (~10 mL) and the volatiles were removed in vacuo. This treatment with 3N HCl was repeated to ensure formation of the hydrochloride salt. The mixture was then concentrated in vacuo and the residue was taken up in H₂O and a small amount of ACN was added to provide a clear solution which was lyophilized to provide 96 mg (42%) of Example 1 as an off-white solid. Analysis by HPLC indicated Example 1 to be a mixture of diastereomers in a ratio of 96:4. ¹H NMR (400 MHz, CD₃OD): δ 7.52 (d, 1H), 7.47 (d, 1H), 7.32-7.19 (m, 6H), 5.22 (dd, 1H), 5.04 (m, 1H), 4.35 (ABq, 2H), 4.15 (m, 1H), 3.96 (m, 1H), 3.85-3.62 (m, 3H), 3.37 (m, 1H), 3.20 (m, 1H), 2.77 (m, 1H), 2.59 (m, 1H), 2.38-2.26 (m, 2H), 2.16 (m, 1H), 1.98-1.66 (m, 4H), 1.50 (m, 1H), 0.98 (d, 3H), 0.92 (d, 3H) ppm; LCMS (Method A): $t_R$=1.17 min, m/z 545.4/547.4 (M+H)⁺; HPLC: $t_R$=4.866 min (96%, major diastereomer) and 5.207 min (4%, minor diastereomer).

Example 2
(4R)-4-((8R,9aS)-8-amino-1-oxo-5-phenethylhexahydro-1H-pyrrolo[1,2-a][1,4]diazepin-2(3H)-yl)-5-oxo-5-((4-(trifluoromethyl)benzyl)amino)pentanoic Acid
Steps 1-4: (4R)-tert-butyl 4-((8R,9aS)-8-((tert-butoxycarbonyl)amino)-1-oxo-5-phenethylhexahydro-1H-pyrrolo[1,2-a][1,4]diazepin-2(3H)-yl)-5-oxo-5-((4-(trifluoromethyl)benzyl)amino)pentanoate (Compound 2-3)
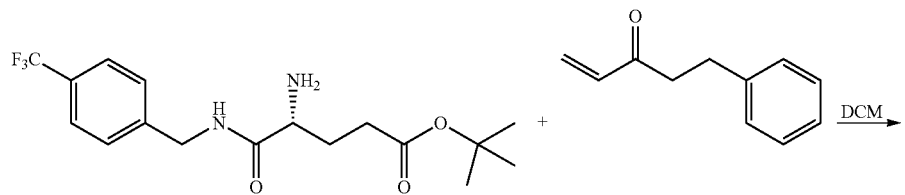
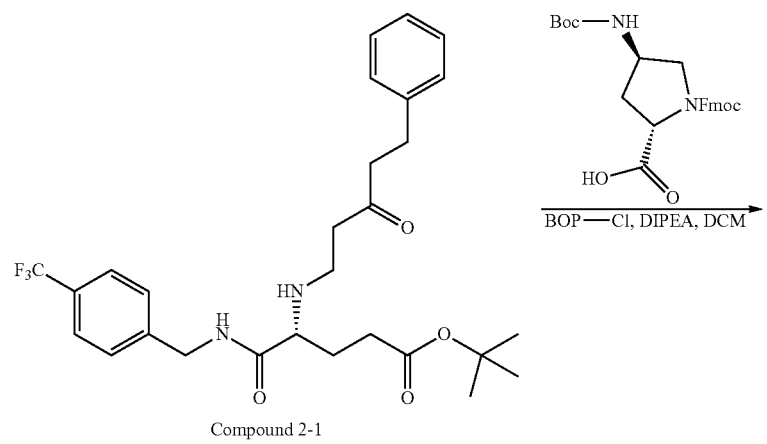
Compound 2-1
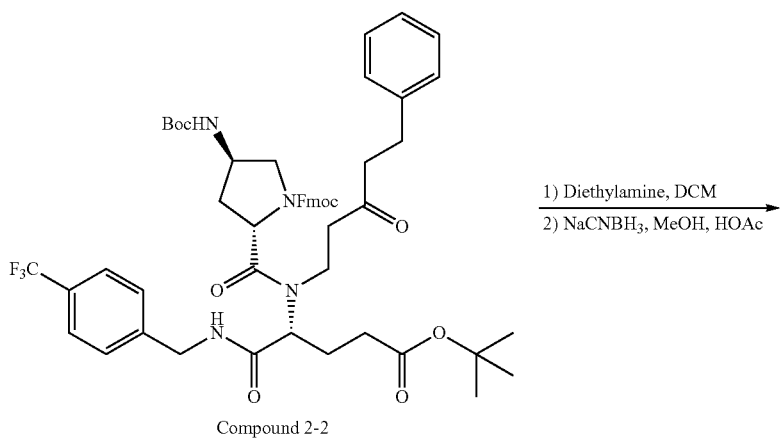
Compound 2-2

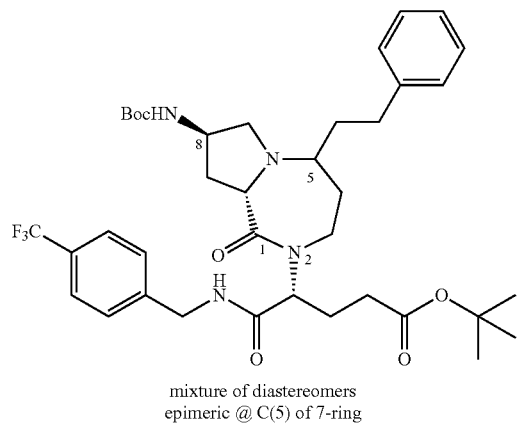

mixture of diastereomers
epimeric @ C(5) of 7-ring

Compound 2-3 was prepared from Intermediate I.1 (254 mg, 0.705 mmol) and Intermediate II.1 (113 mg, 0.705 mmol) using the same general procedures described for the preparation of Compound 1-3 in steps 1-4 in Example 1. After work up the crude product was purified by FCC (SiO$_2$, elution with 0-100% EtOAc/hexanes) to provide 56 mg of a first eluting, minor diastereomer (Compound 2-3A) and 124 mg of a second eluting, major diasteromer (Compound 2-3B). The pure minor diastereomer 2-3A and pure major diastereomer 2-3B were carried independently into the next step. Data for Compound 2-3A (minor diastereomer): LCMS (Method A): $t_R$=1.41 min, m/z 717.6 (M+H)$^+$. Data for Compound 2-3B (major diastereomer): $^1$H NMR (400 MHz, CD$_3$OD): δ 7.61 (d, 2H), 7.51 (d, 2H), 7.25 (m, 2H), 7.15 (m, 3H), 5.13 (dd, 1H), 4.46 (ABq, 2H), 4.00 (m, 1H), 3.71 (dd, 1H), 3.56 (dd, 1H), 3.46-3.40 (m, 2H), 2.81 (m, 1H), 2.63-2.53 (m, 2H), 2.42 (m, 1H), 2.29-2.13 (m, 5H), 1.96-1.82 (m, 3H), 1.71 (m, 1H), 1.55 (m partially obscured by singlet, 1H), 1.44 (s superimposed on multiplet, 18H), ppm; LCMS (Method A): $t_R$=1.33 min, m/z 717.6 (M+H)$^+$.

Step 5A: (4R)-4-((8R,9aS)-8-amino-1-oxo-5-phenethylhexahydro-1H-pyrrolo[1,2-a][1,4]diazepin-2(3H)-yl)-5-oxo-5-((4-(trifluoromethyl)benzyl)amino)pentanoic Acid (Example 2A)

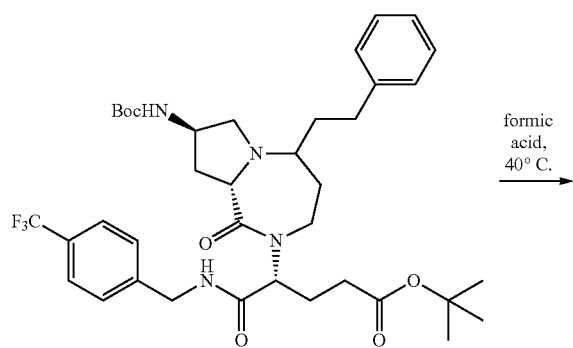

formic acid, 40° C.

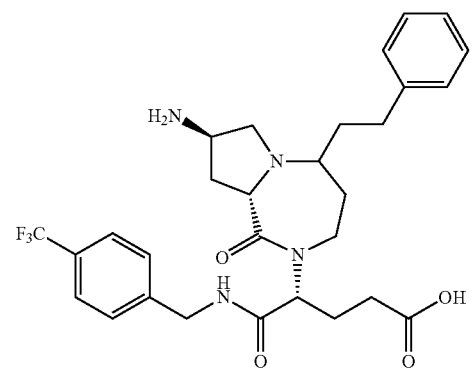

A solution of Compound 2-3A (55 mg, 0.077 mmol) in formic acid (2 mL) was heated to 40° C. for 2 h. The reaction mixture was then concentrated in vacuo and the crude residue was taken up in 1:1 ACN/H$_2$O (2 mL) and then purified directly by mass-directed preparative reverse phase HPLC (C-18, elution with 5-95% ACN/H$_2$O containing 0.25% formic acid). The desired fractions containing purified product were combined, diluted with H$_2$O, and lyophilized to provide 36 mg (84%) of Example 2A as a white solid. $^1$H NMR (400 MHz, CD$_3$OD): δ 7.62 (d, 2H), 7.47 (d, 2H), 7.27-7.13 (m, 5H), 5.14 (dd, 1H), 4.46 (s, 2H), 3.81-3.73 (m, 2H), 3.67 (dd, 1H), 3.51 (dd, 1H), 3.34 (m partially obscured by solvent peak, 1H), 2.78-2.57 (m, 5H), 2.42-2.27 (m, 4H), 2.07-1.88 (m, 3H), 1.82-1.71 (m, 2H), ppm; LCMS (Method A): $t_R$=1.00 min, m/z 561.5 (M+H)$^+$.

Step 5B: (4R)-4-((8R,9aS)-8-amino-1-oxo-5-phenethylhexahydro-1H-pyrrolo[1,2-a][1,4]diazepin-2(3H)-yl)-5-oxo-5-((4-(trifluoromethyl)benzyl)amino)pentanoic Acid (Example 2B)

solid. $^1$H NMR (400 MHz, CD$_3$OD): δ 7.60 (d, 2H), 7.50 (d, 2H), 7.25 (m, 2H), 7.17-7.14 (m, 3H), 5.09 (m, 1H), 4.46 (ABq, 2H), 3.82 (dd, 1H), 3.67-3.52 (m, 4H), 2.97 (m, 1H), 2.68-2.60 (m, 2H), 2.50 (m, 1H), 2.40 (app t, 1H), 2.20-2.03 (m, 4H), 1.97-1.82 (m, 3H), 1.67-1.55 (m, 2H) ppm; LCMS (Method A): t$_R$=0.95 min, m/z 561.5 (M+H)$^+$.

Example 3

(2R)-2-((8R,9aS)-8-amino-1-oxo-5-phenethylhexahydro-1H-pyrrolo[1,2-a][1,4]diazepin-2(3H)-yl)-N-(3,4-dichlorobenzyl)-3-hydroxypropanamide.HCl Steps 1-4: tert-butyl ((8R,9aS)-2-((R)-3-(tert-butoxy)-1-((3,4-dichlorobenzyl)amino)-1-oxopropan-2-yl)-1-oxo-5-phenethyloctahydro-1H-pyrrolo[1,2-a][1,4]diazepin-8-yl)carbamate (Compound 3-3)

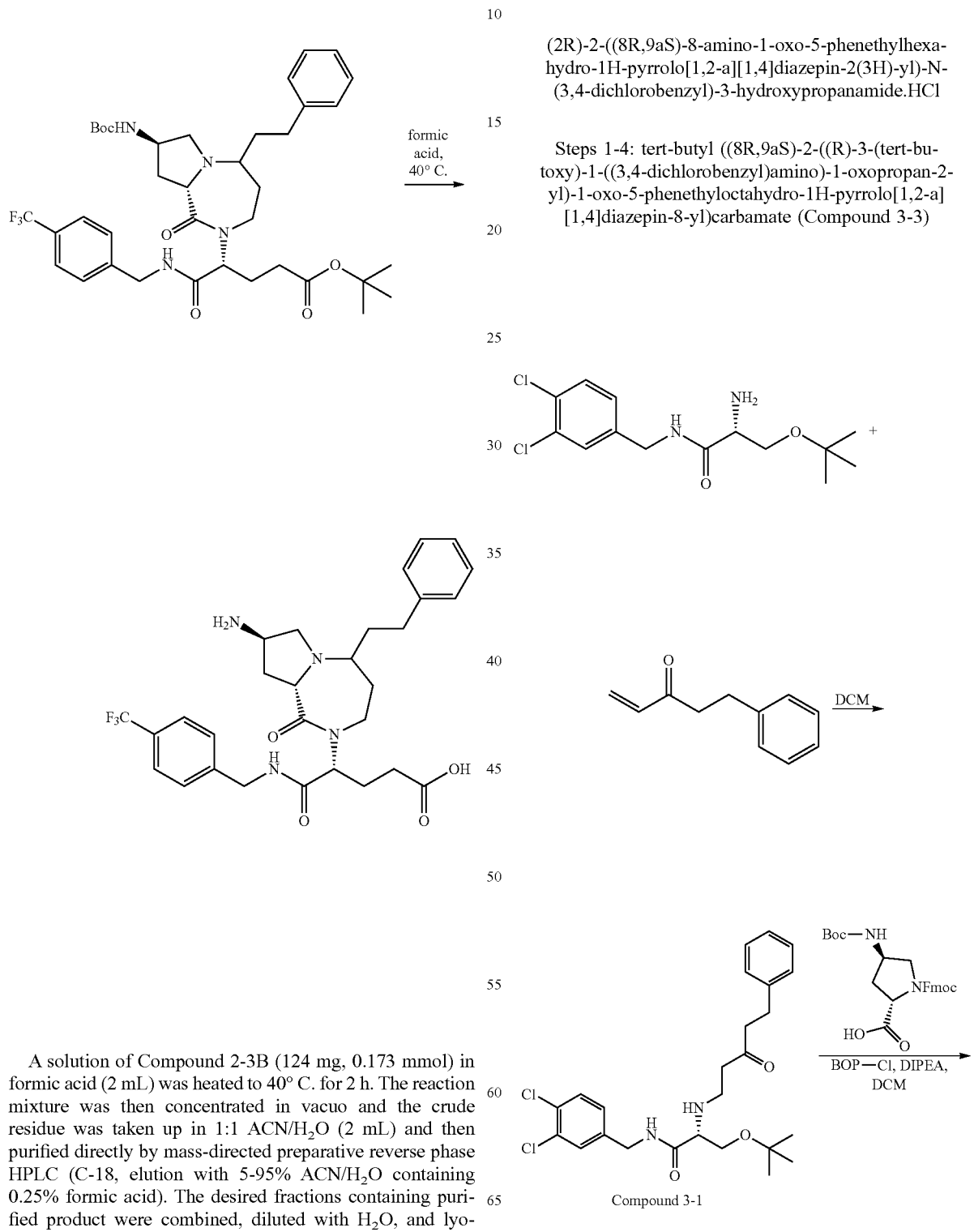

Compound 3-1

A solution of Compound 2-3B (124 mg, 0.173 mmol) in formic acid (2 mL) was heated to 40° C. for 2 h. The reaction mixture was then concentrated in vacuo and the crude residue was taken up in 1:1 ACN/H$_2$O (2 mL) and then purified directly by mass-directed preparative reverse phase HPLC (C-18, elution with 5-95% ACN/H$_2$O containing 0.25% formic acid). The desired fractions containing purified product were combined, diluted with H$_2$O, and lyophilized to provide 74 mg (76%) of Example 2B as a white Step 5: Example 3

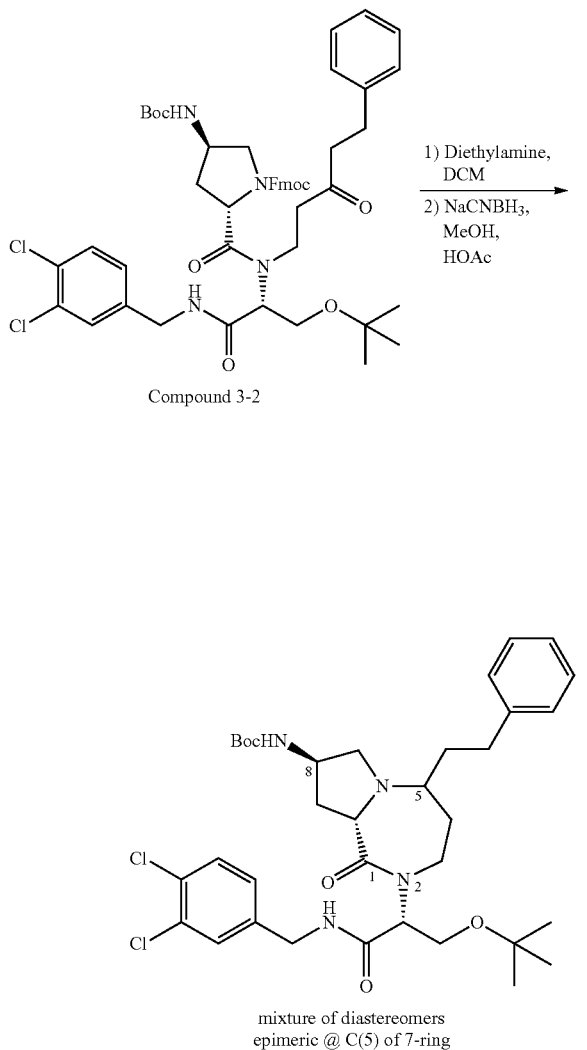

Compound 3-2

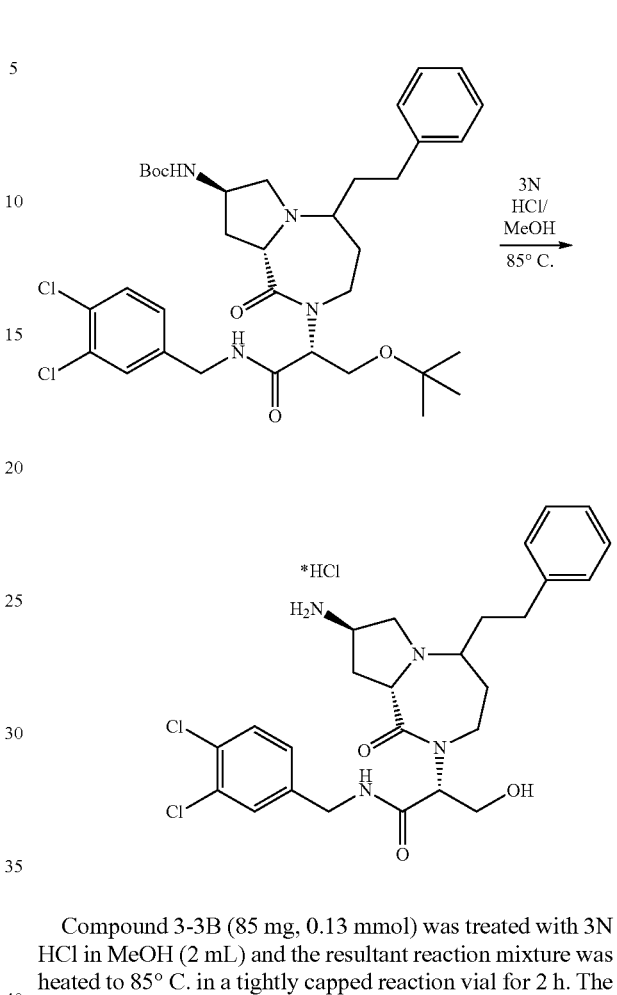

mixture of diastereomers
epimeric @ C(5) of 7-ring

Compound 3-3 was prepared from Intermediate I.3 (99 mg, 0.31 mmol) and Intermediate II.1 (50 mg, 0.31 mmol) using the same general procedures described for the preparation of Compound 1-3 in steps 1-4 in Example 1. After work up the crude product was purified by FCC (SiO$_2$, elution with 0-100% EtOAc/hexanes) to provide 17 mg (13%) of a first eluting, minor diastereomer (Compound 3-3A) and 91 mg (70%) of a second eluting, major diastereomer (Compound 3-3B). The pure major diastereomer 3-3B was carried into the next step. Data for Compound 3-3A (minor diastereomer): LCMS (Method A): $t_R$=0.90 min, m/z 675.4/677.3 (M+H)$^+$. Data for Compound 3-3B (major diastereomer): $^1$H NMR (400 MHz, CDCl$_3$): δ 7.39-7.36 (m, 2H), 7.28 (m partially obscured by solvent peak, 2H), 7.20-7.08 (m, 6H), 4.95 (app t, 1H), 4.49-4.29 (m, 3H), 4.09 (m, 1H), 3.82 (dd, 1H), 3.67-3.62 (m, 2H), 3.51-3.44 (m, 3H), 2.91-2.51 (m, 4H), 2.45 (m, 1H), 2.23 (m, 1H), 1.91-1.82 (m, 2H), 1.67 (m partially obscured by H$_2$O peak, 1H), 1.44 (s, 9H), 1.17 (s, 9H) ppm; LCMS (Method A): $t_R$=0.87 min, m/z 675.4/677.3 (M+H)$^+$.

Compound 3-3B (85 mg, 0.13 mmol) was treated with 3N HCl in MeOH (2 mL) and the resultant reaction mixture was heated to 85° C. in a tightly capped reaction vial for 2 h. The reaction mixture was then cooled and concentrated in vacuo. The crude residue was taken up in DMSO (1.5 mL) and then was purified directly by mass-directed preparative reverse phase HPLC (elution with 5-95% ACN/H$_2$O containing 0.25% formic acid). The desired fractions were combined and partially concentrated in vacuo. To this was added 3N HCl (~10 mL) and the volatiles were removed in vacuo. This treatment with 3N HCl was repeated to ensure formation of the hydrochloride salt. The mixture was then concentrated in vacuo and the residue was taken up in H$_2$O and a small amount of ACN was added to provide a clear solution which was lyophilized to provide 26 mg (38%) of Example 3 as a yellow solid. $^1$H NMR (400 MHz, CD$_3$OD): δ 7.53 (d, 1H), 7.46 (d, 1H), 7.32-7.19 (m, 6H), 5.07 (dd, 1H), 4.97 (m partially obscured by H$_2$O peak, 1H), 4.38 (ABq, 2H), 4.12 (m, 1H), 4.03-3.88 (m, 3H), 3.85-3.79 (m, 2H), 3.65 (m, 1H), 3.34 (m partially obscured by solvent peak, 1H), 3.20 (m, 1H), 2.77 (m, 1H), 2.60 (m, 1H), 2.36-2.25 (m, 2H), 2.17 (m, 1H), 2.05 (m, 1H), 1.87 (m, 1H) ppm; LCMS (Method A): $t_R$=0.97 min, m/z 519.4/521.4 (M+H)$^+$.

Following the methods described above for Examples 1-3, and substituting the corresponding intermediates, the following examples were prepared as indicated in Table 3. Unless indicated otherwise, the Examples in Table 3 were prepared from the major diastereomer obtained in step 4 (intramolecular reductive amination) of the synthesis.

TABLE 3

| Example | Structure | Intermediates and reagents | LCMS Method | $t_R$ (min) | $(M + H)^+$ observed |
|---|---|---|---|---|---|
| 4 | 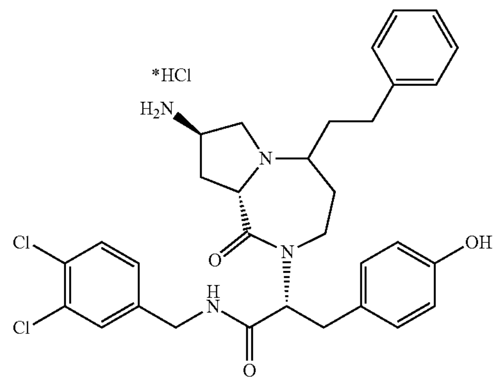 | I.7 and II.1 | A | 1.08 | 595.5/597.4 |
| 5 | 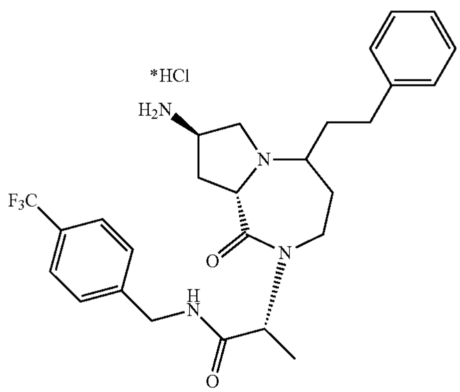 | I.8 and II.1 | A | 1.00 | 503.5 |
| 6 | 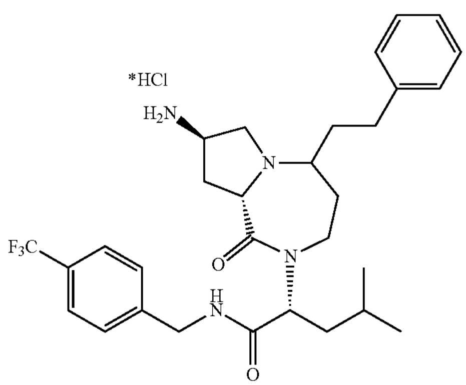 | I.9 and II.1 | A | 1.07 | 545.5 |
| 7 | 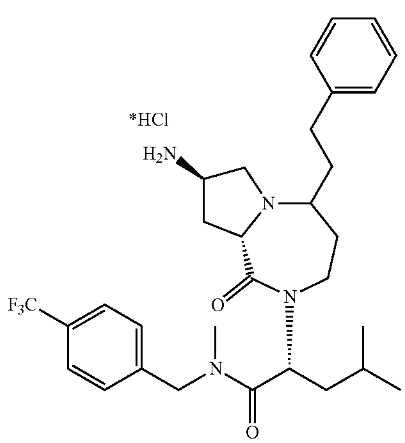 | I.6 and II.1 | A | 1.12 | 559.5 |

TABLE 3-continued

| Example | Structure | Intermediates and reagents | LCMS Method | $t_R$ (min) | $(M + H)^+$ observed |
|---|---|---|---|---|---|
| 8 | 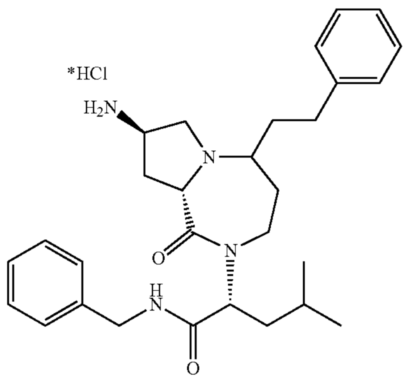 | I.5 and II.1 | A | 0.98 | 477.5 |
| 9 | 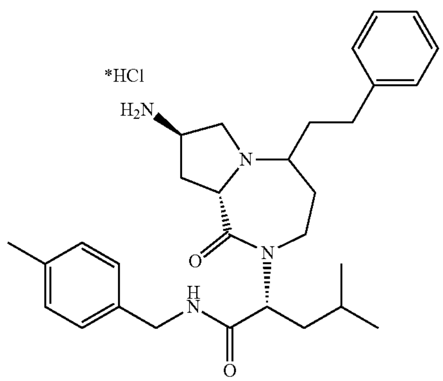 | I.4 and II.1 | A | 1.00 | 491.5 |
| 10 | 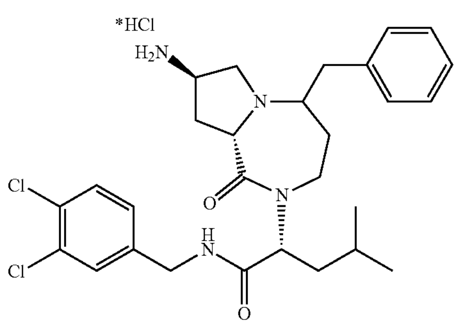 | I.2 and II.2 | A | 1.14 | 531.5/533.5 |
| 11 | 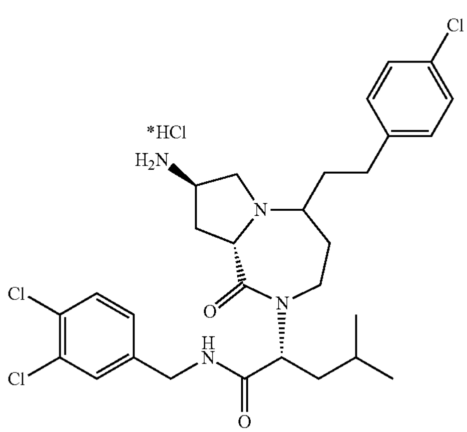 | I.2 and II.3 | A | 1.27 | 579.5/581.4/583.4 |

TABLE 3-continued
| Example | Structure | Intermediates and reagents | LCMS Method | $t_R$ (min) | $(M + H)^+$ observed |
|---|---|---|---|---|---|
| 12 | 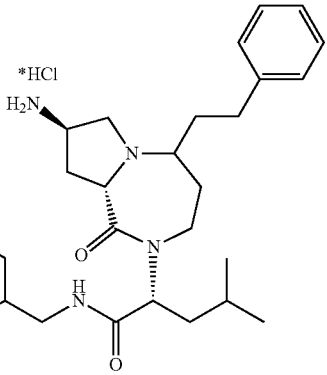 | I.10 and II.1 | A | 1.07 | 483.6 |
| 13 | 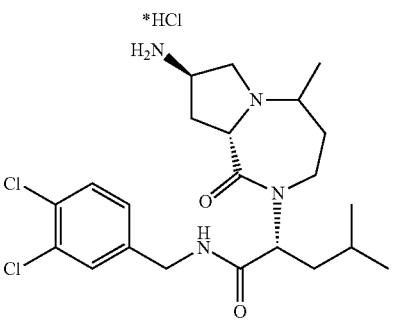 | I.2 and 3-buten-2-one | A | 0.96 | 455.4/457.4 |
| 14A | 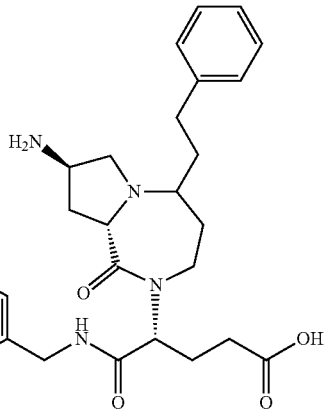 (minor diastereomer; diastereomer of 14B, epimeric @ C(5)) | I.11 and II.1 | A | 1.08 | 561.4/563.4 |

TABLE 3-continued
| Example | Structure | Intermediates and reagents | LCMS Method | $t_R$ (min) | $(M + H)^+$ observed |
|---|---|---|---|---|---|
| 14B | 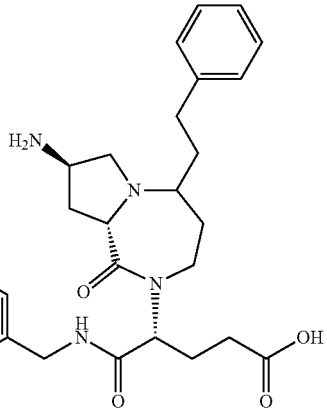<br>(minor diastereomer; diastereomer of 14A, epimeric @ C(5)) | I.11 and II.1 | A | 0.94 | 561.3/563.3 |
| 15 | 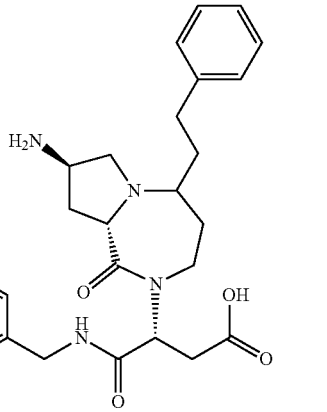 | I.12 and II.1 | A | 1.02 | 547.3/549.3 |
| 16 | 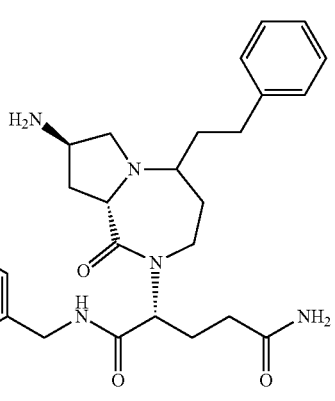 | I.13 and II.1 | A | 0.99 | 560.4/562.3 |

TABLE 3-continued

| Example | Structure | Intermediates and reagents | LCMS Method | $t_R$ (min) | $(M + H)^+$ observed |
|---|---|---|---|---|---|
| 17 | 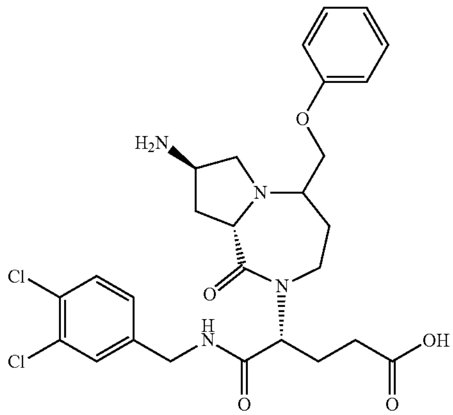 | I.11 and phenoxymethyl vinyl ketone | A | 0.96 | 563.5/565.5 |
| 18 | 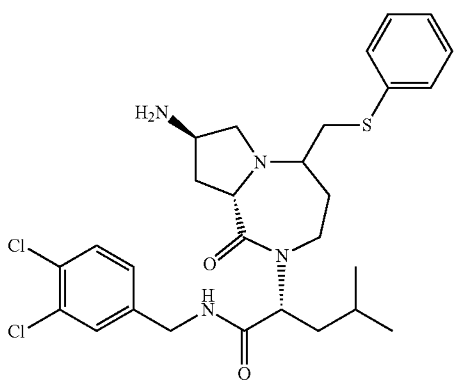 | I.2 and (phenylsulfanyl)methyl vinyl ketone | A | 1.15 | 563.5/565.5 |
| 19 | 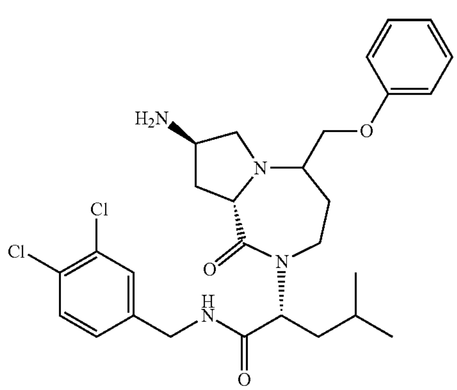 | I.2 and II.4 | A | 1.11 | 547.4/549.4 |

Example 20

(2R)-2-((8R,9aS)-8-acetamido-1-oxo-5-phenethyl-hexahydro-1H-pyrrolo[1,2-a][1,4]diazepin-2(3H)-yl)-N-(3,4-dichlorobenzyl)-4-methylpentanamide HCl

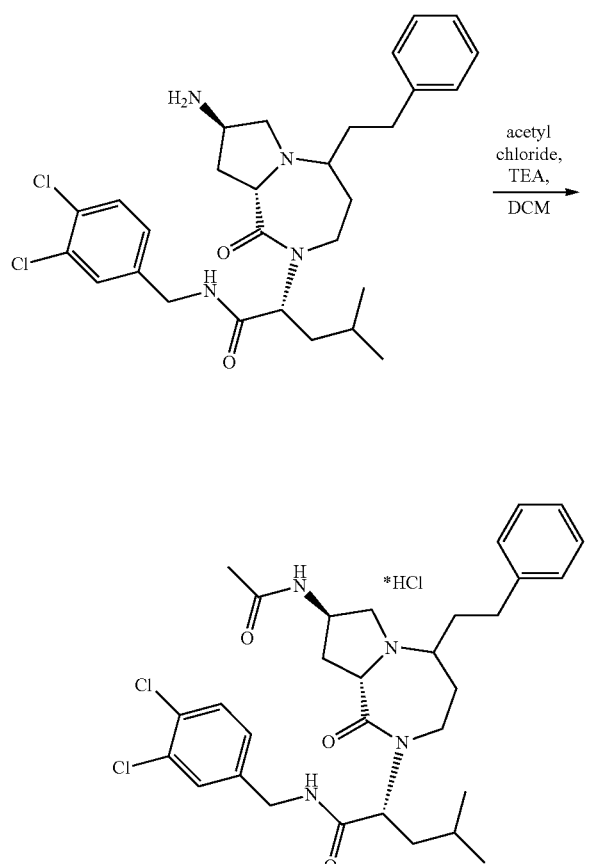

To a solution of Example 1 (20 mg, 0.037 mmol) in DCM (1 mL) was added TEA (15 μL, 0.11 mmol) followed by acetyl chloride (5 μL, 0.07 mmol). The resultant solution was stirred at ambient temperature for 1 h. The mixture was then concentrated in vacuo and the crude residue was taken up in MeOH (~1 mL) and to this was added a small scoop of $K_2CO_3$. The mixture was stirred for 15 min then diluted with DCM and filtered to remove $K_2CO_3$. The filtrate was concentrated in vacuo and the crude residue was purified directly by mass-directed preparative reverse phase HPLC (elution with 5-95% ACN/$H_2O$ containing 0.25% formic acid). The desired fractions were combined and partially concentrated in vacuo and the concentrate was treated with 3 N HCl/MeOH (~5 mL) and then partially concentrated again. The remaining solution was then treated once more with 3 N HCl/MeOH as above and partially concentrated to ensure formation of the HCl salt. The concentrated mixture was diluted with $H_2O$ and lyophilized to provide 14 mg (64%) of Example 20 as a fluffy white solid. $^1$H NMR (400 MHz, $CD_3OD$): δ 7.50-7.47 (m, 2H), 7.33-7.20 (m, 6H), 5.23 (dd, 1H), 4.34 (s superimposed on multiplet, 2H), 4.34-4.29 (m partially obscured by singlet, 1H), 4.08 (dd, 1H), 3.92 (dd, 1H), 3.70 (dd, 1H), 3.52 (app t, 1H), 3.19 (m, 1H), 2.98 (m, 1H), 2.80 (m, 1H), 2.61 (m, 1H), 2.43 (dd, 1H), 2.20 (m, 2H), 2.05-1.95 (m partially obscured by singlet, 1H), 1.96 (s, 3H), 1.80 (m, 2H), 1.66 (m, 1H), 1.49 (m, 1H), 1.33-1.29 (m, 1H), 0.98 (s, 3H), 0.92 (s, 3H) ppm; LCMS (Method A): $t_R$=1.18 min, m/z 587.5/589.5 (M+H)$^+$.

Example 21

(2R)—N-(3,4-dichlorobenzyl)-2-((8R,9aS)-8-(dimethylamino)-1-oxo-5-phenethylhexahydro-1H-pyrrolo[1,2-a][1,4]diazepin-2(3H)-yl)-4-methylpentanamide HCl

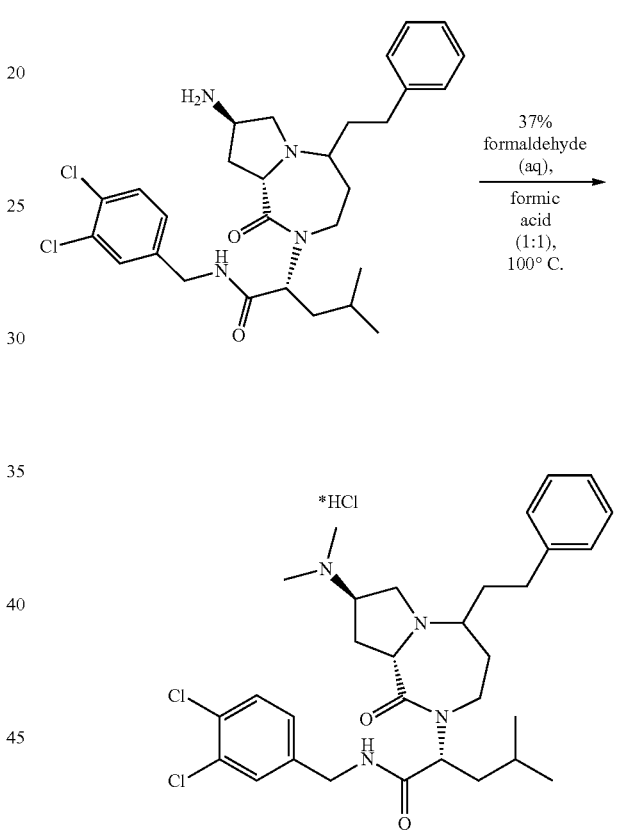

A solution of Example 1 (20 mg, 0.037 mmol) in 37% formaldehyde (aq) (1 mL) and formic acid (1 mL) was heated to 100° C. in a tightly capped reaction vial for 7 h. This was then cooled and the mixture was purified directly by mass-directed preparative reverse phase HPLC (elution with 5-95% ACN/$H_2O$ containing 0.25% formic acid). The desired fractions were combined and partially concentrated in vacuo and the concentrate was treated with 3 N HCl/MeOH (~5 mL) and then partially concentrated again. The remaining solution was then treated once more with 3 N HCl/MeOH as above and partially concentrated to ensure formation of the HCl salt. The concentrated mixture was diluted with $H_2O$ and lyophilized to provide 14 mg (67%) of Example 21. $^1$H NMR (400 MHz, $CD_3OD$): δ 7.53 (m, 1H), 7.48 (d, 1H), 7.32-7.18 (m, 6H), 5.22 (m, 1H), 5.06 (m, 1H), 4.35 (ABq superimposed on multiplet, 2H), 4.28 (m, partially obscured by AB quartet, 1H), 4.01 (m, 1H), 3.83-3.55 (m, 4H), 3.29 (m partially obscured by solvent peak, 1H), 3.00 (s, 6H), 2.76 (m, 1H), 2.57 (m, 2H), 2.36-2.21 (m, 2H), 1.98-1.80 (m, 2H), 1.72 (app t, 2H), 1.50 (m, 1H), 0.97 (d, 3H), 0.92 (d, 3H) ppm; LCMS (Method A): $t_R$=1.15 min, m/z 573.5/575.5 (M+H)$^+$.

Example 22

(2R)-2-((7R,8aS)-7-amino-1-oxo-4-phenethylhexahydropyrrolo[1,2-a]pyrazin-2(1H)-yl)-N-(3,4-dichlorobenzyl)-4-methylpentanamide.HCl Step 1: (R)—N-(3,4-dichlorobenzyl)-4-methyl-2-((2-oxo-4-phenylbutyl)amino)pentanamide (Compound 22-1)

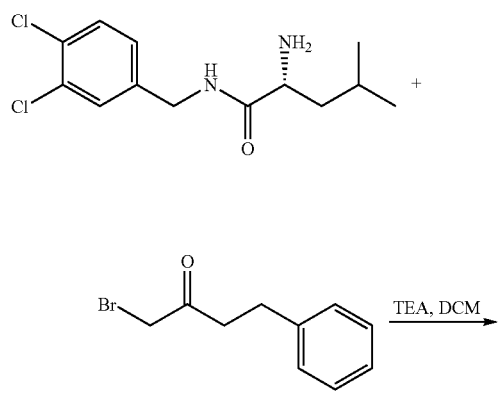

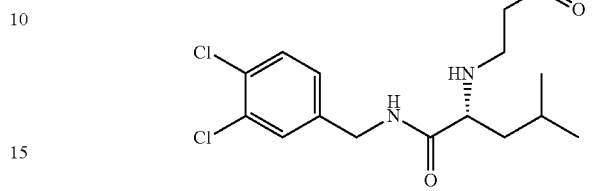

To a solution of Intermediate I.2 (67 mg, 0.23 mmol) in DCM (1 mL) was added 1-bromo-4-phenylbutan-2-one (50 mg, 0.22 mmol) followed by TEA (34 µL, 0.24 mmol). The reaction mixture was stirred at ambient temperature for 4 h. The mixture was then diluted with DCM and washed with sat. NaHCO$_3$ (aq) (2×). The organic layer was dried (MgSO$_4$), filtered and concentrated in vacuo. The crude residue was purified by FCC (SiO$_2$, elution with 0-100% EtOAc/hexanes) to provide 25 mg (26%) of Compound 22-1 as a yellow semi-solid. $^1$H NMR (400 MHz, CDCl$_3$): δ 7.55 (br t, 1H, amide N—H), 7.38 (d, 1H), 7.33 (d, 1H), 7.30-7.26 (m partially obscured by solvent peak, 2H), 7.22-7.14 (m, 3H), 7.08 (dd, 1H), 4.36 (m, 2H), 3.37 (ABq, 2H), 3.05 (dd, 1H), 2.91 (t, 2H), 2.67 (t, 2H), 1.81-1.41 (m partially obscured by H$_2$O peak, 4H), 0.95 (d, 3H), 0.92 (d, 3H) ppm; LCMS (Method A): $t_R$=1.14 min, m/z 435.4/437.4 (M+H)$^+$.

Steps 2-4: tert-butyl ((7R,8aS)-2-((R)-1-((3,4-dichlorobenzyl)amino)-4-methyl-1-oxopentan-2-yl)-1-oxo-4-phenethyloctahydropyrrolo[1,2-a]pyrazin-7-yl)carbamate (Compound 22-3)

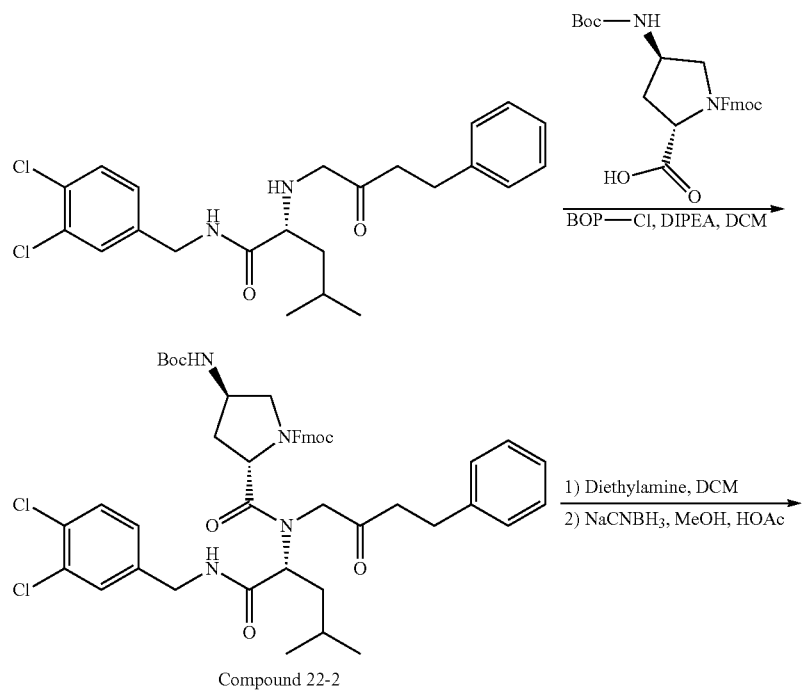

Compound 22-2

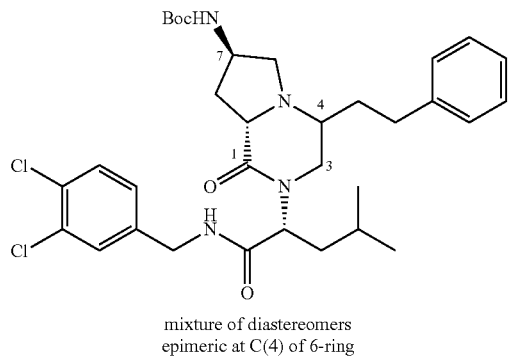

mixture of diastereomers
epimeric at C(4) of 6-ring

Compound 22-3 was prepared from Compound 22-1 (92 mg, 0.21 mmol) using the same general procedures described for the preparation of Compound 1-3 in steps 2-4 in Example 1. After work up, the crude product was purified by FCC (SiO$_2$, elution with 0-70% EtOAc/hexanes). Partial separation of the two diastereomers was achieved providing two fractions; one containing 29 mg of mainly the first eluting, major diastereomer (Compound 22-3A) and the other containing 17 mg of mainly the second eluting, minor diastereomer (Compound 22-3B). A small amount of the other diastereomer was present in each of the two fractions. The fraction containing mainly the minor diastereomer 22-3B was carried into the next step. Data for Compound 22-3A (major diastereomer): LCMS (Method C): $t_R$=0.92 min, m/z 631.4/633.3 (M+H)$^+$. Data for Compound 22-3B (minor diastereomer): LCMS (Method C): $t_R$=0.99 min, m/z 631.4/633.3 (M+H)$^+$.

Step 5: Example 22

Compound 22-3B (16 mg, 0.025 mmol) was taken up in 3N HCl in MeOH (1 mL) and the resultant solution was stirred at 50° C. in a tightly capped reaction vial for 90 min. The reaction mixture was then cooled, concentrated in vacuo and the crude residue was purified directly by preparative reverse phase MPLC (C18 column, elution with 5-95% ACN/H$_2$O). The desired fractions were combined and partially concentrated in vacuo. To this was added 3N HCl (~10 mL) and the volatiles were removed in vacuo. This treatment with 3N HCl was repeated to ensure formation of the hydrochloride salt. The mixture was then concentrated in vacuo and the residue was taken up in H$_2$O and a small amount of ACN was added to provide a clear solution which was lyophilized to provide 11 mg (79%) of Example 22 as a white solid. $^1$H NMR (400 MHz, CD$_3$OD): δ 7.47 (d, 1H), 7.43 (d, 1H), 7.32-7.27 (m, 4H), 7.23-7.20 (m, 2H), 5.17 (dd, 1H), 4.55 (m, 1H), 4.33 (ABq, 2H), 4.10-3.42 (m, 6H), 2.90-2.76 (m, 3H), 2.45 (m, 1H), 2.15 (m, 1H), 2.00 (m, 1H), 1.81 (m, 1H), 1.66 (m, 1H), 1.45 (m, 1H), 1.01 (d, 3H), 0.94 (d, 3H) ppm; LCMS (Method A): $t_R$=1.13 min, m/z 531.5/533.5 (M+H)$^+$.

Additional examples as set forth in Table 4 below were prepared in accordance with the present invention:

TABLE 4

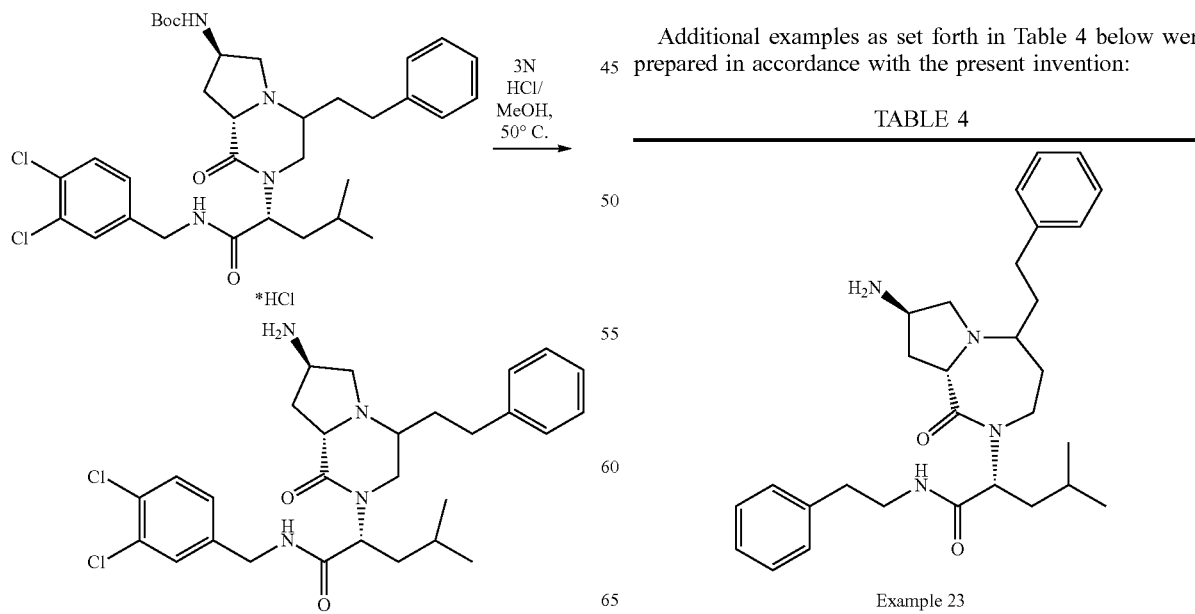

Example 23

TABLE 4-continued
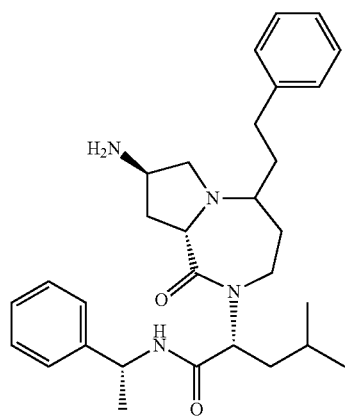
Example 24
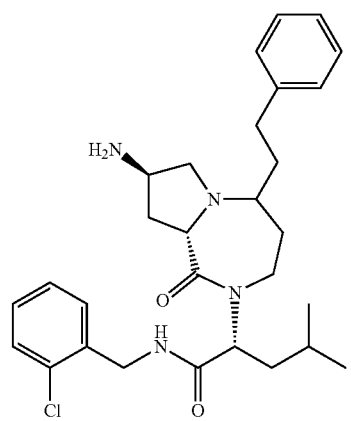
Example 27
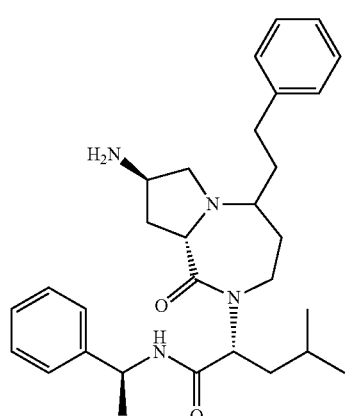
Example 25
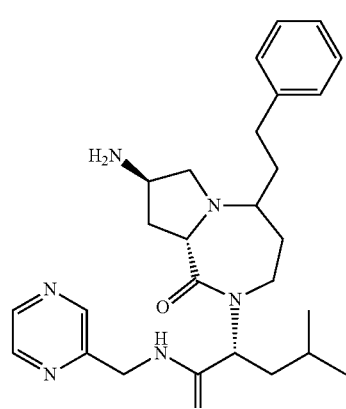
Example 28
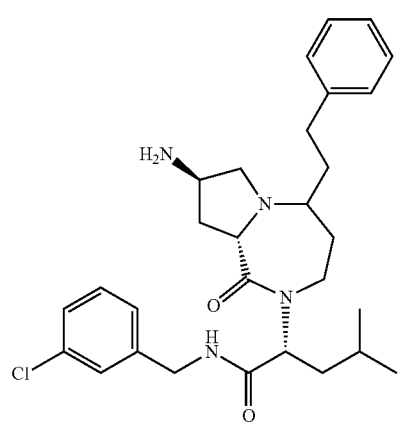
Example 26
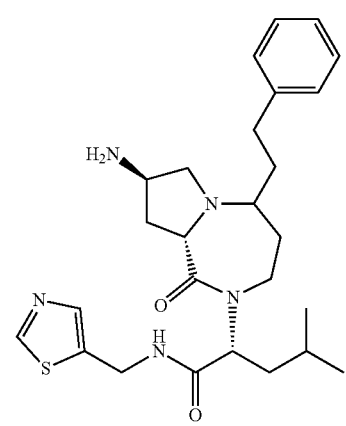
Example 29

TABLE 4-continued
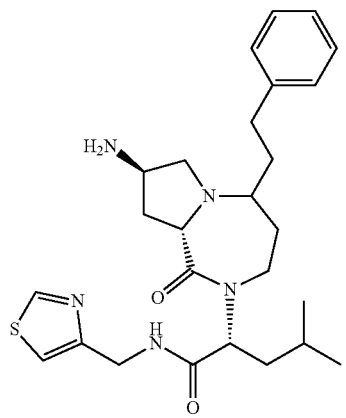
Example 30
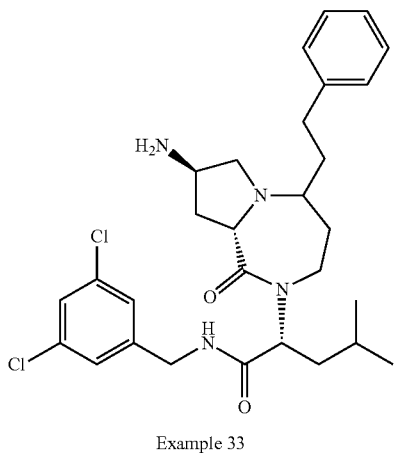
Example 33
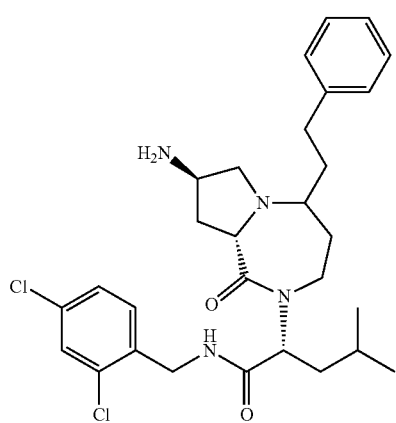
Example 31
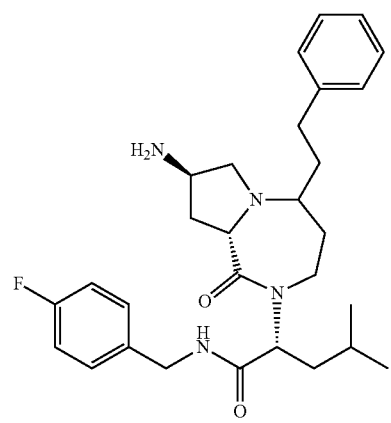
Example 34
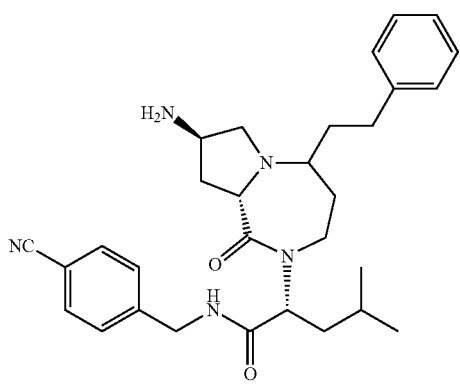
Example 32
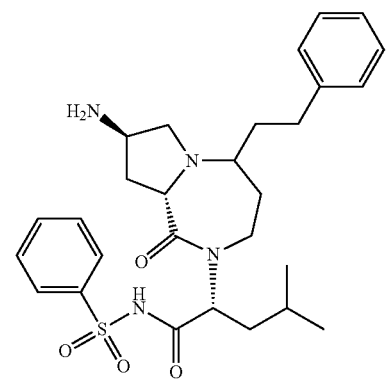
Example 35

TABLE 4-continued
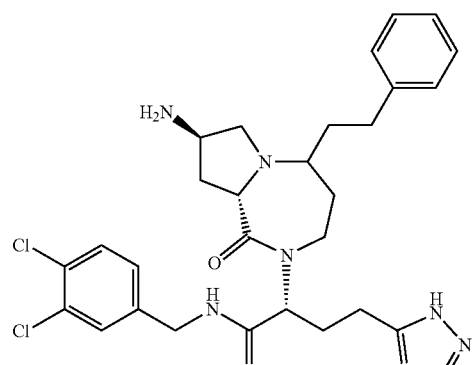
Example 36
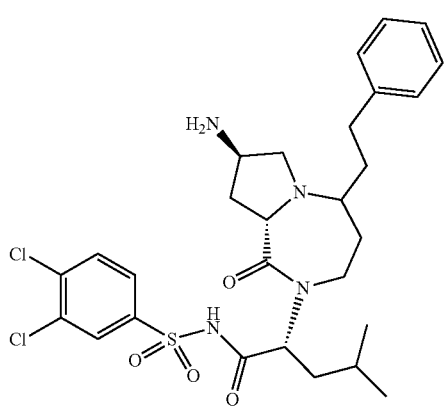
Example 39
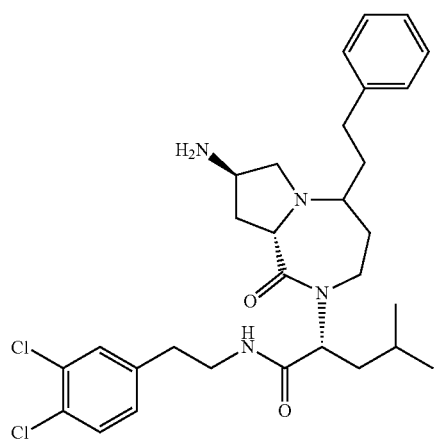
Example 37
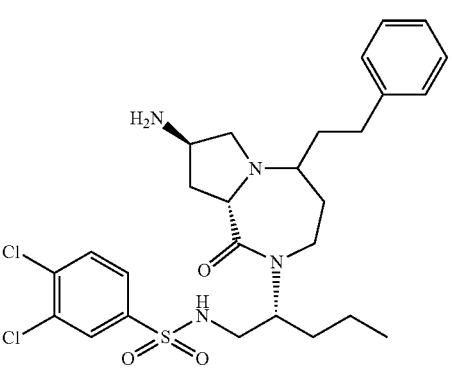
Example 40
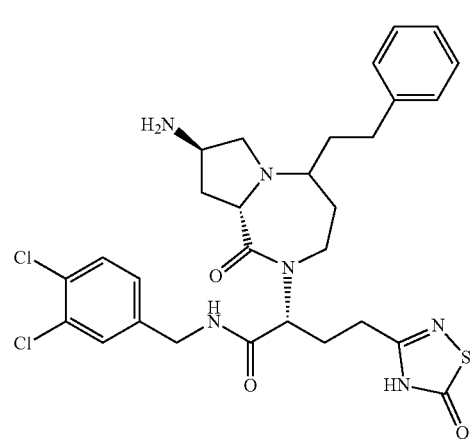
Example 38
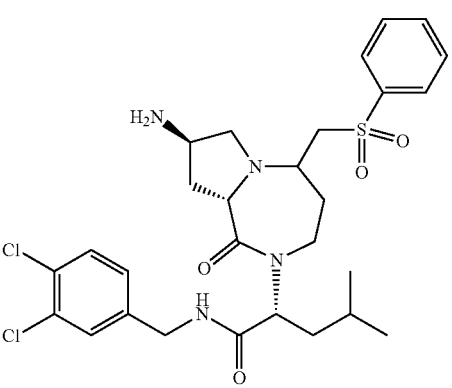
Example 41

TABLE 4-continued
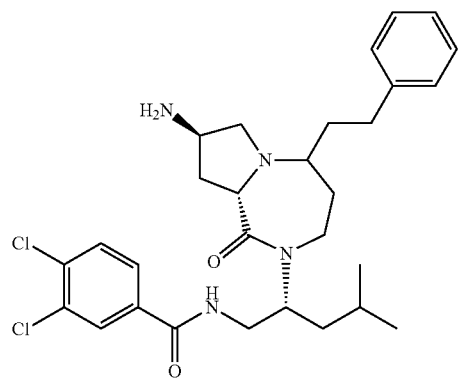
Example 42
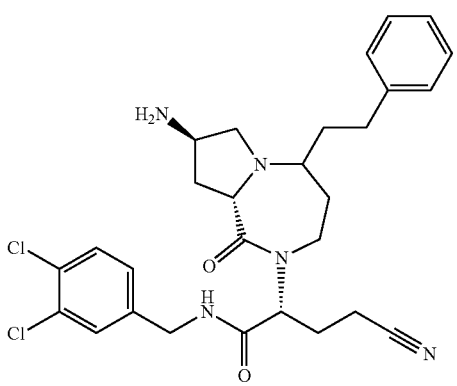
Example 45
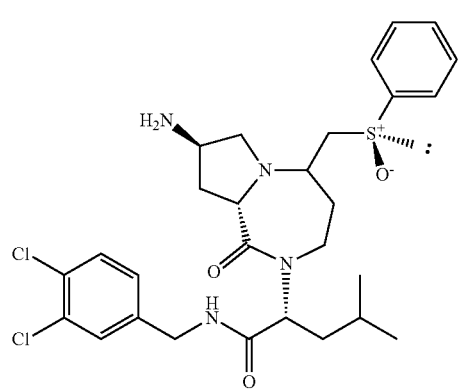
Example 43
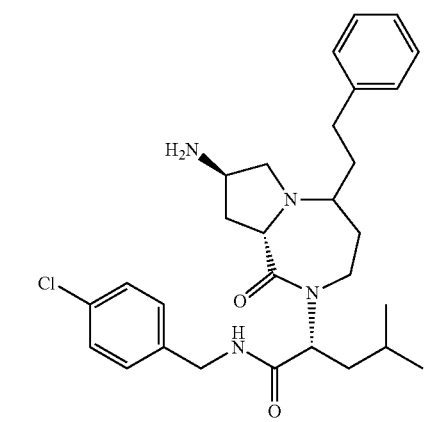
Example 46
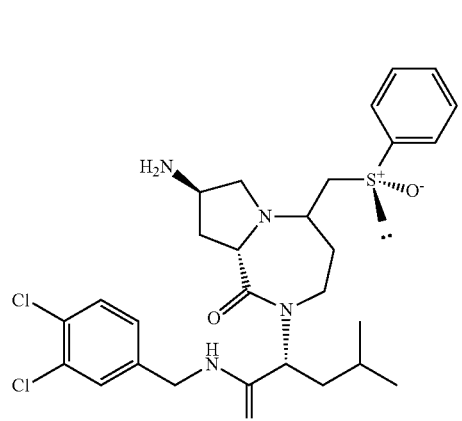
Example 44
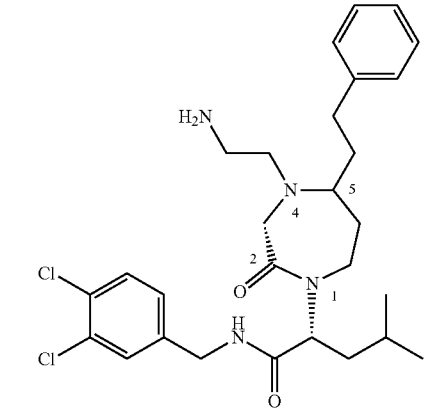
Mixture of diastereomers epimeric @ C(5)
Example 47

TABLE 4-continued

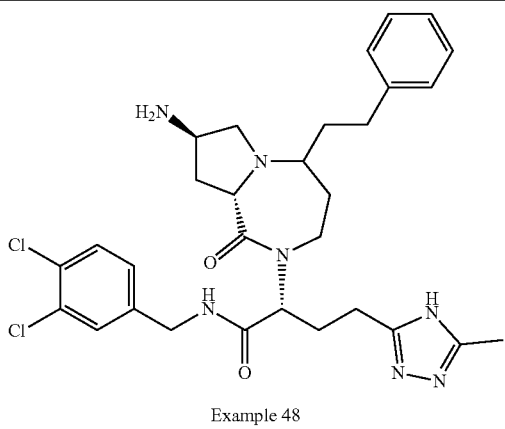

Example 48

Biology

It is desirable to find compounds with advantageous and improved characteristics compared with known TREX1 inhibitors, in one or more of the following categories that are given as examples, and are not intended to be limiting: (a) pharmacokinetic properties, including oral bioavailability, half-life, and clearance; (b) pharmaceutical properties; (c) dosage requirements; (d) factors that increase the concentration of active drug at the receptor; (e) factors that decrease the liability for clinical drug-drug interactions; (f) factors that decrease the potential for adverse side-effects, including selectivity versus other biological targets; and (g) factors that improve manufacturing costs or feasibility.

The term "compound", as used herein, means a chemical, be it naturally-occurring or artificially-derived. Compounds may include, for example, peptides, polypeptides, synthetic organic molecules, naturally occurring organic molecules, nucleic acid molecules, peptide nucleic acid molecules, and components and derivatives thereof.

As used herein, the term "patient" encompasses all mammalian species.

As used herein, the term "subject" refers to any human or nonhuman organism that could potentially benefit from treatment with a TREX1 inhibitor. Exemplary subjects include human beings of any age with risk factors for a disorder, disease, syndrome, or condition affected by the inhibition of TREX1, or patients that have already experienced one episode of a disorder, disease, syndrome, or condition affected by the inhibition of TREX1.

As used herein, "treating" or "treatment" cover the treatment of a disease-state in a mammal, particularly in a human, and include: (a) inhibiting the disease-state, i.e., arresting its development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to modulate TREX1 and/or to prevent or treat the disorders listed herein. When applied to a combination, the term refers to combined amounts of the active ingredients that result in the preventive or therapeutic effect, whether administered in combination, serially, or simultaneously.

As TREX1 inhibitors, it is believed that the compounds of Formula I, and the examples are useful in methods for treating or preventing cancer, disease, a syndrome, a condition or a disorder in a subject, including an animal, a mammal and a human in which the cancer, disease, the syndrome, the condition or the disorder is affected by the modulation, including inhibition, of the TREX1 protein. Such methods comprise, consist of and/or consist essentially of administering to a subject, including an animal, a mammal, and a human, in need of such treatment or prevention, a therapeutically effective amount of a compound, salt or solvate of Formula I.

In one embodiment, the present invention is directed to a compound of Formula I, or a stereoisomer, a tautomer, a salt, a solvate or a prodrug form thereof, for the use in the treatment of cancer, and cancer diseases and conditions, or a viral infection. Examples of cancer diseases and conditions for which compounds of Formula I, or a stereoisomer, a tautomer, a salt, a solvate or a prodrug form thereof, may have potentially beneficial antitumor effects include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary CNS lymphoma; neoplasms of the CNS; spinal axis tumors; squamous cell carcinomas; synovial sarcoma; malignant pleural mesotheliomas; brain stem glioma; pituitary adenoma; bronchial adenoma; chondromatous hanlartoma; inesothelioma; Hodgkin's Disease or a combination of one or more of the foregoing cancers. Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Duclos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal madenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, pro myelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

In another embodiment, the present invention is directed to a compound of Formula I, or a stereoisomer, a tautomer, a salt, a solvate or a prodrug form thereof, for use in the treatment of a disorder affected by the inhibition of TREX1 selected from the group consisting of melanoma, colon cancer, breast cancer, prostate cancer, lung cancer, bladder cancer, fibrosarcoma, and HIV.

In another embodiment, the present invention is directed to a compound of Formula I, or a stereoisomer, a tautomer, a salt, a solvate or a prodrug form thereof, for use in the treatment of a disorder affected by the inhibition of TREX1 wherein the disorder is bladder cancer.

The term "pharmaceutical composition," as used herein, means any composition, which contains at least one therapeutically or biologically active agent and is suitable for administration to the patient. Any of these formulations can be prepared by well-known and accepted methods of the art. See, for example, Gennaro, A. R., ed., *Remington: The Science and Practice of Pharmacy,* 20th Edition, Mack Publishing Co., Easton, Pa. (2000).

The invention includes administering to a subject a pharmaceutical composition that includes a compound that modulates TREX1 (referred to herein as a "TREX1 inhibitor" or "therapeutic compound").

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, intravesical, subcutaneous, or intramuscular form, and all using dosage forms well known to those of ordinary skill in the pharmaceutical arts. They can be administered alone, but generally will be administered with a pharmaceutical carrier selected on the basis of the chosen route of administration and standard pharmaceutical practice.

The preferred dose of the TREX1 inhibitor is a biologically active dose. A biologically active dose is a dose that will modulate the TREX1 protein and have an appropriate effect. Desirably, the dose includes a dose range from about 0.0005 mg to about 3000 mg, or any particular amount or range therein, in particular from about 0.0005 mg to about 1000 mg, or any particular amount or range therein, or, more particularly, from about 0.0005 mg to about 250 mg, or any particular amount or range therein, of active ingredient in a regimen of about 1 to about 4 times per day for an average (70 kg) human; although, it is apparent to one skilled in the art that the therapeutically effective amount for a compound of Formula I will vary as will the diseases, syndromes, conditions, and disorders being treated.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

Compounds of this invention can be administered in intravesical form via a solution that is run through a tube (instilled through a catheter) into the particular organ, for example, the bladder, to treat the cancer.

The compounds are typically administered in a mixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration will ordinarily contain the active ingredient in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods know to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of Formula I, preferably, a compound selected from one of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

The disclosed compounds of Formula I may be useful in combination with one or more additional therapeutic agents. The additional therapeutic agent may be, e.g., radiation therapy, a chemotherapeutic, a biotherapeutic agent (including but not limited to antibodies to VEGF, VEGFR, EGFR, Her2/neu, other growth factor receptors, CD20, CD40, CD-40L, CTLA-4, OX-40, 4-1BB, and ICOS), an immunogenic agent (for example, attenuated cancerous cells, tumor antigens, antigen presenting cells such as dendritic cells pulsed with tumor derived antigen or nucleic acids, immune stimulating cytokines (for example, IL-2, IFNa2, GM-CSF), and cells transfected with genes encoding immune stimulating cytokines such as but not limited to GM-CSF).

The additional therapeutic agent(s) may be administered in a single dosage form with at least one compound of the present invention, or the additional therapeutic agent(s) may be administered in separate dosage form(s) from the dosage form containing the compound of the present invention.

The compound of the present invention disclosed herein may be used in combination with one or more other therapeutic agents, including but not limited to, other anti-cancer agents that are used in the prevention, treatment, control, amelioration, or reduction of risk of a particular disease or condition. In one embodiment, a compound disclosed herein is combined with one or more other anti-cancer agents for use in the prevention, treatment, control amelioration, or reduction of risk of a particular disease or condition for which the compounds disclosed herein are useful. Such other therapeutic agents may be administered, by a route and in an amount commonly used therefor, contemporaneously or sequentially with a compound of the present disclosure.

The additional therapeutic agent(s) may be one or more agents selected from the group consisting of radiation therapy, a STING agonist, anti-viral compounds, antigens, adjuvants, anti-cancer agents, another TREX1 inhibitor, CTLA-4, LAG-3, PD-1 pathway antagonists, PD-L1 antibodies, lipids, liposomes, peptides, cytotoxic agents, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, antimetabolites, retinoids, and immunomodulatory agents including but not limited to anti-cancer vaccines. It will be understood the descriptions of the above additional therapeutic agents may be overlapping. It will also be understood that the treatment combinations are subject to optimization, and it is understood that the best combination to use of the TREX1 inhibitor, and one or more additional therapeutic agents will be determined based on the individual patient needs.

When the compound disclosed herein is used contemporaneously with one or more other therapeutic agents, the compound may be administered either simultaneously with, or before or after, one or more other therapeutic agent(s).

The weight ratio of the compound of the present invention may be varied and will depend upon the therapeutically effective dose of each agent. Generally, a therapeutically effective dose of each will be used. Combinations including at least one compound of the present invention, and other therapeutic agents will generally include a therapeutically effective dose of each active agent. In such combinations, the compound of the present invention disclosed herein and other therapeutic agents may be administered separately or in conjunction. In addition, the administration of one element may be prior to, concurrent with, or subsequent to the administration of other agent(s).

In one embodiment, this disclosure provides at least one compound of the present invention, and at least one other therapeutic agent as a combined preparation for simultaneous, separate or sequential use in therapy. In one embodiment, the therapy is the treatment of a disorder affected by the inhibition of TREX1, such as cancer.

The disclosure also provides the use of a compound of Formula I for treating a disorder affected by inhibition of TREX1, where the patient has previously (e.g., within 24 hours) been treated with another therapeutic agent.

Anti-viral compounds that may be used in combination with the compounds disclosed herein include hepatitis B virus (HBV) inhibitors, hepatitis C virus (HCV) protease inhibitors, HCV polymerase inhibitors, HCV NS4A inhibitors, HCV NSSA inhibitors, HCV NSSb inhibitors, and human immunodeficiency virus (HIV) inhibitors.

Antigens and adjuvants that may be used in combination with the compounds disclosed herein include B7 costimulatory molecule, interleukin-2, interferon-y, GM-CSF, CTLA-4 antagonists, OX-40/OX-40 ligand, CD40/CD40ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, lipopolysaccharide (LPS), monophosphoryllipid A, lipoteichoic acid, imiquimod, resiquimod, and in addition retinoic acid-inducible gene I (RIG-I) agonists such as poly I:C, used separately or in combination are also potential adjuvants.

Examples of cytotoxic agents that may be used in combination with the compounds disclosed herein include, but are not limited to, arsenic trioxide, asparaginase, and *Erwinia* L-asparaginase.

Chemotherapeutic agents that may be used in combination with the compounds disclosed herein include abiraterone acetate, altretamine, anhydrovinblastine, auristatin, bexarotene, bicalutamide, 2,3,4,5,6-pentafluoro-N-(3- fluoro-4-methoxyphenyl)benzene sulfonamide, bleomycin, N,N-dimethyl-L-valyl-L-valyl-N-methyl-L-valyl-L-prolyl-1-Lproline-t-butylamide, cachectin, cemadotin, chlorambucil, cyclophosphamide, 3',4'-didehydro-4'deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyurea and taxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onaprostone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine, and pharmaceutically acceptable salts thereof.

Examples of vascular endothelial growth factor (VEGF) receptor inhibitors include, but are not limited to, bevacizumab, Brivanib Alaninate, motesanib, pasireotide, and sorafenib.

Examples of topoisomerase II inhibitors, include but are not limited to, etoposide and teniposide.

Examples of hypomethylating agents and alkylating agents, include but are not limited to, 5-azacytidine, decitabine, temozolomide, dactinomycin, melphalan, phenylalanine mustard, altretamine, carmustine, bendamustine, busulfan, carboplatin, lomustine, cisplatin, chlorambucil, cyclophosphamide, dacarbazine, altretamine, ifosfamide, procarbazine, mechlorethamine, streptozocin, thiotepa, and pharmaceutically acceptable salts thereof.

Examples of anti-tumor antibiotics include, but are not limited to, doxorubicin, bleomycin, daunorubicin, daunorubicin liposomal, mitoxantrone, epirubicin, idarubicin, and mitomycin C.

Examples of anti-metabolites include, but are not limited to, claribine, 5-fluorouracil, 6-thioguanine, pemetrexed, cytarabine, cytarabine liposomal, decitabine, hydroxyurea fludarabine, floxuridine, cladribine, methotrexate, and pentostatin.

Examples of retinoids include, but are not limited to, alitretinoin, tretinoin, isotretinoin and bexarotene.

Examples of PD-1 antagonists include, but are not limited to, nivolumab, pembrolizumab, pidilizumab, and AMP-224.

Examples of PD-L1 antibodies include, but are not limited to, Atezolizumab, Avelumab, and Durvalumab.

An example of a CLT-4 antagonist is ipilimumab.

Examples of STING agonists include, but are not limited to, those disclosed in International Published Patent Application Nos. WO 2017/027645 A1, WO 2017/027646 A1 and WO 2018/118664 A1.

The activity of the TREX1 inhibitors of the present invention can be measured in a variety of in vitro assays. Exemplary assays are shown in the Examples below.

The TREX1 Exonuclease assay is an exemplary in vitro assay for measuring the activity of the TREX1 inhibitors of the present invention. In this assay, TREX1 exonuclease activity was evaluated by measuring the increase in fluorescence resulting from TREX1-catalyzed removal of a quencher from the 3' end of a FAM-labeled DNA oligonucleotide (5'FAM-CCA CGA GAG CGT-BHQ1-3'). The assay was conducted using Wild Type (WT) human or murine TREX1 enzyme constructs corresponding to amino acids 55-297 of UniProt ID Q9NSU2-1 (SEQ ID NO: 1), or amino acids 1-242 of UniProt ID Q91XB0-1 (SEQ ID NO: 2), respectively. See, e.g., Example A.

Example B is a protein thermal shift assay used to assess the binding of TREX1 inhibitors to TREX1 protein. In this assay, TREX1 protein unfolding with increasing temperature was measured in the presence and absence of TREX1 inhibitors by following the increase in fluorescence of a thiol-reactive dye (e.g BODIPY FL-cystine) as it reacts with exposed TREX1 cysteine residues. The assay was conducted using human (SEQ ID NO: 1), or murine (SEQ ID NO: 2) TREX1 protein constructs.

Example C is a cell-based assay for TREX1 inhibitors using THP1 Dual™ cells (Invivogen), a human monocyte cell line that has stable integration of an Interferon Stimulated Response Element (ISRE) Lucia reporter gene. The Lucia gene encodes a secreted luciferase reporter protein, under the control of an ISG54 minimal promoter in conjunction with five IFN-stimulated response elements. Activation of the cGAS-STING pathway in THP1 Dual™ cells leads to enhanced luciferase secretion and increased luminescence.

Example D is a cell based assay that measures the increase in the expression of interferon stimulated genes (ISG) by RT-qPCR that are induced by TREX1 inhibitors when THP1 Dual™ cells are transfected with double-stranded DNA. The double stranded DNA used to transfect cells was VACV-70 (Invivogen), a 70 base pair oligonucleotide containing viral DNA motifs (Unterholzner L. et al., 2010. IFI16 is an innate immune sensor for intracellular DNA. Nat Immunol. 11(11): 997-1004). Activation of cGAS-STING pathway in THP1 Dual™ cells increases the expression of ISGs.

Assays

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

Example A

TREX1 Exonuclease Assay

For human TREX1, the nucleotide sequence of the gene construct was codon optimized for expression in the bacterial host. The sequence was incorporated into the pMAL-c5e vector (NEB) downstream of a solubility-promoting MBP (maltose binding protein) fusion partner. The fusion protein product was expressed in *E. coli* strain BL21 (DE3) (Millipore) and purified in a series of chromatographic steps. Initial steps were conducted using a dextrin sepharose affinity column followed by a Q-sepharose ion exchange column (both GE Healthcare). After the second column the MBP partner was removed by incubation with enterokinase (NEB). Further purification was carried out with the second application of a Q-sepharose column followed by a Superdex 75 (GE Healthcare) size exclusion column. Finally, a heparin sepharose column (GE Healthcare) was applied to remove contaminating nucleotides. Similar methods were used in the preparation of the murine TREX1 enzyme and are described in Example B set forth below.

To evaluate the effect of compounds on TREX1 activity, test compounds were serially diluted (11-point, 3-fold) from 10 mM stock solutions and delivered to 384-well low-volume assay plates in 80 nL DMSO using an acoustic dispenser. Next, 4 µL of human TREX1 (0.5 nM), or murine TREX1 (1 nM), diluted in assay buffer (20 mM Tris pH 7.5, 5 mM $MgCl_2$, 100 µg/mL BSA, 0.002% Triton X-100, 2 mM DTT), was added to the assay plate. After incubating for 30 minutes, 4 µL of labeled DNA oligonucleotide (500 nM) in assay buffer was added to initiate TREX1 exonuclease activity. The reaction was allowed to proceed for 45 minutes at room temperature prior to the addition of 4 µL of 150 mM EDTA to halt TREX1 activity. Assay plates were equilibrated for an additional 30 minutes and read on an EnVision Plate Reader (Perkin Elmer) to measure fluorescence emission at 535 nm following excitation at 485 nm. Fluorescence was plotted as a function of log molar compound concentration and fit to four-parameter dose-response equation to determine compound $IC_{50}$.

Compounds of the present invention were tested in the TREX1 Exonuclease assay described immediately above and the results shown in Table 5 below were obtained.

TABLE 5

A: $IC_{50}$ < 1.00 µM; B: $IC_{50}$ = 1.00 µM-9.99 µM; C: $IC_{50}$ = 10.0 µM-100 µM; D: $IC_{50}$ > 100 µM

| Example | Human TREX1 $IC_{50}$ (µM) | Murine TREX1 $IC_{50}$ (µM) |
|---|---|---|
| 1 | A | A |
| 2A | C | C |
| 2B | A | A |
| 3 | A | A |
| 4 | A | A |
| 5 | A | A |
| 6 | A | A |
| 7 | B | B |
| 8 | B | C |
| 9 | B | B |
| 10 | B | B |
| 11 | A | B |
| 12 | C | C |
| 13 | C | C |
| 14A | C | C |
| 14B | A | A |
| 15 | A | A |
| 16 | A | A |
| 17 | A | A |
| 18 | A | A |
| 19 | A | B |
| 20 | B | C |
| 21 | C | D |

TABLE 5-continued

A: $IC_{50}$ < 1.00 µM; B: $IC_{50}$ = 1.00 µM-9.99 µM; C: $IC_{50}$ = 10.0 µM-100 µM; D: $IC_{50}$ > 100 µM

| Example | Human TREX1 $IC_{50}$ (µM) | Murine TREX1 $IC_{50}$ (µM) |
|---|---|---|
| 22 | C | C |
| 23 | B | C |
| 24 | C | C |
| 25 | C | C |
| 26 | A | B |
| 27 | B | C |
| 28 | B | C |
| 29 | B | C |
| 30 | B | C |
| 31 | A | B |
| 32 | B | C |
| 33 | A | B |
| 34 | A | B |
| 35 | B | B |
| 36 | A | A |
| 37 | A | B |
| 38 | A | A |
| 39 | A | A |
| 40 | A | B |
| 41 | B | C |
| 42 | B | B |
| 43 | A | B |
| 44 | A | B |
| 45 | A | A |
| 46 | A | B |
| 47 | B | C |
| 48 | A | A |

Example B

TREX1 Thermal Shift Binding Assay

The thermal shift assays used recombinant protein corresponding to human (SEQ ID NO: 1) and murine (SEQ ID NO: 2) TREX1. The protein encoding plasmid contained a N-terminal MBP (maltose binding protein) tag followed by the TREX1 coding sequence within the pMAL-c5E vector. The plasmid was transfected into a BL21 (DE3) *E. coli* expression strain. Protein was purified from the bacterial lysate using an Amylose resin column. The MBP tag was cleaved from the purified protein using recombinant enterokinase (EMD Millipore #69066-3). The cleaved TREX1 protein was further purified on a Q-Sepharose column followed by a heparin column.

Binding of compounds to both human and murine TREX1 were measured by protein thermal shift assays. (Huynh K, Partch C L. Current Protocols in Protein Science: Analysis of protein stability and ligand interactions by thermal shift assay. *Current protocols in protein science/editorial board*, John E Coligan. [et al]. 2015; 79:28.9.1-28.9.14. doi: 10.1002/0471140864.ps2809s79.). Thermal shift assays were conducted in sealed 96-well PCR plates containing 5 µM TREX1 protein, 100 µM compound, and 2 µM BODIPY FL-cystine (Sigma) in either 20 µL assay buffer (20 mM Tris, 7.5, 5 mM $MgCl_2$, 0.002% Triton X-100) or 20 µL phosphate buffered saline (PBS). Using a RT-qPCR machine (Mx3005P, Stratagene) changes in fluorescence (excitation at 492 nm and emission at 516 nm) were monitored as temperature was increased from 25° C. to 96° C. at a rate of 1° C. every 2 minutes. $T_m$ values were calculated from the first derivative plot of fluorescence intensity versus temperature. The results shown in Table 6 indicate the examples bind to human TREX1 and murine TREX1. ND indicates assay was not done.

TABLE 6

A: $\Delta T_m > 8°$ C.; B: $8°$ C. $\geq \Delta T_m \geq 4°$ C.

| VB number | Example number | Thermal shift cleaved human TREX1, ($\Delta Tm °$ C.) | | Thermal shift cleaved mouse TREX1, ($\Delta Tm °$ C.) | |
|---|---|---|---|---|---|
| | | PBS | Assay buffer | PBS | Assay buffer |
| | Example 1 | A | A | B | B |
| | Example 2B | A | A | B | B |
| | Example 3 | A | A | B | B |
| | Example 4 | A | A | B | B |
| | Example 14B | ND | A | A | ND |

Example C

HP1 Monocyte Assay

A cell-based assay was established using THP1 Dual™ cells (Invivogen), a human monocyte cell line that has stable integration of an Interferon Stimulated Response Element (ISRE) Lucia reporter gene. The Lucia gene encodes a secreted luciferase reporter protein, under the control of an ISG54 minimal promoter in conjunction with five IFN-stimulated response elements. Activation of the cGAS-STING pathway in these cells leads to enhanced luciferase secretion. The assay was conducted in standard 384-well white tissue culture plates. Cells (25,000 in 25 μL RPMI 1640 containing 10% Heat-Inactivated FBS, 1× Glutagro, 10 mM HEPES, 1 mM sodium pyruvate, 1× Pen/Strep, 100 μg/mL Normocin, 100 μg/mL Zeocin, 10 μg/mL Blasticidin) were added to the plate followed by 25 μL of compound in the same media+0.2% DMSO. The assay was incubated for 48 hours at 37° C. in 5% $CO_2$. An aliquot of 5 μl was removed to combine with 12.5 μL of the luciferase detection reagent, QUANTI-Luc™ Gold (Invivogen) in a white 384-well plate. The luminescent signal was then read using an EnVision plate reader (Perkin Elmer). The fold activation was calculated by dividing the signal in wells containing test compound by the signal in the control wells without compound (see Table 7).

TABLE 7

| Example compound | Fold activation @ 10 μM |
|---|---|
| Example 14B | 12 |
| Example 15 | 2 |
| Example 16 | 4 |
| Example 36 | 7 |

Example D

RT-qPCR Assay

The RT-qPCR assay was used to assess the ability of TREX1 inhibitors to enhance the expression of interferon stimulated genes (ISGs) in cells transfected with double-stranded DNA. The double stranded DNA used to transfect cells was VACV-70 (Invivogen), a 70 base pair oligonucleotide containing viral DNA motifs (Unterholzner L. et al., 2010. IFI16 is an innate immune sensor for intracellular DNA. Nat Immunol. 11(11):997-1004). Human THP1 Dual™ cells (Invivogen), were treated with test compound in the presence or absence of 1,200 ng/mL VACV-70, or with VACV-70 alone, for 24 hours. Cells were harvested by centrifugation and washed with phosphate buffer saline. Total RNA was isolated using Qiagen RNeasy mini kit. Genomic DNA was degraded using Thermo Scientific DNase 1 kit. Total RNA was quantified using a Nanodrop spectrophotometer. Using equal amounts of RNA, cDNA was synthesized using Invitrogen Superstrand III First Strand synthesis kit. Target and reference gene expression levels were determined by RT-qPCR using TaqMan gene expression assays and a Stratagene Mx3005P QPCR system (all reagents were from TaqMan, Applied Biosystems). Data were analyzed by the Comparative $C_T$ method. GAPDH was used for normalization. Target genes that were analyzed included interferon stimulated genes (INF-β, CXCL10, IFIT1, IFIT2, IFIT3, IFI44, and IFI44L). The data are shown in Table 8.

TABLE 8

| | IFN-β | CXCL10 | IFIT1 | IFIT2 | IFIT3 | IFI44 | IFI44L |
|---|---|---|---|---|---|---|---|
| Unstimulated control | 1 | 1 | 1 | 1 | 1 | 1 | 1 |
| VACV70 alone | 732 | 185 | 813 | 518 | 355 | 827 | 2076 |
| (Example 14B) alone | 7 | 2 | 19 | 44 | 25 | 54 | 65 |
| (Example 14B) + VACV70 | 2725 | 729 | 3580 | 7928 | 2297 | 2929 | 5263 |
| (Example 15) alone | 5 | 1 | 10 | 32 | 20 | 20 | 20 |
| (Example 15) + VACV70 | 3449 | 712 | 4373 | 9581 | 3348 | 3969 | 3348 |
| (Example 16) alone | 6 | 2 | 11 | 41 | 25 | 14 | 15 |
| (Example 16) + VACV70 | 3692 | 1941 | 3676 | 8218 | 2729 | 3618 | 2729 |
| (Example 36) alone | 3 | 2 | 8 | 26 | 16 | 20 | 16 |
| (Example 36) + VACV70 | 3856 | 1827 | 4391 | 11285 | 3768 | 4344 | 3768 |

While it is apparent that the embodiments of the application herein disclosed are well suited to fulfill the objectives stated above, it will be appreciated that numerous modifications and other embodiments may be implemented by those skilled in the art, and it is intended that the appended claims cover all such modifications and embodiments that fall within the true spirit and scope of the present application.

What is claimed is:

1. A compound of Formula I:

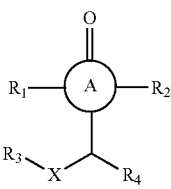

or a pharmaceutically acceptable salt, solvate, stereoisomer, or tautomer thereof, wherein:

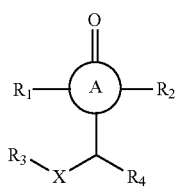 is 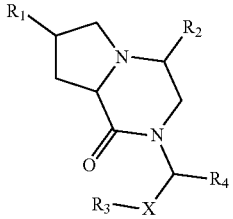 or 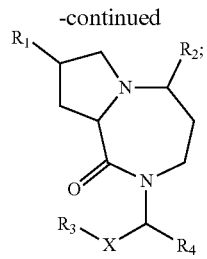

X is —$C_1$-$C_6$ alkylene-$NR_5C(O)$—, —$C_1$-$C_6$ alkylene-$NR_5S(O)_2$—, —$C(O)NR_5$—, —$C(O)NR_5S(O)_2$—, or a 5-membered heteroarylene, wherein the 5-membered heteroarylene contains at least 1 nitrogen heteroatom;

$R_1$ is $C_1$-$C_6$ alkylene-$NR_5R_6$ or $NR_5R_6$;

$R_2$ is $C_1$-$C_6$ alkyl, $C_1$-$C_6$ alkylene-O—$C_6$-$C_{10}$ aryl, $C_1$-$C_6$ alkylene-O-5- to 10-membered heteroaryl, $C_1$-$C_6$ alkylene-S—$C_6$-$C_{10}$ aryl, $C_1$-$C_6$ alkylene-S—5- to 10-membered heteroaryl, $C_1$-$C_6$ alkylene-S(O)—$C_6$-$C_{10}$ aryl, $C_1$-$C_6$ alkylene-S(O)-5- to 10-membered heteroaryl, $C_1$-$C_6$ alkylene-S(O)$_2$—$C_6$-$C_{10}$ aryl, $C_1$-$C_6$ alkylene-S(O)$_2$-5 to 10-membered heteroaryl, $C_1$-$C_6$ alkylene-$C_6$-$C_{10}$ aryl, or $C_1$-$C_6$ alkylene-5- to 10-membered heteroaryl, wherein any $C_6$-$C_{10}$ aryl or 5- to 10-membered heteroaryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_4$ haloalkyl;

$R_3$ is $C_1$-$C_6$ alkyl, $C_1$-$C_6$ alkylene-$C_3$-$C_6$ cycloalkyl, $C_1$-$C_6$ alkylene-$C_6$-$C_{10}$ aryl, $C_1$-$C_6$ alkylene-5- to 10-membered heteroaryl, or $C_6$-$C_{10}$ aryl, wherein any $C_3$-$C_6$ cycloalkyl, $C_6$-$C_{10}$ aryl, or 5- to 10-membered heteroaryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_6$ haloalkyl;

$R_4$ is $C_1$-$C_6$ alkyl, wherein the $C_1$-$C_6$ alkyl is optionally substituted with 1 or more substituents independently selected from the group consisting of CN, $C(O)NR_8R_9$, $C(O)NR_8S(O)_2R_9$, $C(O)NR_8S(O)_2NR_{28}R_{29}$, $C(O)OH$, $NR_8R_9$, $NR_{28}C(O)NR_8R_9$, $NR_{28}C(O)NR_8S(O)_2R_9$, $NR_8S(O)_2R_9$, OH, $ONR_8R_9$, $SR_9$, $S(O)R_9$, $S(O)_2R_9$, $S(O)_2NR_8R_9$, $S(O)_2OH$, $C_6$-$C_{10}$ aryl, and a 5- to 10-membered heteroaryl, wherein the 5- to 10-membered heteroaryl contains at least 1 nitrogen heteroatom, and further wherein any $C_6$-$C_{10}$ aryl or 5- to 10-membered heteroaryl is optionally and independently substituted with 1 or more substituents independently selected from the group consisting of halo, CN, $C_1$-$C_4$ alkyl, $C_1$-$C_4$ haloalkyl, OH, =O, $OC_1$-$C_4$ alkyl, and $OC_1$-$C_4$ haloalkyl;

each $R_5$ is independently H, $C_1$-$C_6$ alkyl, or $C_1$-$C_6$ haloalkyl;

each $R_6$ is independently H, $C_1$-$C_6$ alkyl, $C_1$-$C_6$ haloalkyl, or $C(O)R_7$;

each $R_7$ is independently $C_1$-$C_6$ alkyl or $OC_1$-$C_6$ alkyl;

each $R_8$ is independently H, $C_1$-$C_4$ alkyl, $C_1$-$C_4$ haloalkyl, $C(O)C_1$-$C_4$ alkyl, $OC_1$-$C_4$ alkyl, or $OC_1$-$C_4$ haloalkyl;

each $R_9$ is independently H, $C_1$-$C_4$ alkyl, OH, $OC_1$-$C_4$ alkyl, $C_3$-$C_6$ cycloalkyl, or $C_6$-$C_{10}$ aryl, wherein each $C_1$-$C_4$ alkyl, $OC_1$-$C_4$ alkyl, $C_3$-$C_6$ cycloalkyl, and $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, =O, $OC_1$-$C_4$ alkyl, and $OC_1$-$C_4$ haloalkyl;

each $R_{28}$ is independently H, $C_1$-$C_4$ alkyl, $C_1$-$C_4$ haloalkyl, $OC_1$-$C_4$ alkyl, or $OC_1$-$C_4$ haloalkyl; and each $R_{29}$ is independently H, $C_1$-$C_4$ alkyl, $C_1$-$C_4$ haloalkyl, $OC_1$-$C_4$ alkyl, or $OC_1$-$C_4$ haloalkyl.

2. The compound of claim 1, or a pharmaceutically acceptable salt, solvate, stereoisomer, or tautomer thereof, wherein:

X is —$C_1$-$C_6$ alkylene-$NR_5C(O)$—, —$C(O)NR_5$—, —$C(O)NR_5S(O)_2$—, or a 5-membered heteroarylene, wherein the 5-membered heteroarylene contains at least 1 nitrogen heteroatom;

$R_2$ is $C_1$-$C_6$ alkyl, $C_1$-$C_6$ alkylene-O—$C_6$-$C_{10}$ aryl, $C_1$-$C_6$ alkylene-S—$C_6$-$C_{10}$ aryl, $C_1$-$C_6$ alkylene-S(O)—$C_6$-$C_{10}$ aryl, $C_1$-$C_6$ alkylene-$S(O)_2$-$C_6$-$C_{10}$ aryl, or $C_1$-$C_6$ alkylene-$C_6$-$C_{10}$ aryl, wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_4$ haloalkyl;

$R_3$ is $C_1$-$C_6$ alkyl, $C_1$-$C_6$ alkylene-$C_6$-$C_{10}$ aryl, $C_1$-$C_6$ alkylene-5- to 10-membered heteroaryl, or $C_6$-$C_{10}$ aryl, wherein any $C_6$-$C_{10}$ aryl or the 5- to 10-membered heteroaryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_6$ haloalkyl;

$R_4$ is $C_1$-$C_6$ alkyl, wherein the $C_1$-$C_6$ alkyl is optionally substituted with 1 or more substituents independently selected from the group consisting of CN, $C(O)NR_8R_9$, $C(O)OH$, OH, $C_6$-$C_{10}$ aryl, and 5-membered heteroaryl, wherein the 5-membered heteroaryl contains at least 1 nitrogen heteroatom, and further wherein any $C_6$-$C_{10}$ aryl or 5-membered heteroaryl is optionally and independently substituted with 1 or more substituents independently selected from the group consisting of halo, CN, $C_1$-$C_4$ alkyl, $C_1$-$C_4$ haloalkyl, OH, =O, $OC_1$-$C_4$ alkyl, and $OC_1$-$C_4$ haloalkyl;

each $R_8$ is independently H, $C_1$-$C_4$ alkyl, $C_1$-$C_4$ haloalkyl, or $OC_1$-$C_4$ alkyl; and each $R_9$ is independently H, $C_1$-$C_4$ alkyl, $C_1$-$C_4$ haloalkyl, or $OC_1$-$C_4$ alkyl.

3. The compound of claim 1, or a pharmaceutically acceptable salt, solvate, stereoisomer, or tautomer thereof, wherein:

X is —$C_1$-$C_6$ alkylene-$NR_5C(O)$—, —$C(O)NR_5$—, or a 5-membered heteroarylene, wherein the 5-membered heteroarylene contains at least 1 nitrogen heteroatom;

$R_2$ is $C_1$-$C_6$ alkyl, $C_1$-$C_6$ alkylene-O—$C_6$-$C_{10}$ aryl, $C_1$-$C_6$ alkylene-S—$C_6$-$C_{10}$ aryl, or $C_1$-$C_6$ alkylene-$C_6$-$C_{10}$ aryl, wherein any $C_6$-$C_{10}$ aryl is optionally and independently substituted with 1 or more substituents independently selected from the group consisting of halo, CN, $C_1$-C alkyl, $C_1$-$C_4$haloalkyl, OH, $OC_1$-$C_4$ alkyl, and $OC_1$-$C_4$ haloalkyl;

$R_3$ is $C_1$-$C_6$ alkyl, $C_1$-$C_6$ alkylene-$C_6$-$C_{10}$ aryl, $C_1$-$C_6$ alkylene-5-membered heteroaryl, or $C_6$-$C_{10}$ aryl, wherein any $C_6$-$C_{10}$ aryl or 5-membered heteroaryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_6$ haloalkyl;

$R_4$ is $C_1$-$C_6$ alkyl, wherein the $C_1$-$C_6$ alkyl is optionally substituted with 1 or more substituents independently selected from the group consisting of CN, $C(O)NR_8R_9$, $C(O)OH$, OH, $C_6$-$C_{10}$ aryl, and 5-membered heteroaryl, wherein the 5-membered heteroaryl contains at least 1 nitrogen heteroatom, and further wherein any $C_6$-$C_{10}$ aryl or 5-membered heteroaryl is optionally and independently substituted with 1 or more substituents independently selected from the group consisting of halo, CN, $C_1$-$C_4$ alkyl, $C_1$-$C_4$ haloalkyl, OH, =O, $OC_1$-$C_4$ alkyl, and $OC_1$-$C_4$ haloalkyl;

each $R_8$ is independently H, $C_1$-$C_4$ alkyl, $C_1$-$C_4$ haloalkyl, or $OC_1$-$C_4$ alkyl; and each $R_9$ is independently H, $C_1$-$C_4$ alkyl, $C_1$-$C_4$ haloalkyl, or $OC_1$-$C_4$ alkyl.

4. The compound of claim 3, or a pharmaceutically acceptable salt, solvate, stereoisomer, or tautomer thereof, wherein:

X is —$C(O)NR_5$—;

$R_1$ is $NR_5R_6$;

$R_2$ is $C_1$-$C_6$ alkylene-$C_6$-$C_{10}$ aryl, wherein the $C_6$-$C_{10}$ aryl is optionally substituted with 1 or more substituents independently selected from the group consisting of halo, CN, $C_1$-$C_4$ alkyl, OH, and $OC_1$-$C_4$ haloalkyl;

$R_3$ is $C_1$-$C_6$ alkylene-$C_6$-$C_{10}$ aryl, wherein the $C_6$-$C_{10}$ aryl is optionally substituted with 1 or more substituents independently selected from the group consisting of halo, CN, $C_1$-$C_4$ alkyl, $C_1$-$C_4$ haloalkyl, and OH;

$R_4$ is $C_1$-$C_6$ alkyl, wherein the $C_1$-$C_6$ alkyl is optionally substituted with 1 or more substituents independently selected from the group consisting of $C(O)OH$, OH, $C_6$-$C_{10}$ aryl, and 5-membered heteroaryl, wherein the 5-membered heteroaryl contains at least 1 nitrogen heteroatom, and further wherein any $C_6$-$C_{10}$ aryl or 5-membered heteroaryl is optionally and independently substituted with 1 or more substituents independently selected from the group consisting of halo, CN, $C_1$-$C_4$ alkyl, $C_1$-$C_4$ haloalkyl, OH, =O, $OC_1$-$C_4$ alkyl, and $OC_1$-$C_4$ haloalkyl;

each $R_5$ is independently H or $CH_3$; and $R_6$ is H or $C_1$-$C_6$ alkyl.

5. The compound of claim 4, or a pharmaceutically acceptable salt, solvate, stereoisomer, or tautomer thereof, wherein:

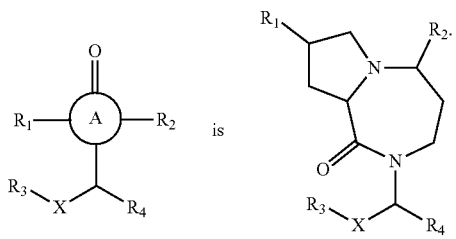

6. The compound of claim 5, or a pharmaceutically acceptable salt, solvate, stereoisomer, or tautomer thereof, wherein $R_4$ is $C_1$-$C_6$ alkyl, wherein the $C_1$-$C_6$ alkyl is substituted with 1 substituent selected from the group consisting of C(O)OH and 5-membered heteroaryl, wherein the 5-membered heteroaryl contains at least 1 nitrogen heteroatom, and further wherein the 5-membered heteroaryl is optionally substituted with 1 or more substituents independently selected from the group consisting of halo, CN, $C_1$-$C_4$ alkyl, $C_1$-$C_4$ haloalkyl, OH, =O, $OC_1$-$C_4$ alkyl, and $OC_1$-$C_4$ haloalkyl.

7. The compound of claim 1, or a pharmaceutically acceptable salt, solvate, stereoisomer, or tautomer thereof, wherein:

X is —$C_1$-$C_6$ alkylene-$NR_5C(O)$— or —$C(O)NR_5$—;

$R_2$ is $C_1$-$C_6$ alkyl, $C_1$-$C_6$ alkylene-O—$C_6$-$C_{10}$ aryl, or $C_1$-$C_6$ alkylene-$C_6$-$C_{10}$ aryl, wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_4$ haloalkyl;

$R_3$ is $C_1$-$C_6$ alkyl, $C_1$-$C_6$ alkylene-$C_6$-$C_{10}$ aryl, or $C_6$-$C_{10}$ aryl, wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_6$ haloalkyl;

$R_4$ is $C_1$-$C_6$ alkyl, wherein the $C_1$-$C_6$ alkyl is optionally substituted with 1 or more substituents independently selected from the group consisting of CN, $C(O)NR_8R_9$, C(O)OH, OH, and $C_6$-$C_{10}$ aryl, wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_4$ haloalkyl;

each $R_8$ is independently H, $C_1$-$C_4$ alkyl, $C_1$-$C_4$ haloalkyl, or $OC_1$-$C_4$ alkyl; and each $R_9$ is independently H, $C_1$-$C_4$ alkyl, $C_1$-$C_4$ haloalkyl, or $OC_1$-$C_4$ alkyl.

8. The compound of claim 1, or a pharmaceutically acceptable salt, solvate, stereoisomer, or tautomer thereof, wherein:

X is —$C_1$-$C_6$ alkylene-$NR_5C(O)$— or —$C(O)NR_5$—;

$R_2$ is $C_1$-$C_6$ alkyl or $C_1$-$C_6$ alkylene-$C_6$-$C_{10}$ aryl, wherein the $C_6$-$C_{10}$ aryl is optionally substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_4$ haloalkyl;

$R_3$ is $C_1$-$C_6$ alkyl, $C_1$-$C_6$ alkylene-$C_6$-$C_{10}$ aryl, or $C_6$-$C_{10}$ aryl, wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_6$ haloalkyl;

$R_4$ is $C_1$-$C_6$ alkyl, wherein the $C_1$-$C_6$ alkyl is optionally substituted with 1 or more substituents independently selected from the group consisting of CN, $C(O)NR_8R_9$, C(O)OH, OH, and $C_6$-$C_{10}$ aryl, wherein any $C_6$-$C_{10}$ aryl is optionally and independently substituted with 1 or more substituents independently selected from the group consisting of halo, CN, $C_1$-$C_4$ alkyl, $C_1$-$C_4$ haloalkyl, OH, $OC_1$-$C_4$ alkyl, and $OC_1$-$C_4$ haloalkyl;

each $R_8$ is independently H, $C_1$-$C_4$ alkyl, or $C_1$-$C_4$ haloalkyl; and each $R_9$ is independently H, $C_1$-$C_4$ alkyl, or $C_1$-$C_4$ haloalkyl.

9. The compound of claim 1, or a pharmaceutically acceptable salt, solvate, stereoisomer, or tautomer thereof, wherein:

X is —$C(O)NR_5$—;

$R_1$ is $NR_5R_6$;

$R_2$ is $C_1$-$C_6$ alkyl or $C_1$-$C_6$ alkylene-$C_6$-$C_{10}$ aryl, wherein the $C_6$-$C_{10}$ aryl is optionally substituted with 1 or more substituents independently selected from the group consisting of halo, CN, $C_1$-$C_4$ alkyl, $C_1$-$C_4$ haloalkyl, and OH;

$R_3$ is $C_1$-$C_6$ alkyl, $C_1$-$C_6$ alkylene-$C_6$-$C_{10}$ aryl, or $C_6$-$C_{10}$ aryl, wherein the $C_6$-$C_{10}$ aryl is optionally substituted with 1 or more substituents independently selected from the group consisting of halo, CN, $C_1$-$C_4$ alkyl, $C_1$-$C_4$ haloalkyl, and OH;

$R_4$ is $C_1$-$C_6$ alkyl, wherein the $C_1$-$C_6$ alkyl is optionally substituted with 1 or more substituents independently selected from the group consisting of C(O)OH, OH, and $C_6$-$C_{10}$ aryl, wherein any $C_6$-$C_{10}$ aryl is optionally substituted with 1 or more substituents independently selected from the group consisting of halo, CN, $C_1$-$C_4$ alkyl, $C_1$-$C_4$ haloalkyl, and OH;

each $R_5$ is independently H or $C_1$-$C_6$ alkyl;

$R_6$ is H, $C_1$-$C_6$ alkyl, or $C(O)R_7$; and $R_7$ is $C_1$-$C_6$ alkyl or $OC_1$-$C_6$ alkyl.

10. The compound of claim 6, wherein the compound is selected from the group consisting of:

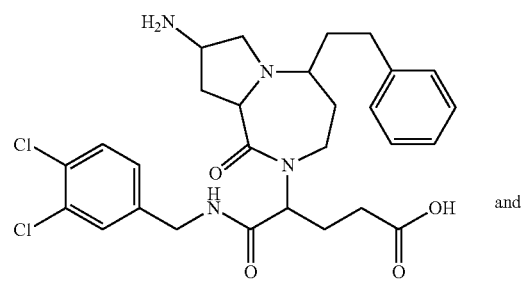

and

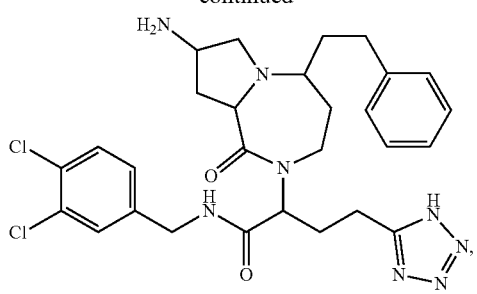
or a pharmaceutically acceptable salt, solvate, stereoisomer, or tautomer thereof.
11. The compound of claim 1, or a pharmaceutically acceptable salt or stereoisomer thereof, wherein the compound, or pharmaceutically acceptable salt or stereoisomer thereof, is selected from the group consisting of:
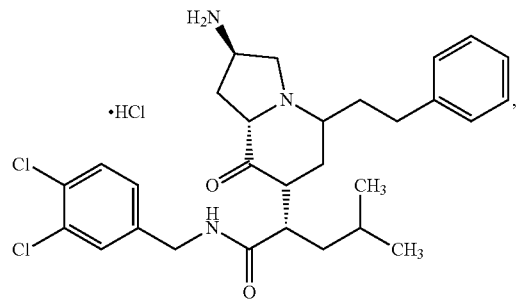
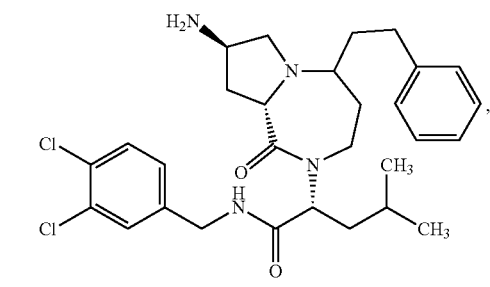
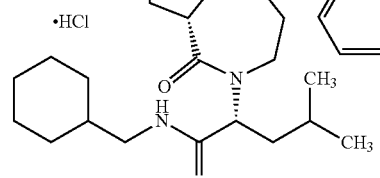
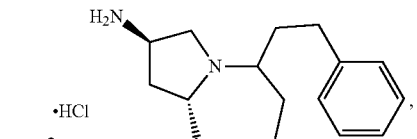
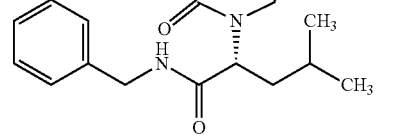
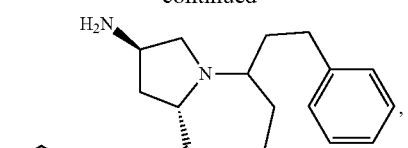
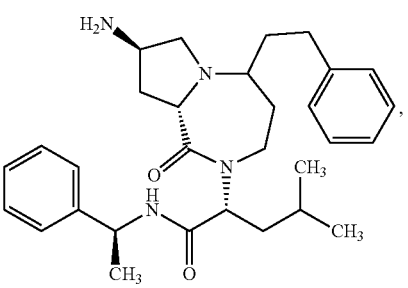
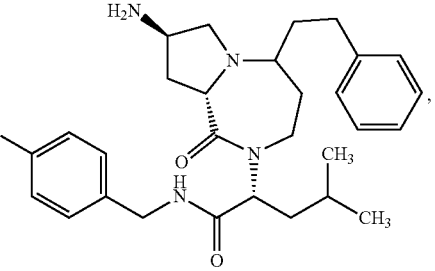
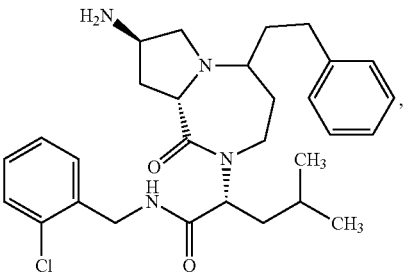
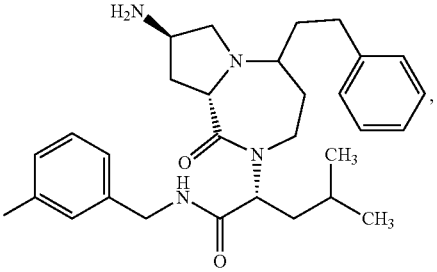
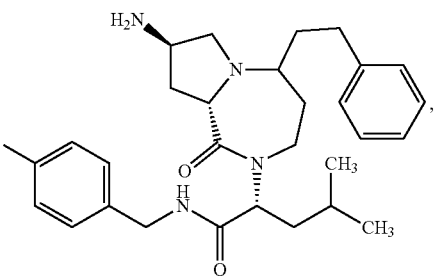

87
-continued
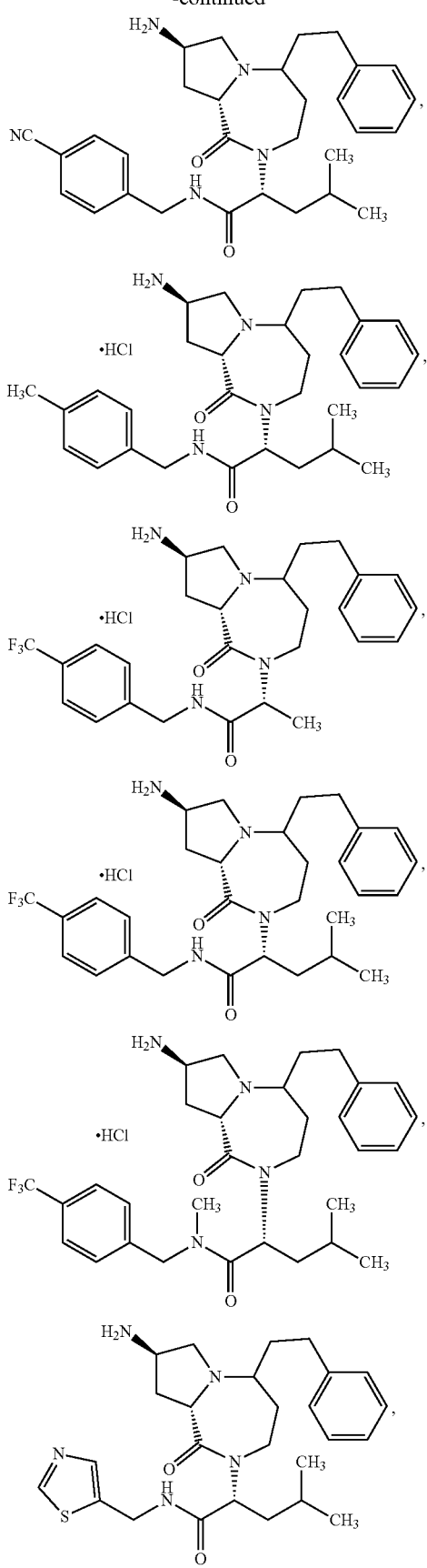
88
-continued
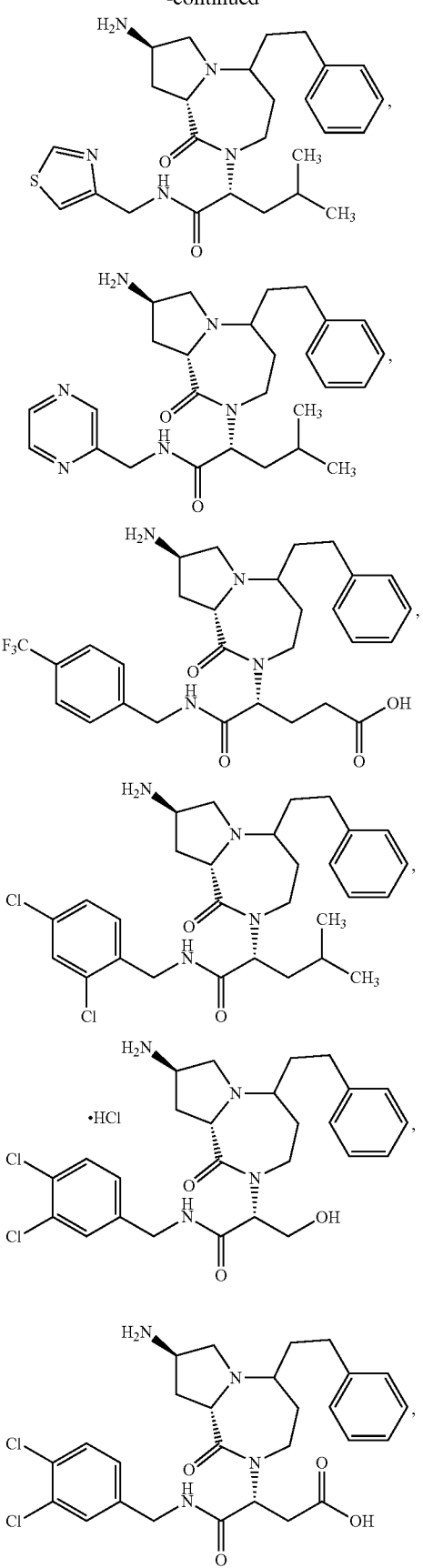

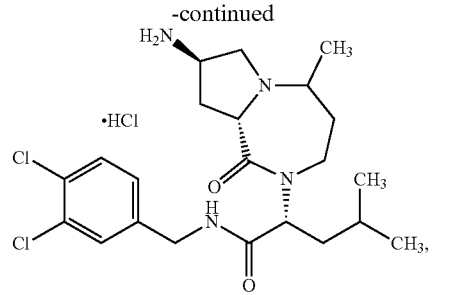
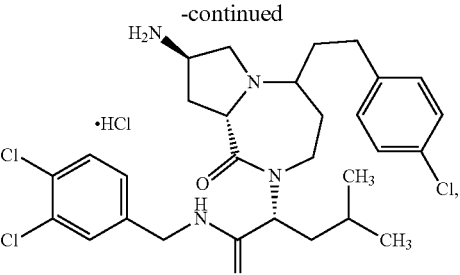
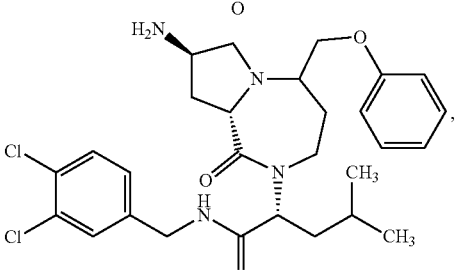
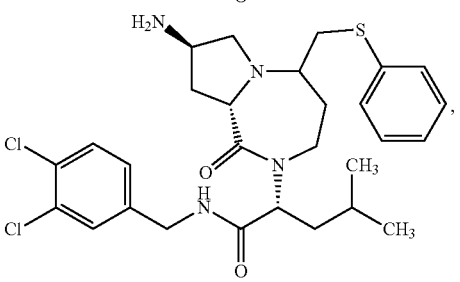
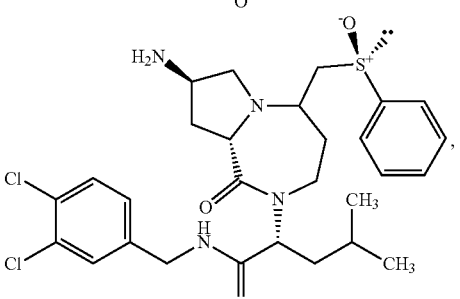
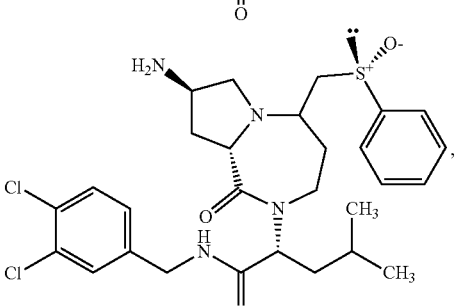
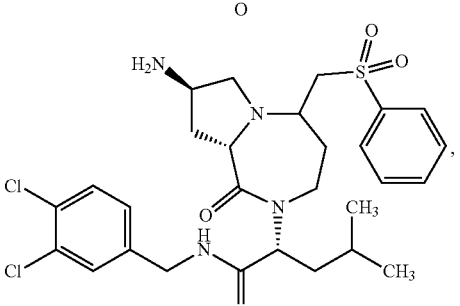

91
-continued
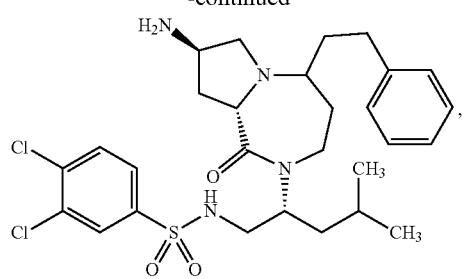
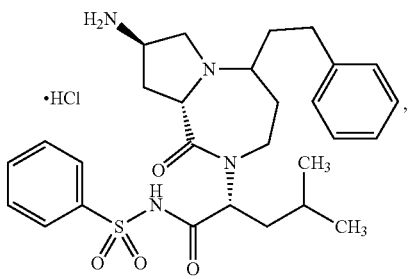
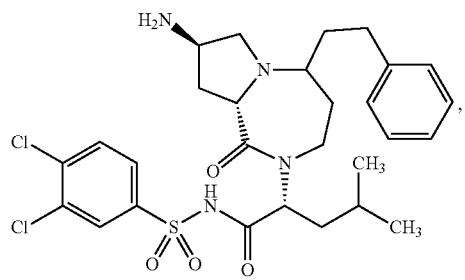
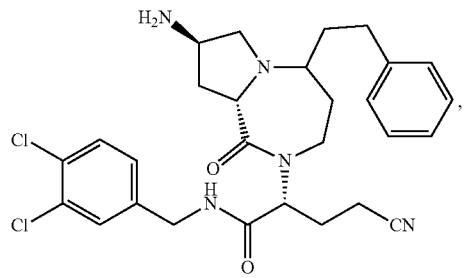
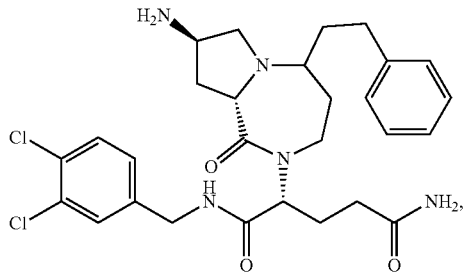
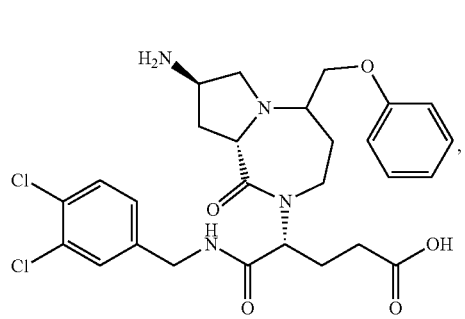
92
-continued
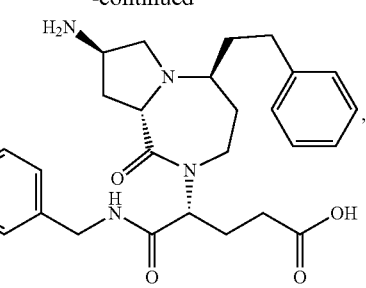
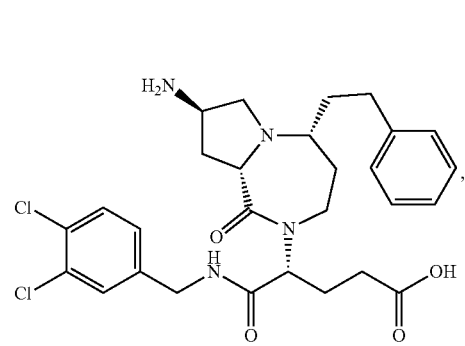
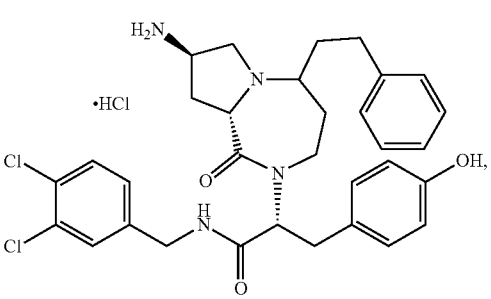
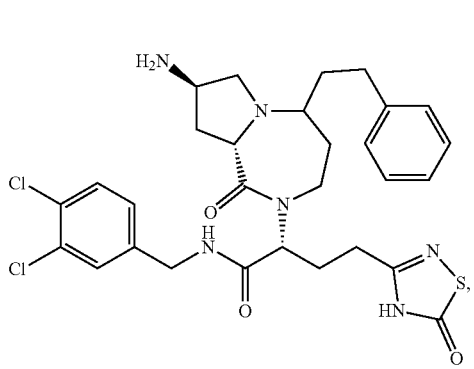
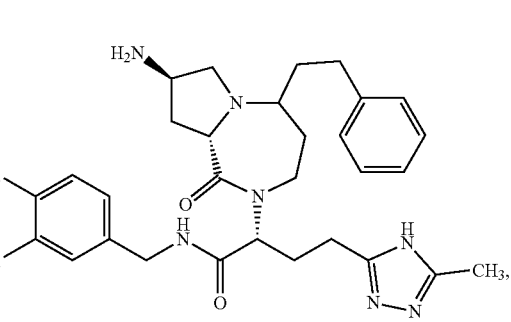

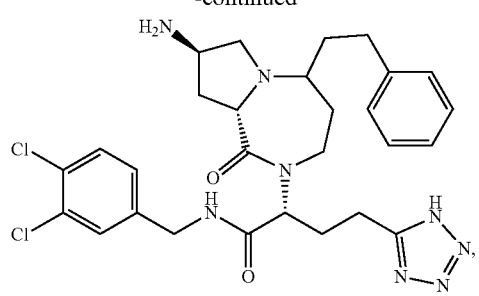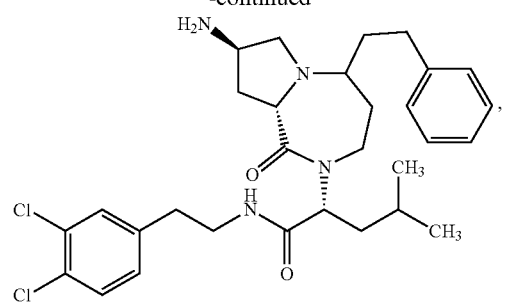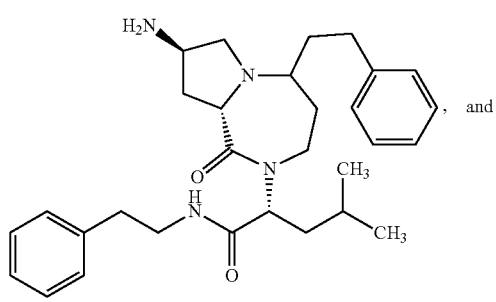

or a solvate or tautomer thereof.

12. A pharmaceutical composition comprising a pharmaceutically acceptable carrier and a compound of claim 1, or a pharmaceutically acceptable salt, solvate, stereoisomer, or tautomer thereof, alone or in combination with another therapeutic agent.

13. The pharmaceutical composition of claim 12, wherein the other therapeutic agent is selected from the group consisting of an anti-cancer agent, an anti-viral compound, an adjuvant, an antigen, a biotherapeutic agent, a cell transfected with a gene that encodes an immune stimulating cytokine, a checkpoint inhibitor, a chemotherapeutic agent, a cytotoxic agent, an immunogenic agent, an immunomodulatory cell line, a lipid, a liposome, and a peptide.

* * * * *

SEQUENCE LISTING

```
<160> NUMBER OF SEQ ID NOS: 2

<210> SEQ ID NO 1
<211> LENGTH: 242
<212> TYPE: PRT
<213> ORGANISM: Homo sapiens

<400> SEQUENCE: 1

Met Gly Ser Gln Ala Leu Pro Pro Gly Pro Met Gln Thr Leu Ile Phe
1               5                   10                  15

Phe Asp Met Glu Ala Thr Gly Leu Pro Phe Ser Gln Pro Lys Val Thr
                20                  25                  30

Glu Leu Cys Leu Leu Ala Val His Arg Cys Ala Leu Glu Ser Pro Pro
            35                  40                  45

Thr Ser Gln Gly Pro Pro Thr Val Pro Pro Pro Arg Val Val
    50                  55                  60

Asp Lys Leu Ser Leu Cys Val Ala Pro Gly Lys Ala Cys Ser Pro Ala
65                  70                  75                  80

Ala Ser Glu Ile Thr Gly Leu Ser Thr Ala Val Leu Ala Ala His Gly
                85                  90                  95

Arg Gln Cys Phe Asp Asp Asn Leu Ala Asn Leu Leu Leu Ala Phe Leu
            100                 105                 110

Arg Arg Gln Pro Gln Pro Trp Cys Leu Val Ala His Asn Gly Asp Arg
        115                 120                 125

Tyr Asp Phe Pro Leu Leu Gln Ala Glu Leu Ala Met Leu Gly Leu Thr
130                 135                 140

Ser Ala Leu Asp Gly Ala Phe Cys Val Asp Ser Ile Thr Ala Leu Lys
145                 150                 155                 160

Ala Leu Glu Arg Ala Ser Ser Pro Ser Glu His Gly Pro Arg Lys Ser
                165                 170                 175

Tyr Ser Leu Gly Ser Ile Tyr Thr Arg Leu Tyr Gly Gln Ser Pro Pro
            180                 185                 190

Asp Ser His Thr Ala Glu Gly Asp Val Leu Ala Leu Leu Ser Ile Cys
        195                 200                 205

Gln Trp Arg Pro Gln Ala Leu Leu Arg Trp Val Asp Ala His Ala Arg
210                 215                 220

Pro Phe Gly Thr Ile Arg Pro Met Tyr Gly Val Thr Ala Ser Ala Arg
225                 230                 235                 240

Thr Lys

<210> SEQ ID NO 2
<211> LENGTH: 242
<212> TYPE: PRT
<213> ORGANISM: Mus musculus

<400> SEQUENCE: 2

Met Gly Ser Gln Thr Leu Pro His Gly His Met Gln Thr Leu Ile Phe
1               5                   10                  15

Leu Asp Leu Glu Ala Thr Gly Leu Pro Ser Ser Arg Pro Glu Val Thr
                20                  25                  30

Glu Leu Cys Leu Leu Ala Val His Arg Arg Ala Leu Glu Asn Thr Ser
            35                  40                  45
```

```
Ile Ser Gln Gly His Pro Pro Pro Val Pro Arg Pro Pro Arg Val Val
 50                  55                  60
Asp Lys Leu Ser Leu Cys Ile Ala Pro Gly Lys Ala Cys Ser Pro Gly
 65              70                  75                  80
Ala Ser Glu Ile Thr Gly Leu Ser Lys Ala Glu Leu Glu Val Gln Gly
                 85                  90                  95
Arg Gln Arg Phe Asp Asp Asn Leu Ala Ile Leu Leu Arg Ala Phe Leu
            100                 105                 110
Gln Arg Gln Pro Gln Pro Cys Cys Leu Val Ala His Asn Gly Asp Arg
        115                 120                 125
Tyr Asp Phe Pro Leu Leu Gln Thr Glu Leu Ala Arg Leu Ser Thr Pro
    130                 135                 140
Ser Pro Leu Asp Gly Thr Phe Cys Val Asp Ser Ile Ala Ala Leu Lys
145                 150                 155                 160
Ala Leu Glu Gln Ala Ser Ser Pro Ser Gly Asn Gly Ser Arg Lys Ser
                165                 170                 175
Tyr Ser Leu Gly Ser Ile Tyr Thr Arg Leu Tyr Trp Gln Ala Pro Thr
            180                 185                 190
Asp Ser His Thr Ala Glu Gly Asp Val Leu Thr Leu Leu Ser Ile Cys
        195                 200                 205
Gln Trp Lys Pro Gln Ala Leu Leu Gln Trp Val Asp Glu His Ala Arg
    210                 215                 220
Pro Phe Ser Thr Val Lys Pro Met Tyr Gly Thr Pro Ala Thr Thr Gly
225                 230                 235                 240
Thr Thr
```